United States Patent [19]

Walker

[11] Patent Number: 4,518,607
[45] Date of Patent: May 21, 1985

[54] MALE ORAL CONTRACEPTIVE N-ALKYLIMIDAZOLE DERIVATIVES, COMPOSITIONS, AND METHOD OF USE THEREFOR

[75] Inventor: Keith A. M. Walker, Los Altos Hills, Calif.

[73] Assignee: Syntex (U.S.A.) Inc., Palo Alto, Calif.

[21] Appl. No.: 514,409

[22] Filed: Jul. 18, 1983

[51] Int. Cl.³ ............... C07D 233/60; A61J 31/415
[52] U.S. Cl. ................................. 514/399; 548/341; 514/397; 514/841
[58] Field of Search ............... 544/60, 96, 139, 333, 544/370, 405; 546/210, 278; 548/146, 202, 215, 235, 255, 262, 269, 336, 341; 424/246, 248.4, 250, 251, 263, 267, 270, 272, , 269, 273 P, 273 R

[56] References Cited

U.S. PATENT DOCUMENTS 3,717,655  2/1973  Godefroi et al. .............. 548/341
3,839,574  10/1974 Godefroi et al. .............. 548/341
3,940,415  2/1976  Büchel et al. ................. 548/341
4,055,652  10/1977 Walker ........................... 424/273 R Primary Examiner—Henry R. Jiles
Assistant Examiner—J. G. Mullins
Attorney, Agent, or Firm—Annette M. Moore; Tom M. Moran

[57] ABSTRACT

A compound useful as antifungal, antibacterial and antiprotozoal agents and as spermicides have the formula

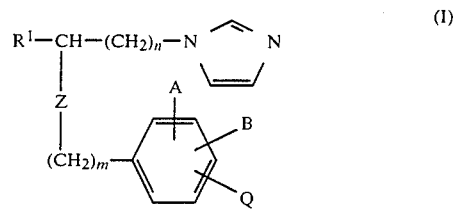

and the acid addition salts thereof wherein Z is oxygen or sulfur;
m is 0, 1, 2 or 3;
n is 1, 2 or 3;
$R^1$ is hydrogen; alkyl; cycloalkyl; cycloalkyl-lower-alkyl; optionally substituted phenyl; phenyl-lower-alkyl; monocyclic heteroaromatic ring; monocyclic heteroaromatic-lower-alkyl; naphthyl; or naphthyl-lower-alkyl.
A and B are independently hydrogen, halo, lower alkyl or lower alkoxy and either one of A or B may be nitro, amino or alkanoylamino;
Q is (a) $NR^2R^3$ or (b) $NR^4C(X)YR^5$ wherein
X is oxygen or sulfur;
Y is oxygen, sulfur, $NR^6$ or a bond;
$R^2$ is hydrogen; alkyl; cycloalkyl; cycloalkyl-lower-alkyl; optionally substituted phenyl or optionally substituted phenyl-lower-alkyl;
$R^3$ is hydrogen or lower alkyl; or
$R^2$ and $R^3$ together with N is a five or six membered optionally substituted ring;
$R^4$ and $R^6$ are independently hydrogen or lower alkyl;
$R^5$ is lower alkyl; cycloalkyl; phenyl; or optionally substituted phenyl or phenyl-lower-alkyl.

25 Claims, No Drawings

MALE ORAL CONTRACEPTIVE N-ALKYLIMIDAZOLE DERIVATIVES, COMPOSITIONS, AND METHOD OF USE THEREFOR

BACKGROUND OF THE INVENTION

1. Field of the Invention

This invention relates to ether and thioether derivatives of N-alkylimidazoles and the acid addition salts thereof, which are useful as antimicrobial agents and as spermicides. The invention also relates to compositions containing an effective amount of at least one of the compounds in combination with a suitable excipient, the composition being useful for combatting fungi, bacteria and protozoa and as spermicides. The invention also relates to a process for making the compounds of the invention.

2. Related Disclosure

Compounds of the following formula are known

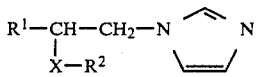

wherein $R^1$ is phenyl optionally substituted by one or more lower alkyl, halo and trifluoromethyl; $R^2$ is alkyl, alkenyl, aralkenyl, alkynyl, cycloalkyl, cycloalkylalkyl, aralkyl or aryl wherein the phenyl ring is optionally substituted by amino when X is oxygen; or amino or alkanoylamino when X is sulfur. See U.S. Pat. Nos. 3,717,655 and 4,055,652.

SUMMARY OF THE INVENTION

The first aspect of the invention is a group of compounds of the formula

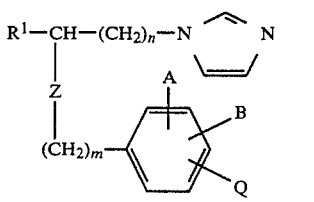

and the acid addition salts thereof wherein

Z is oxygen or sulfur;
m is 0, 1, 2 or 3;
n is 1, 2 or 3;
$R^1$ is
 (a) hydrogen;
 (b) alkyl;
 (c) cycloalkyl optionally substituted by one or more lower alkyl;
 (d) cycloalkyl-lower-alkyl;
 (e) phenyl;
 (f) phenyl-lower-alkyl;
 wherein the phenyl ring in (e) and (f) is optionally substituted by one or more halo, lower alkyl, lower alkoxy, lower alkylthio, cyano or trifluoromethyl;
 (g) monocyclic heteroaromatic ring containing one ring oxygen, nitrogen or sulfur;
 (h) monocyclic heteroaromatic ring-lower-alkyl the ring containing one ring oxygen, nitrogen or sulfur;

wherein the ring in (g) and (h) is bonded through a carbon atom and is optionally substituted by one halo, hydroxy, nitro, lower alkyl, lower alkoxy or lower alkylthio;
 (i) naphthyl; or
 (j) naphthyl-lower-alkyl A and B are independently hydrogen, halo, lower alkyl or lower alkoxy and either one of A or B may be nitro, amino or alkanoylamino;

C is (a) $NR^2R^3$ or (b) $NR^4C(X)YR^5$ wherein

X is oxygen or sulfur;
Y is oxygen, sulfur, $NR^6$ or a bond;
$R^2$ is hydrogen; alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl or lower alkoxy;
$R^3$ is hydrogen or lower alkyl; or
$R^2$ and $R^3$ together with N is
 (i) a five or six membered heteroaromatic ring optionally containing additional ring nitrogen, oxygen or sulfur, the ring optionally substituted by a compatible substituent selected from the group consisting of hydroxy, amino, lower alkylamino, di(lower alkyl)amino, alkanoylamino, lower alkoxy, thio, lower alkylthio, oxo, thiono, imino, acylimino, lower alkylimino, lower alkyl, phenyl optionally substituted by one or two halo, lower alkyl, lower alkoxy, nitro, amino, lower alkylamino, di(lower alkyl)amino or alkanoylamino and benzyl optionally substituted by one or two halo, lower alkyl or lower alkoxy; or
 (ii) a five or six membered nonaromatic ring optionally containing additional ring oxygen, sulfur or $NR^7$ wherein $R^7$ is $C(X)YR^5$ wherein X and Y are as is defined above and $R^5$ is as defined below; hydrogen; lower alkyl; phenyl optionally substituted by one or two lower alkyl, lower alkoxy or halo; or benzyl optionally substituted by one or two lower alkyl, lower alkoxy or halo; or optionally substituted on a ring carbon by oxo, thiono, lower alkyl, or phenyl optionally substituted by one or two halo, lower alkyl;

$R^4$ and $R^6$ are independently hydrogen or lower alkyl;

$R^4$ and $R^6$ are independently hydrogen or lower alkyl;

$R^5$ is lower alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl, lower alkoxy, trifluoromethyl or $R^5$ may be hydrogen when Y is $NR^6$ with the proviso that when $R^1$ is optionally substituted phenyl, thienyl or halothienyl, Z is oxygen, n is 1 and m is 0, 1 or 2, Q is not amino unless A or B is alkanoylamino; and that when $R^1$ is optionally substituted phenyl, Z is sulfur, m is 0 and n is 1, Q is not amino or alkanoylamino.

Another aspect of the invention is a composition containing at least one compound of formula (I) in admixture with an acceptable carrier useful in combatting fungi, bacteria and protozoa or as a spermicide.

Another aspect of the invention is a method of contraception using at least one compound of formula (I).

Another aspect of the invention is a method of combatting fungi, bacteria and protozoa by administering at least one compound of formula (I).

Yet another aspect of the invention is a process for preparing compounds of formula (I).

DETAILED DESCRIPTION OF THE INVENTION AND PREFERRED EMBODIMENTS

The broadest aspect of the present invention is a group of compounds of the formula

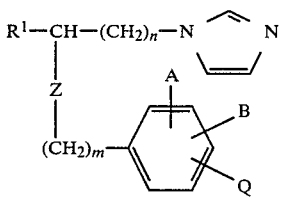

and the acid addition salts thereof wherein

Z is oxygen or sulfur;

m is 0, 1, 2 or 3;

n is 1, 2 or 3;

$R^1$ is (a) hydrogen;

(b) alkyl;

(c) cycloalkyl optionally substituted by one or more lower alkyl;

(d) cycloalkyl-lower-alkyl;

(e) phenyl;

(f) phenyl-lower-alkyl;

wherein the phenyl ring in (e) and (f) is optionally substituted by one or more halo, lower alkyl, lower alkoxy, lower alkylthio, cyano or trifluoromethyl;

(g) monocyclic heteroaromatic ring containing one ring oxygen, nitrogen or sulfur;

(h) monocyclic heteroaromaticing-lower-alkyl the ring containing one ring oxygen, nitrogen or sulfur;

wherein the ring in (g) and (h) is bonded through a carbon atom and is optionally substituted by one halo, hydroxy, nitro, lower alkyl, lower alkoxy or lower alkylthio;

(i) naphthyl; or (j) naphthyl-lower-alkyl

A and B are independently hydrogen, halo, lower alkyl or lower alkoxy and either one of A or B may be nitro, amino or alkanoylamino;

Q is (a) $NR^2R^3$ or (b)$NR^4C(X)YR^5$ wherein

X is oxygen or sulfur;

Y is oxygen, sulfur, $NR^6$ or a bond;

$R^2$ is hydrogen; alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl or lower alkoxy;

$R^3$ is hydrogen or lower alkyl; or $R^2$ and $R^3$ together with N is (i) a five or six membered heteroaromatic ring optionally containing additional ring nitrogen, oxygen or sulfur, the ring optionally substituted by a compatible substituent selected from the group consisting of hydroxy, amino, lower alkylamino, di(lower alkyl)amino, alkanoylamino, lower alkoxy, thio, lower alkylthio, oxo, thiono, imino, acylimino, lower alkylimino, lower alkyl, phenyl optionally substituted by one or two halo, lower alkyl, lower alkoxy, nitro, amino, lower alkylamino, di(-lower alkyl)amino or alkanoylamino and benzyl optionally substituted by one or two halo, lower alkyl or lower alkoxy; or (ii) a five or six membered nonaromatic ring optionally containing additional ring oxygen, sulfur or $NR^7$ wherein $R^7$ is $C(X)YR^5$ wherein X and Y are as is defined above and $R^5$ is as defined below; hydrogen; lower alkyl; phenyl optionally substituted by one or two lower alkyl, lower alkoxy or halo; or benzyl optionally substituted by one or two lower alkyl, lower alkoxy or halo; or optionally substituted on a ring carbon by oxo, thiono, lower alkyl, or phenyl optionally substituted by one or two halo, lower alkyl;

$R^4$ and $R^6$ are independently hydrogen or lower alkyl;

$R^5$ is lower alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl, lower alkoxy, trifluoromethyl or $R^5$ may be hydrogen when Y is $NR^6$ with the proviso that when $R^1$ is optionally substituted phenyl, thienyl or halothienyl, Z is oxygen, n is 1 and m is 0, 1 or 2, Q is not amino unless A or B is alkanoylamino; and that when $R^1$ is optionally substituted phenyl, Z is sulfur, m is 0 and n is 1, Q is not amino or alkanoylamino.

As used in the specification and the appended claims, unless specified to the contrary, the following terms have the meaning indicated. The term "alkyl" refers to a straight or branched chain monovalent substituent consisting solely of carbon and hydrogen, containing no unsaturation, and having from one to twelve carbon atoms. Examples of alkyl groups are methyl, ethyl i-propyl, t-butyl, n-hexyl, n-octyl, n-decyl, and n-dodecyl. The term "lower alkyl" refers to alkyl groups as defined above containing one to six carbon atoms. Examples of lower alkyl groups are methyl, ethyl, n-propyl, i-propyl, n-butyl, i-butyl, s-butyl, t-butyl, pentyl and hexyl. "Cycloalkyl" refers to a cyclic saturated monovalent substituent consisting solely of carbon and hydrogen and having five to seven carbon atoms in the ring. Examples of cycloalkyl are cyclopentyl, cyclohexyl and cycloheptyl. "Cycloalkyl-lower-alkyl" refers to a cycloalkyl group as defined above attached to an alkylene chain of one to four carbon atoms. Non-limiting examples of cycloalkyl-lower-alkyl are cyclohexyl-n-propyl, cyclopentylethyl and cyclohexylmethyl.

"Phenyl-lower-alkyl" refers to an unsubstituted or substituted phenyl ring attached to an alkylene chain of one to three carbon atoms. Examples of phenyl-lower-alkyl groups are 4-methylphenylmethyl, 4-chlorophenylethyl and phenyl-n-propyl.

The term "lower alkoxy" refers to a straight or branched chain monovalent substituent consisting solely of carbon, hydrogen and oxygen and of the formula "lower alkyl-0-" wherein "lower alkyl" is as defined above Examples of lower alkoxy groups are methoxy, ethoxy, n-propoxy, i-propoxy, n-butoxy, i-butoxy, t-butoxy, and n-hexyloxy. The term "lower alkylthio" refers to a straight or branched chain monovalent substituent consisting solely of carbon, hydrogen and sulfur and of the formula "lower alkyl-S-" wherein lower alkyl is as defined above. Examples of lower alkylthio groups are methylthio, ethylthio, n-propylthio, i-propylthio, n-butylthio, i-butylthio, t-butylthio, and n-pentylthio. The term "halo" refers to fluoro, chloro and bromo.

The terms "cyano, hydroxy, nitro, amino, thio, oxo, thiono and imino" as used herein are used in their common meaning as defined in *Hackh's Chemical Dictionary*, 4th Ed., Editor: Julius Grant, 1972.

The term "heteroaromatic" refers to a five or six membered ring containing an oxygen, nitrogen or sulfur atom and containing aromatic unsaturation. Examples of heteroaromatic groups are furanyl, thienyl, and pyridinyl.

The term "alkanoylamino" refers to the group —NHC(0)R wherein R is lower alkyl as defined above. Examples of alkanoylamino groups are acetylamino, propanoylamino, n-butanoylamino and n-hexanoylamino. The term "acylimino" refers to the group =NC(0)R wherein R is lower alkyl is defined above. Examples of acylimino are acetylimino, i-butanoylimino, n-pentanoylimino and n-hexanoylimino. The term "alkylimino" refers to the group =NR wherein R is lower alkyl as defined above. Examples of alkylimino groups are methylimino, ethylimino, n-propylimino, i-butylimino and n-hexylimino. The term "lower alkylamino" refers to the group —NHR wherein R is lower alkyl Examples of lower alkylamino are methylamino, ethylamino, n-propylamino, i-butylamino, n-pentylamino and n-hexylamino. The term "lower dialkylamino" refers to the group —NRR wherein R is lower alkyl. Examples of lower dialkylamino groups are dimethylamino, methylethylamino, dipropylamino, dibutylamino and dihexylamino.

When Q is $NR^4C(X)YR^5$ the following specific groups are intended wherein $R^4$, $R^5$ and $R^6$ are as defined above. The term "hydrocarbyl" refers generically to $R^4$, $R^5$, and $R^6$ and "amino" refers to appropriately substituted amine groups:

| Specific Group | Name |
|---|---|
| $NR^4C(O)$-$R^5$ | acylamino |
| $NR^4C(O)OR^5$ | hydrocarbyloxycarbonylamino |
| $NR^4C(O)SR^5$ | (hydrocarbylthio)carbonylamino |
| $NR^4C(O)NR^6R^5$ | aminocarbonylamino |
| $NR^4C(S)$-$R^5$ | hydrocarbyl(thiocarbonyl)amino |
| $NR^4C(S)OR^5$ | hydrocarbyloxy(thiocarbonyl)amino |
| $NR^4C(S)SR^5$ | (hydrocarbylthio)thiocarbonylamino |
| $NR^4C(S)NR^6R^5$ | aminothiocarbonylamino |

The phrase "$R^2$ and $R^3$ together with N is a five or six membered ring optionally containing additional ring oxygen, nitrogen or sulfur atoms" refers to monocyclic saturated and unsaturated five or six membered ring systems optionally containing one or two hetero atoms in addition to the nitrogen atom. Examples of such ring system are piperidinyl, morpholinyl, pyrazinyl, piperazinyl, pyrimidinyl, pyridazinyl, thiamorpholinyl, 1,3-oxazinyl, pyrazolyl, pyridinyl, pyrrolidinyl, pyrrolyl, imidazolidinyl, imidazolyl, 1,3-oxazolyl, 1,3-oxazolidinyl, thiazolyl, thiazolidinyl, 1,2,3-triazolyl, 1,2,4-triazolyl and, where appropriate, the saturated derivatives of the above heterocyclic systems.

"Acid addition salts" of the subject bases refers to those salts which possess the pharmaceutical or antimicrobial properties of the free bases and which are neither biologically nor otherwise undesirable, formed with, for example, inorganic acids such as hydrochloric acid, hydrobromic acid, sulfuric acid, nitric acid or phosphoric acid; or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

It is understood, for purposes of this invention, that the phenyl ring of $R^1$ cannot be substituted with three or more adjacent branched alkyl, branched alkoxy and/or trifluoromethyl groups.

Compounds of formula (I) (except those wherein $R^1$ is hydrogen) possess at least one asymmetric carbon atom. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subject compounds.

If desired, racemic intermediates or final products prepared herein may be resolved into their optical antipodes by conventional resolution means known per se, for example, by the separation (e.g. fractional crystallization) of the diastereomeric salts formed by reaction of, e.g., racemic compounds of formulas (I), or (II) with an optically active acid, or by the separation of the diastereomeric esters formed by reaction of racemic compounds of formula (II), with an optically active acid. Exemplary of such optically active acids are the optically active forms of camphor-10-sulfonic acid, 1-bromo-camphor-$\pi$-sulfonic acid, camphoric acid, menthoxyacetic acid, tartaric acid, malic acid, diacetyltartaric acid, pyrrolidone-5-carboxylic acid, and the like. Certain racemic compounds of formula (I) may also be resolved by separation of the diastereomeric amides formed with an optically active acid. The separated pure diastereomeric salts, amides or esters may then be cleaved by standard means to afford the respective optical isomers of the compounds of formula (I) or (II). (I) One subgenus of compounds of formula (I) is that wherein $R^1$ is selected from the group consisting of hydrogen, alkyl, cycloalkyl optionally substituted by one or more lower alkyl and cycloalkyl-lower-alkyl. When $R^1$ is alkyl, alkyl of two of twelve carbon atoms is preferred.

A subgroup within this subgenus is that wherein Q is $NR^2R^3$. Within this subgroup are those compounds wherein $R^2$ is hydrogen; alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl or lower alkoxy; and $R^3$ is hydrogen or lower alkyl.

Another subgroup is that wherein $R^2$ and $R^3$ together with N is (i) a five or six membered heteroaromatic ring optionally containing additional ring nitrogen, oxygen or sulfur, the ring optionally substituted by a compatible substituent selected from the group consisting of hydroxy, amino, lower alkylamino, di(lower alkyl)amino, alkanoylamino, lower alkoxy, thio, lower alkylthio, oxo, thiono, imino, acylimino, lower alkylimino, lower alkyl, phenyl optionally substituted by one or two halo, lower alkyl, lower alkoxy, nitro, amino, lower alkylamino, di(lower alkyl)amino or alkanoylamino and benzyl optionally substituted by one or two halo, lower alkyl or lower alkoxy; or (ii) a five or six membered nonaromatic ring optionally containing additional ring oxygen, sulfur or $NR^7$ wherein $R^7$ is $C(X)YR^5$ wherein $R^5$, X and Y are as is defined above; hydrogen; lower alkyl; phenyl optionally substituted by one or two lower alkyl, lower alkoxy or halo; or benzyl optionally substituted by one or two lower alkyl, lower alkoxy or halo; or optionally substituted on a ring carbon by oxo, thiono, lower alkyl, or phenyl optionally substituted by one or two halo, lower alkyl or lower alkoxy.

Within this subgroup it is preferred that the aromatic ring is selected from the group consisting of pyrrolyl, imidazolyl, pyrazolyl, 1,2,3-triazolyl and 1,2,4-triazolyl wherein the ring is optionally subsituted by lower alkyl and the nonaromatic ring is selected from the group consisting of piperazinyl wherein $R^7$ is as defined above, pyrrolidinyl, piperidinyl, morpholinyl and thiamorpholinyl.

Another subgroup of compounds is that wherein Q is $NR^4C(X)YR^5$ wherein $R^4$, $R^5$, X and Y are as defined above.

(II) Another subgenus of compounds of formula (I) is that wherein $R^1$ is selected from the group consisting of monocylic heteraromatic ring and monocylic heteroaromatic-lower-alkyl wherein the ring is attached through a carbon atom and is optionally substituted by one halo, hydroxy, nitro, lower alkyl, lower alkoxy or lower alkylthio.

A subgroup within this subgenus is that wherein Q is $NR^2R^3$. Within this subgroup are those compounds wherein $R^2$ is hydrogen; alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl or lower alkoxy; and $R^3$ is hydrogen or lower alkyl.

Another subgroup is that wherein $R^2$ and $R^3$ together with N is (i) a five or six membered heteroaromatic ring optionally containing additional ring nitrogen, oxygen or sulfur, the ring optionally substituted by a compatible substituent selected from the group consisting of hydroxy, amino, lower alkylamino, di(lower alkyl)amino, alkanoylamino, lower alkoxy, thio, lower alkylthio, oxo, thiono, imino, acylimino, lower alkylimino, lower alkyl, phenyl optionally substituted by one or two halo, lower alkyl, lower alkoxy, nitro, amino, lower alkylamino, di(lower alkyl)amino or alkanoylamino and benzyl optionally substituted by one or two halo, lower alkyl or lower alkoxy; or (ii) a five or six membered nonaromatic ring optionally containing additional ring oxygen, sulfur or $NR^7$ wherein $R^7$ is $C(X)YR^5$ wherein $R^5$, X and Y are as is defined above; hydrogen; lower alkyl; phenyl optionally substituted by one or two lower alkyl, lower alkoxy or halo; or benzyl optionally substituted by one or two lower alkyl, lower alkoxy or halo; or optionally substituted on a ring carbon by oxo, thiono, lower alkyl, or phenyl optionally substituted by one or two halo, lower alkyl or lower alkoxy Within this subgroup it is preferred that the aromatic ring is selected from the group consisting of pyrrolyl, imidazolyl, pyrazolyl, 1,2,3-triazolyl and 1,2,4-triazolyl wherein the ring is optionally subsituted by lower alkyl and the nonaromatic ring is selected from the group consisting of piperazinyl wherein $R^7$ is as defined above, pyrrolidinyl, piperidinyl, morpholinyl and thiamorpholinyl.

Another subgroup of compounds is that wherein Q is $NR^4C(X)YR^5$ wherein $R^4$, $R^5$, X and Y are as defined above.

(III) Another subgroup of compounds of formula (I) is that wherein $R^1$ is selected from the group consisting of phenyl, phenyl-lower-alkyl, naphthyl and naphthyl-lower-alkyl wherein the phenyl ring is optionally substituted by one or more halo, lower alkyl, lower alkoxy, lower alkylthio, cyano or trifluoromethyl. Within this subgroup it is preferred that $R_1$ is substituted phenyl-lower-alkyl with lower-alkyl of two to three carbon atoms being most preferred.

A subgroup within this subgenus is that wherein Q is $NR^2R^3$. Within this subgroup are those compounds wherein $R^2$ is hydrogen; alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl or lower alkoxy; and $R^3$ is hydrogen or lower alkyl. It is preferred that $R^2$ and $R^3$ are both the same and are hydrogen or lower alkyl.

Another subgroup is that wherein $R^2$ and $R^3$ together with N is (i) a five or six membered heteroaromatic ring optionally containing additional ring nitrogen, oxygen or sulfur, the ring optionally substituted by a compatible substituent selected from the group consisting of hydroxy, amino, lower alkylamino, di(lower alkyl)amino, alkanoylamino, lower alkoxy, thio, lower alkylthio, oxo, thiono, imino, acylimino, lower alkylimino, lower alkyl, phenyl optionally substituted by one or two halo, lower alkyl, lower alkoxy, nitro, amino, lower alkylamino, di(lower alkyl)amino or alkanoylamino and benzyl optionally substituted by one or two halo, lower alkyl or lower alkoxy; or (ii) a five or six membered nonaromatic ring optionally containing additional ring oxygen, sulfur or $NR^7$ wherein $R^7$ is $C(X)YR^5$ wherein $R^5$, X and Y are as is defined above; hydrogen; lower alkyl; phenyl optionally substituted by one or two lower alkyl, lower alkoxy or halo; or benzyl optionally substituted by one or two lower alkyl, lower alkoxy or halo; or optionally substituted on a ring carbon by oxo, thiono, lower alkyl, or phenyl optionally substituted by one or two halo, lower alkyl or lower alkoxy.

Within this subgroup it is preferred that the aromatic ring is selected from the group consisting of pyrrolyl, imidazolyl, pyrazolyl, 1,2,3-triazolyl and 1,2,4-triazolyl wherein the ring is optionally subsituted by lower alkyl and the nonaromatic ring is selected from the group consisting of piperazinyl wherein $R^7$ is as defined above, pyrrolidinyl, piperidinyl, morpholinyl and thiamorpholinyl.

Another subgroup is that wherein Q is $NR^4C(X)YR^5$ wherein $R^4$, $R^5$, X and Y are as defined above. A preferred group within this subgroup is that wherein $R^4$ is hydrogen, X is oxygen, Y is a bond and $R^5$ is alkyl with $R^5$ being methyl being the most preferred.

FORMULATIONS AND ADMINISTRATIONS

The compounds of Formula (I) herein and the pharmaceutically acceptable non-toxic acid addition salts thereof are useful as spermicides, either intravaginally administered to the female mammal or orally or parenterally administered to the male mammal.

"Spermicide" and "spermicidal" refer to the capacity to render spermatozoa ineffective. This effect may be the result of actual sperm cell death, or less drastically, immobility, cell membrane alteration or other impairment which results in the inability of the sperm cell to effect fertilization.

Compositions appropriate for such uses are prepared by methods and contain ingredients which are well known in the art. A generally recognized compendium of such methods and ingredients is *Remington's Pharmaceutical Sciences* by E. W. Martin, (Mack Publ. Co., 16th Ed., 1980).

For intravaginal administration suitable formulations are, for example, creams, gels, spray foams, suppositories and the like, as well as slow release materials. Each composition contains an effective amount of active ingredient plus one or more pharmaceutically acceptable excipients. Such excipients are, for example, starch, glucose, lactose, talc, cellulose and the like for solid formulations; polyethylene glycols, modified vegetable oils, mineral oil, or polyalkylene glycols and the like for semi-solid formulations; and water, alcohols, glycerol, lanolin, mineral oil and the like for liquid or semi-liquid compositions. The compositions may contain between about 0.01 and 10.0 percent by weight of the active ingredient, preferably between 0.1 and 1.0%, and may, if desired, contain other active ingredients. Such compositions may also be used in conjunction with barrier methods such as, e.g., diaphragms or condoms.

In the practice of the method of contraception herein, the above formulations are administered to the female before coitus, within a period of about 12 hours prior thereto. The preferred dosage range of active ingredient is from about 3 mg to 50 mg per vaginal administration for an adult human. For smaller mammals the amount would be correspondingly smaller.

Compositions for administration to the male are preferably directed to oral administration, although parenteral administration is also biologically possible. Such compositions will contain a spermicidal amount of active ingredient with a non-toxic, pharmaceutically effective carrier. For said oral administration solid dosage forms such as tablets, capsules and powders may contain such excipients as, for example, lactose, starch, or cellulose.

In the practice of the method of contraception herein, a dose in the range of between about 0.1 and 30 mg active ingredient per kg will be administered to the male prior to coitus, preferably at least ½ hour before coitus, or may be administered daily.

The subject compounds of formula (I) also exhibit antifungal, antibacterial and antiprotozoal activity. For example, compounds of the present invention exhibit antifungal activity against human and animal pathogens such as

*Microsporum audouini,*
*Microsporum gypseum,*
*Microsporum gypseum-canis,*
*Epidermophyton floccosum,*
*Trichophyton mentagrophytes,*
*Trichophyton rubrum,*
*Trichophyton tonsurans,*
*Candida albicans,*
*Cryptococcus neoformans,*
  *Blastomyces dermatitidis,*
  *Candida parapsilosis,*
*Candida tropicalis,* and
*Candida pseudotropicalis.*

The compounds of the present invention also exhibit antifungal activity against the following fungi primarily of agricultural significance:

*Aspergillus flavus,*
*Cladosporium herbarum,*
*Fusarium graminearum,*
*Penicillium notatum,*
*Aspergillus niger,*
*Penicillium oxalicum,*
*Penicillium spinulosum,* and
*Pithomyces chartarum.*

In addition, the compounds of the present invention exhibit antibacterial activity against human and animal pathogens, such as

*Staphylococcus aureus,*
*Streptococcus faecalis,*
*Corynebacterium acnes,*
*Erysipelothrix insidiosa,*
*Escherischia coli,*
*Proteus vulgaris,*
*Salmonella choleraesuis,*
*Pasteurella multocida,* and
*Pseudomonas aeruginosa.*

Moreover, the compounds of the present invention exhibit antiprotozoal activity against protozoa such as *Trichomonas vaginalis, Trichomonas foetus, Trypanosoma cruzi, Trypanosoma brucei,* Leishmania sp. and Plasmodium In general, the subject compounds of the instant invention exhibit a low level of toxicity. Furthermore, the compounds of the instant invention attain high blood serum levels when administered orally or parenterally and are particularly useful in the treatment of systemic fungal infections or for systemic treatment of topical infections.

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural, and industrial use, which compositions comprise the subject compounds of formula (I) in combination with a suitable carrier. A still further aspect of the present invention relates to methods of inhibiting the growth of fungi, bacteria and protozoa by applying to a host object containing, or subject to attack by, fungi, bacteria or protozoa, an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, polyalkylene glycols, vaseline and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers The compositions may also contain other therapeutically active materials. In pharmaceutical applications, the subject compounds and compositions may be administered to humans and animals by conventional methods, e.g., topically, orally, parenterally and the like. Parenteral administration includes intramuscular as well as subcutaneous and intravenous administration. Oral administration of imidazole-type antifungals has been demonstrated to be effective in the treatment of superficial and systemic mycoses (see for example, Drugs, 23, pp. 1–36, 1982, which describes the oral administration of ketoconazole to patients with a wide range of systemic and topical infections.

The pharmaceutical compositions hereof typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, for systemic (e.g., oral or parenteral) administration it is expedient to administer the active ingredient in amounts between about 0.1 and 50 mg/kg. body weight per day, preferably between about 0.5 and 20 mg/kg. body weight per day, preferably distributed over several applications (e.g., in 3 individual doses) in order to achieve most effective results. For localized (e.g., topical) administration, however, proportionately less of the active ingredient is required The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner.

In addition, certain compounds of the present invention exhibit steroid synthesis inhibition or promotion, thromboxane synthetase inhibition, uterine relaxant activity, CNS activity e.g., anticonvulsant activity, anthelmintic activity and lipid lowering activity In agricultural applications, the subject compounds may be applied directly to plants (e.g., seeds, foilage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

The compounds of formula (I) can be considered to consist of two subclasses, those of formulas (Ia) and (Ib) shown below:

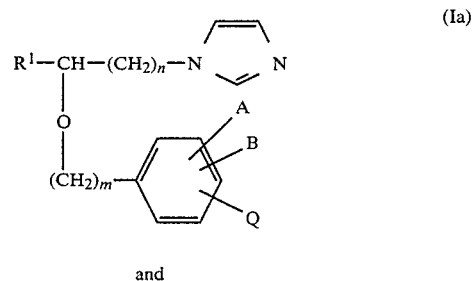

and

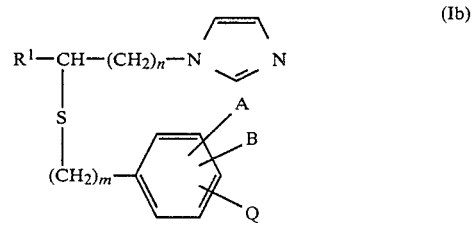

wherein $R^1$, A, B, C, m and n are as defined above.

PROCESS OF THE INVENTION

Compounds of the formula (I) may be prepared by forming an ether or thioether from a suitable alcohol of formula (II)

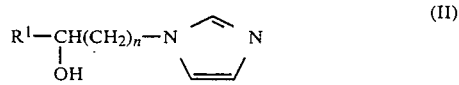

wherein $R^1$ and n are as defined above.

Compounds of formula (II) may be prepared by a variety of reaction sequences, depending on the size of n.

For example, when n is 1, certain compounds of formula (II), i.e., compounds of formula (IIa) may be prepared by reaction sequence A shown below.

REACTION SEQUENCE A

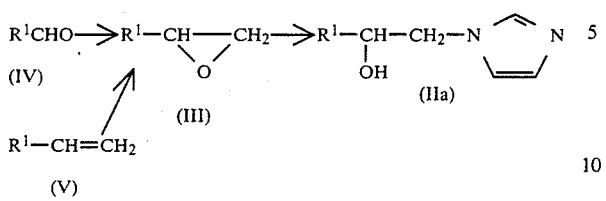

In this reaction sequence the imidazole alcohol of formula (IIa) is formed by opening of a terminal epoxide of formula (III) with imidazole. This reaction is generally carried out using at least one mole and preferably an excess of imidazole relative to epoxide. The reaction may either be carried out in the absence of solvent or, preferably, in an inert organic solvent, for example, a solvent such as dimethylformamide, hexamethylphosphoramide, acetonitrile, and the like. The epoxide opening is preferably carried out using a metal salt (preferably an alkali metal salt) of imidazole, e.g., the sodium salt of imidazole, used catalytically in the presence of imidazole free base as a proton source. A preferred solvent is dimethylformamide. The temperature normally employed for such epoxide opening is in the range of from about $-20°$ to about $100°$ C. Most preferably from about $20°$ to about $85°$ C.

Epoxides of formula (III) insofar as they may not be known or readily available, may be prepared by a variety of well known methods, for example epoxidation of a terminal olefin (e.g.,(V)) with, for example, a peracid or by reaction of an aldehyde having one fewer carbon atoms (e.g.,(IV)) with the ylide prepared fom trimethysulfoxonium foxonium iodide as described, for example, in J. Am. Chem. Soc., 84, 867 (1962) and ibid, 87, 1353 (1965).

Another reaction sequence for preparing certain compounds of formula (IIa) is shown in reaction sequence B presented below:

REACTION SEQUENCE B

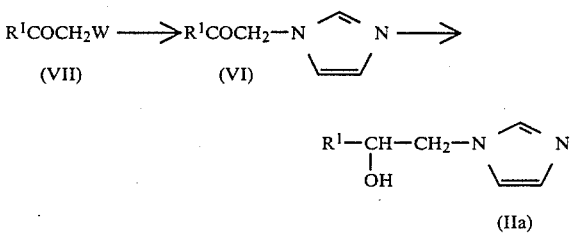

wherein W is chloro or bromo.

In this reaction sequence the hydroxy compound of formula (IIa) is prepared by reduction of the corresponding ketone (VI), which in turn is prepared by reaction of an alpha-halo ketone (VII) with imidazole. Alpha-halo ketones are generally available, or may be readily prepared by, for example, halogenation of the corresponding methyl ketone. Alpha-halo ketones may also be readily prepared by, for example, conversion of the acyl chloride $R^1C(O)Cl$ to the diazoketone $R^1C(O)CHN_2$ with diazomethane followed by treatment with acid HW, or as described in Reaction Sequence H (see compound (XVIII), n=1), or by the Friedel-Crafts reaction involving the aromatic hydrocarbon $R^1H$ and an alpha-halo acetyl halide.

The alpha-halo ketone is contacted with imidazole to form compound of formula (VI). The reaction is carried out utilizing at least a molar amount and, preferably, an excess of imidazole relative to halo ketone. The reaction may be carried out in the absence of solvent or, preferably, in an inert organic solvent such as, for example, dimethylformamide, hexamethylphosphoramide, acetonitrile, and the like. The reaction is suitably carried out at a temperature initially between about $-10°$ and $100°$ C., most preferably between about $0°$ and $25°$ C.

In the next step the keto imidazole of formula (VI) is reduced to the hydroxy imidazole of formula (IIa) utilizing a conventional metal hydride reducing agent such as, for example, sodium borohydride. The reaction is suitably carried out in an alcoholic solvent such as, for example, methanol or ethanol at a reduced temperature, for example, between about $-10°$ and $+25°$ C., most preferably about $0°$ C.

A preferred method for preparing certain compounds of formula (IIa) is illustrated in reaction sequence C, shown below

REACTION SEQUENCE C

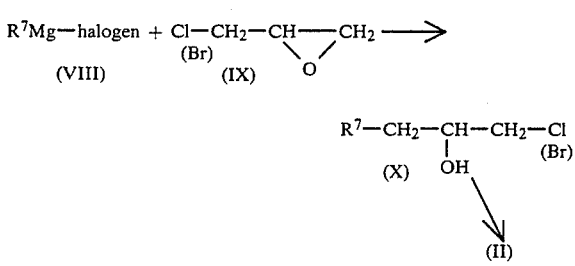

wherein $R^7CH_2$ is $R^1$ where $R^1$ is alkyl of two or more carbon atoms, cycloalkyl-lower-alkyl, phenyl-lower-alkyl, certain monocyclic heteroaromatic-lower-alkyl and naphthyl-lower-alkyl.

In this sequence the appropriately substituted $R^7$ Grignard reagent (VIII) is reacted with epichlorohydrin (or epibromohydrin) (IX) to afford the halohydrin (X). This reaction is carried out in typical solvents for performing Grignard reactions, namely ether-containing solvents, preferably diethyl ether, and at temperatures between about $20°$ and $50°$ C.

The halohydrin (X) is then converted to the imidazole alcohol (IIa) by treatment with an alkali metal (preferably sodium) salt of imidazole in a polar aprotic solvent such as dimethylformamide at a temperature between about $50°$ and $100°$ C.

Alternatively, treatment of the halohydrin with base will afford the epoxide (III) described in Reaction Sequence A.

When $R^1$ is a monocyclic heteroaromatic ethyl group, the method shown above in Reaction Sequence C is modified as shown below in Reaction Sequence D. This method is also useful for preparing compounds wherein $R^8$ is optionally substituted phenyl or naphthyl.

REACTION SEQUENCE D

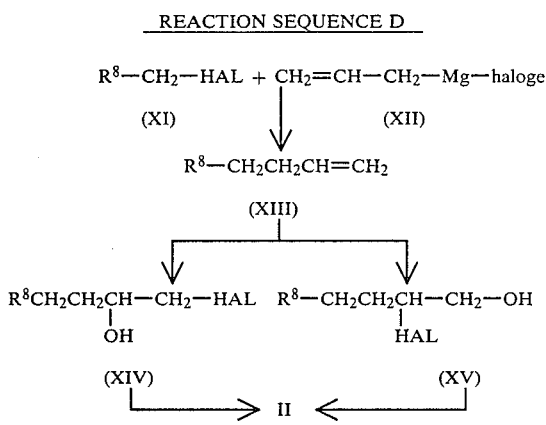

wherein $R^8CH_2CH_2$ is $R^1$ wherein $R^8$ is as previously defined and HAL is chloro or bromo.

In this sequence, the appropriately substituted halomethyl compound (XI) is reacted with an allylmagnesium halide (XII) to give the butene (XIII), which is converted to the corresponding halohydrin (XIV) and/or (XV). The halohydrin is then converted to the imidazole alcohol (II) as described above under Reaction Sequence C. The preparation of (XIII) is carried out in typical solvents for performing Grignard reactions, namely ether-containing solvents, at temperatures between about −20° and 50° C.

The formation of the halohydrin(s) (XIV) and/or (XV) may be carried out by a number of methods known to those skilled in the art, preferably using an N-halo amide, e.g., N-bromosuccinimide, N-bromoacetamide, etc. in an organic solvent such as wet dimethylsulfoxide or a neutral solvent such as dioxane in the presence of an acid catalyst.

When n is 2 compounds of formula (IIb) may be prepared according to a variety of synthetic methods. One convenient method for the preparation of certain compounds of formula (IIb) is shown in reaction sequence E presented below.

REACTION SEQUENCE E

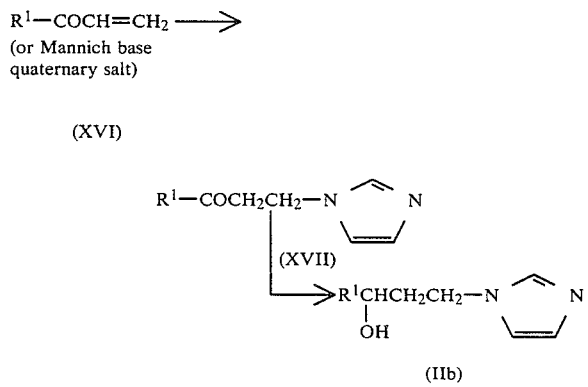

This sequence involves the reaction of imidazole with a vinyl ketone of formula (XVI) (or Mannich base quaternary intermediate) followed by reduction of the resulting keto imidazole of formula (XVII) to the hydroxy imidazole of formula (IIb).

Vinyl ketones of formula (XVI), insofar as they may not be known or generally available, may be prepared by a variety of methods well known in the synthetic organic chemistry art, for example, by the addition of vinyl lithium to the corresponding carboxylic acid; by the addition of vinyl lithium to the corresponding aldehyde followed by oxidation of the allylic alcohol thus produced to the vinyl ketone (e.g., J. Chem Soc. (C), (1966) 1972, J. Chem Soc. (London), (1956) 3070); or by Mannich reaction of the corresponding methyl ketone, quaternization and elimination.

The first step of the conversion, the reaction of vinyl ketone of formula (XVI) to keto imidazole of formula (XVII), is accomplished by contacting the vinyl ketone (or a Mannich quaternary base precursor) with imidazole in an inert organic solvent. The reaction is conveniently carried out utilizing at least a molar amount, and preferably an excess of imidazole relative to vinyl ketone or Mannich quaternary base in an inert organic solvent, for example diethyl ether, dichloromethane or dimethylformamide, at a temperature between about 0° and 40° C. preferably about ambient temperature.

The reduction of the keto imidazole of formula (XVII) to the hydroxy imidazole of formula (IIb) is carried out in the same manner as described above for the conversion of compound of formula (VI) to that of formula (IIa).

When n is 2 or 3 certain compounds of formula (II) are conveniently prepared as illustrated in reaction sequence F presented below.

REACTION SEQUENCE F

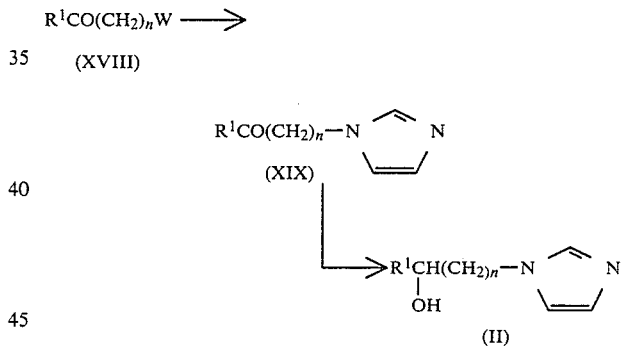

wherein W is chloro, bromo, or iodo and n is 2 or 3.

In this reaction sequence an ω-halo (preferably chloro when n=2) ketone of the formula (XVIII) is converted to the corresponding keto imidazole of formula (XIX) and then to the hydroxy imidazole of formula (II).

The starting m-halo ketones, insofar as they may not be known or generally available, may be suitably prepared by the well-known Friedel-Crafts reaction involving the aromatic hydrocarbon $R^1H$ and an ω-halo acylhalide, or when n=2, by the Friedel-Crafts reaction of $R^1C(O)CL(Br)$ with ethylene to give compound (XVIII) wherein n is 2 and W is chloro (or bromo).

When n is 2, the conversion from compound (XVIII) to compound (XIX) is carried out using imidazole in the same manner as described above for the conversion of (VII)→(VI) in Reaction Sequence B. When n is 3, the reaction temperature is between about 0° and 100° C., preferably between 25° and 80° C.

The reduction of the keto imidazole of formula (XIX) to the hydroxy imidazole of formula (II) is carried out as previously described for the conversion of (VI)→(IIa) in Reaction Sequence B.

Certain compounds of formula (IIc) may also be prepared by an alternate procedure depicted in reaction sequence G.

REACTION SEQUENCE G

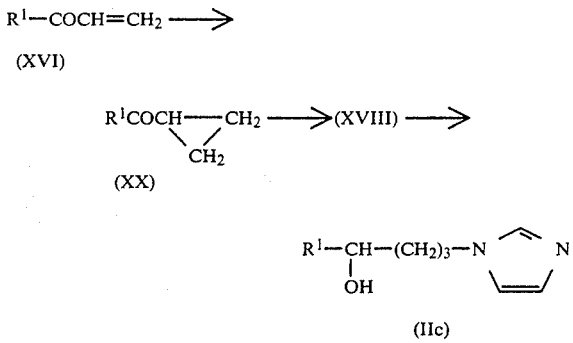

involving the conversion of the previously described vinyl ketone of formula (XVI) to the corresponding cyclopropyl ketone of formula (XX), followed by conversion to the γ-halo ketone of formula (XVIII), n=3, and then, as described above, to the hydroxy imidazole of formula (IIc).

The cyclopropanation of the vinyl ketone of formula (XVI) may be accomplished by methods known per se, for example, as disclosed in J. Am. Chem. Soc., 87, (1965) 1353. The resulting cyclopropyl ketone is then opened to afford the γ-halo ketone by treatment with a hydrohalic acid such as, for example, hydrobromic acid.

In yet another reaction sequence certain compounds of formula (II) wherein n is 1, 2 or 3 may be prepared. This is illustrated below in reaction sequence H:

REACTION SEQUENCE H $R^0-CH=CH_2 +$ (XXI)

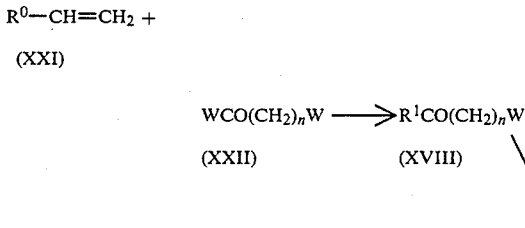

wherein $R^1$ is $R^0CH_2CH_2$ and W is chloro or bromo. This method is applicable in preparing compounds of formula (II) wherein $R^1$ is certain alkyl, cycloalkyl-lower-alkyl, naphthyl lower alkyl, optionally substituted phenyl-lower-alkyl and monocyclic heteroaromatic-lower-alkyl.

In this sequence the ω-halo ketone of formula (XVIII), described above, is prepared starting with a terminal olefin of formula (XXI) and an ω-halo acyl halide of formula (XXI), readily prepared, for example, from the corresponding hydroxyacid.

The compound of formula (XXI) is reacted with the compound of formula (XXII) to afford the halo ketone of the formula (XVIII), which is then converted, as shown above, to the hydroxy imidazole of formula (II). The addition reaction between compounds of formulas (XX) and (XXII) is conveniently carried out under conditions as described in G. Olah, "Friedel Crafts and Related Reactions", Vol. 3, Part 2, Interscience Publishers, New York, (1964).

Compounds of formula (I) may be prepared by reacting compounds of formula (II) or an ester thereof with the intermediate of the following formula

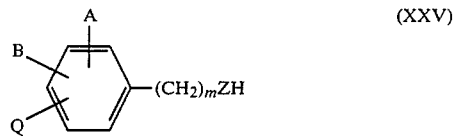

or by converting compounds of formula (I) wherein A, B or C is amino or nitro to the desired group as described infra.

The intermediates of formula (XXV) are readily available from, i.a., Aldrich Chemical Co. or are made by methods well known in the art.

In reacting the above intermediate with compound of formula (II) wherein the intermediate is substituted by a group containing alkylatable nitrogen it is preferred to protect such nitrogens with a protecting group such as, for example, alkanoyl, e.g., acetyl, lower alkoxycarbonyl and the like or by protonation as a salt. Groups containing alkylatable nitrogen are, e.g., amino, monoalkylamino and certain heterocyclic rings containing more than one nitrogen. The protecting groups, if desired, are easily removed by acid hydrolysis, using, for example, hydrochloric acid after reaction with compounds of formula (II).

Compounds of formula (I) wherein m is 0 may be prepared from the compounds of formula (II) by a two-step sequence involving conversion of the hydroxy group of compounds of formula (II) to a suitable leaving group such as a halide (e.g., chloride or bromide) or a sulfonate ester (e.g., methanesulfonate or p-toluenesulfonate) which is then reacted with the appropriate phenol or thiophenol of formula (XXV) optionally in the presence of a base or with a metal salt (preferably an alkali metal salt, e.g., sodium or potassium salt) of the phenol or thiophenol. Alternatively, the reaction may be conducted under phase transfer conditions.

The conversion from the alcohol of formula (II) to the halide or sulfonate ester is carried out by means well known in the art. For example, the alcohol may be halogenated using a halogenating agent such as thionyl chloride or thionyl bromide, either neat, or in an inert organic solvent such as dichloromethane or chloroform, at a temperature between about 0° and 80° C., preferably between about 20° and 80° C. The halogenation reaction may be carried out in the presence of a molar equivalent of a base (e.g., pyridine) if desired. Alternative halogenation procedures include, for example, the use of triphenylphosphine with either carbon tetrachloride, carbon tetrabromide, or N-chloro- or N-bromosuccinimide. When utilizing thionyl chloride or thionyl bromide without the use of added base, the hydrochloride or hydrobromide salt of the corresponding halo compound is produced. This salt may be neutralized (e.g., with potassium carbonate) prior to its use in the alkylation step, or the salt may be used directly if excess phenol or thiophenol salt or base is utilized.

Sulfonate esters may be prepared by the standard procedure of treating the alcohol with at least a stoichiometric amount to approximately a 100% excess (preferably 10%–20% excess) of, for example, methanesulfonyl chloride or p-toluenesulfonyl chloride, in the presence of a base, for example, pyridine or triethylamine. This reaction is carried out at a temperature from about −20° to +50° C., preferably between about 0° and 20° C.

The halide or sulfonate ester prepared as described above, is then treated with the appropriate phenol or thiophenol, optionally in the presence of base, or with a metal salt (preferably an alkali metal salt such as the sodium or potassium salt) of the phenol or thiophenol, in the presence of an inert organic solvent such as acetone, methanol, and the like, at a temperature of about 20° to about 80° C. Alternatively, the halide or sulfonate ester is treated with the appropriate phenol or thiophenol in the mixture of an inert organic solvent such as a chlorinated hydrocarbon (e.g. methylene chloride, chloroform) and an aqueous base such as an aqueous metal hydroxide solution, preferably an alkali metal hydroxide solution in the presence of a quaternary ammonium salt or quaternary phosphonium salt, e.g. tetrabutylammonium bromide. The reaction is carried out with efficient stirring at temperatures between about 0° to 100° C., preferably between about 20° and 80° C.

Compounds of formula (I) wherein Z is S and m is 1, 2 or 3, may be prepared by reacting the above mentioned halide or sulfonate ester with the metal salt, preferably an alkali metal salt such as the sodium or potassium salt, of a compound of formula (XXV) wherein Z is sulfur and m is 1, 2 or 3. This reaction is carried out in an inert organic solvent such as, for example, tetrahydrofuran, diethylether, methanol, and the like. The salt is formed with a strong base such as for example, sodium hydride, sodium amide, sodium methoxide and the like, at a temperature between about 20° and 80° C. Alternatively, the reaction may be performed using the free thiol under phase-transfer conditions as described above.

The compounds of formula (II) are converted to the final products of formula (I) wherein Z is oxygen and m is 1, 2 or 3 by O-alkylation with the appropriate compound of formula (XXV) wherein —ZH is replaced by a leaving group such as halide (chloride, bromide or iodide) or sulfonate ester (e.g., p-toluenesulfonate or methanesulfonate).

The alkylation is carried out by converting the hydroxy group of the compound of formula (II) to a salt such as an alkali metal salt by treatment with a strong base such as, for example, an alkali metal hydride such as sodium hydride; and alkali metal amide such as sodium amide or potassium amide; and the like. This is preferably done in an inert organic solvent such as, for example, dimethylformamide, hexamethylphosphoramide, tetrahydrofuran, and the like. The alkali metal salt is then contacted with the above modified intermediate, preferably in the same solvent system, at a temperature between about 0° and 80° C., most preferably between about 0° and 60° C.

In a preferred reaction certain compounds of formula (I) wherein Z is oxygen and m is 0 may be directly prepared from compounds of formula (II) in one step by reaction with the appropriate phenol in the presence of a triarylphosphine (preferably triphenylphosphine) and a dialkyl azodicarboxylate (preferably dimethyl or diethyl azodicarboxylate). This reaction is preferably carried out in an inert solvent such as an ether (preferably tetrahydrofuran or diethyl ether) a hydrocarbon (preferably benzene or toluene) or dimethylformamide at a temperature between about 0° and 40° C. When compounds of formula (I) are required wherein one or more of A, B or Q is a primary or secondary amino group, it is expedient to use the corresponding acylamino derivative in this reaction, e.g. acetylamino derivative, followed by acid hydrolysis of the acyl derivative of the product compound of formula (I) to give the amino substituted compound of formula (I).

Certain compounds of formula (I) wherein Z is sulfur may also be prepared from compounds of formula (II) by reaction with a tri(loweralkyl)phosphine such as tri(n-butyl)phosphine and the corresponding sulfenimide as described in Tetrahedron Letters, No. 51, pp. 4475–4478 (1977).

Certain compounds of formula (I) wherein n is 1, Z is sulfur and $R^1$ is hydrogen, alkyl, cycloalkyl, cycloalkyl-lower-alkyl, optionally substituted phenyl-lower-alkyl, monocyclic heteroaromatic ring-lower-alkyl or naphthyl-lower-alkyl may also be prepared as depicted in reaction sequence I below.

REACTION SEQUENCE I

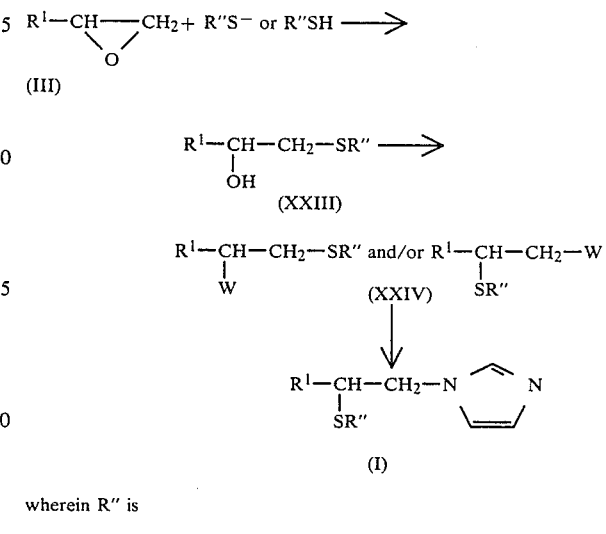

wherein R" is

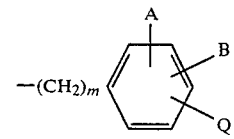

wherein A, B and Q are as defined above and W is a leaving group.

In this sequence the epoxide of formula (III) described earlier, is opened with a thiol or thiophenol or a metal salt thereof, to afford the compound of formula (XXIII). This reaction is carried out utilizing, preferably, an alkali metal salt of the thiol or thiophenol, most preferably the sodium or potassium salt, in an inert organic solvent such as, for example, tetrahydrofuran or acetone at a temperature of between about 0° and 67° C., or using quaternary ammonium salt under phase transfer conditions or the free thiol or thiophenol in the presence of an acid catalyst, e.g., perchloric acid, boron trifluoride in an inert solvent such as dichloromethane or nitromethane, or in the absence of added solvent.

In the next step the hydroxy group of the compound of formula (XXIII) is converted to a leaving group such as a halide (e.g., chloro or bromo) or sulfonate ester (e.g., p-toluensulfonate or methanesulfonate) by treatment with e.g., a halogenating agent such as, for example, thionyl chloride, neat, or preferably in an inert solvent such as dichloromethane, or with, for example, p-toluenesulfonyl chloride, in a solvent such as tetrahydrofuran, dichloromethane and the like. The product of formula (XXIV) may exist in either or both forms depicted and may be interconvertible through or isolatable as an episulfonium intermediate.

In the final step, the compound of formula (XXIV) is converted to the final product of formula (I) by treatment with imidazole. This reaction is carried out in an inert organic solvent such as, for example, acetonitrile, dimethylformamide, and the like, at a temperature of about 0° to about 80° C. Alternatively, the compound of formula (XXIII) or an isomer thereof may be treated with an imidazole derivative such as thionyl bis-(imidazole), etc. to afford the compound of formula (I) directly.

Compounds of formula (I) wherein Q is aminothiocarbonylamino may be prepared from compounds of formula (I) wherein Q is amino by reaction with an isothiocyanate preferably in the presence of a base such as triethylamine in a suitable solvent such as, for example, tetrahydrofuran, dioxane, benzene, methylene chloride and the like.

Compounds of formula (I) wherein Q is aminocarbonylamino may be prepared by reacting compounds of formula (I) wherein Q is amino with an alkyl isocyanate or with an alkali metal isocyanate, e.g., the potassium salt of isocyanate.

The foregoing reaction may be carried out according to art-known methodologies, e.g., by stirring the reactants together, preferably while heating, in an appropriate reaction-inert solvent, e.g., 1,4-dioxane. When $R^5$ stands for hydrogen, it is appropriate to use an appropriate alkali metal cyanate in aqueous medium, the free acid being liberated by the addition thereto of an appropriate acid, e.g., acetic acid.

Compounds of formula (I) wherein Q is lower alkylcarbonylamino can be prepared by acylating an appropriate amine with an appropriate acylating agent according to common N-acylating procedures. Suitable acylating agents which may be used include acyl halides and anhydrides derived from the acid $R^5COOH$ and also the acid itself, the latter being preferred when formylation is desired. In order to prepare compounds wherein Q is lower alkoxycarbonylamino there may be used appropriate carbonohalidates, preferably carbonochloridates, such as methyl chloroformate.

Compounds of formula (I) wherein Q is piperazin-1-yl the 4-position of the ring may be substituted by aminocarbonyl, lower alkylaminocarbonyl and lower alkylaminothiocarbonyl and may be prepared by the procedure described above. The 4-position may also be substituted by lower alkyl, optionally substituted phenyl and optionally substituted benzyl and are prepared by reacting the appropriate reactive ester, such as the halide or sulfonate ester, with an alkylating agent by standard alkylation techniques.

Compounds of formula (I) wherein $NR^2R^3$ is a heterocyclic ring may be prepared by reacting the appropriately substituted intermediate of formula (XXV) with an alcohol of formula (II) as described supra or by reacting a compound of formula (I) with the appropriate cyclizing agent. For example, compounds of formula (I) wherein the above substituent is an optionally substituted imidazolyl, 1,2,3-triazolyl or 1,2,4-triazolyl may be prepared by the methods described in U.S. Pat. No. 4,229,460.

Compounds of formula (I) wherein Q is amino may also be prepared from the nitro compound by reduction using a hydrogenation catalyst such as nickel chloride hexahydrate.

The subject compounds of the instant invention can be isolated as free bases; however, since many of the compounds in base form are oils, it is often more convenient to isolate and characterize the compounds as acid addition salts. These salts are prepared in the usual manner, i.e., by reaction of the base compound with a suitable inorganic or organic acid, described above. Salts formed with dibasic acids (e.g., oxalic acid) may contain one or two molecules of base per molecule of acid. All oxalates described herein contain one molecule of oxalic acid per molecule of imidazole base. If desired, the salts can be readily converted to the free base form by treatment with alkali, such as potassium carbonate, sodium carbonate or sodium or potassium hydroxide.

In summary, another aspect of the present invention relates to a process for preparing compounds of formula (I) which comprises
(a) reacting a compound of the formula

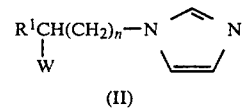
(II)

with

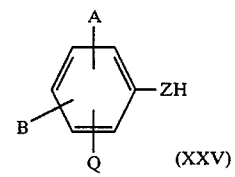
(XXV)

wherein $R^1$, A, B, Q, Z and n are as defined above and W is a leaving group; or
(b) reacting a compound of the formula

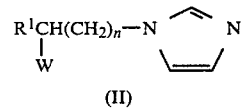
(II)

with

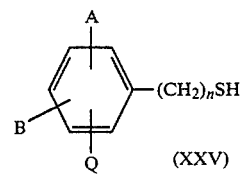
(XXV)

wherein $R^1$, A, B, Q and n are as defined above and m is 1, 2 or 3 and W is a leaving group; or
(c) reacting a compound of the formula

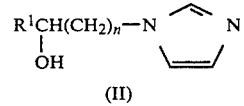
(II)

-continued
with

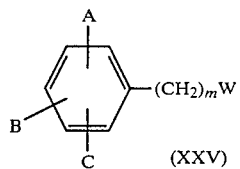

in the presence of a base wherein $R^1$, A, B, C and n are as defined above, m is 1, 2 or 3 and W is a leaving group; or (d) reacting a compound of the formula

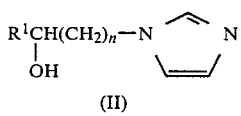

with

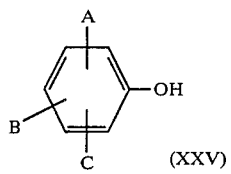

in the presence of a triarylphosphine and a di(alkyl)azodicarboxylate wherein $R^1$, A, B, C and n are as defined above; or (e) reacting a compound of the formula

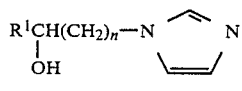

with

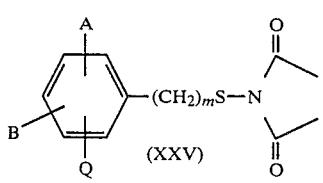

in the presence of a trialkylphosphine wherein $R^1$, A, B, Q, and n are as defined above; or (f) reacting a compound of the formula

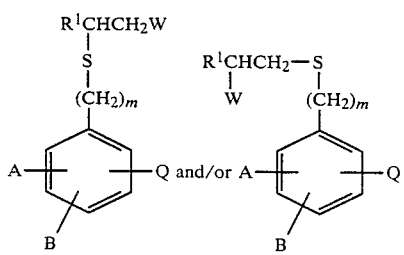

with imidazole wherein A, B and C are as defined above and $R^1$ is hydrogen, alkyl, cycloalkyl optionally substituted by one lower alkyl, cycloalkyl-lower-alkyl optionally substituted phenyl-lower-alkyl, monocyclic heteroaromatic ring-lower-alkyl or naphthyl-lower-alkyl; or (g) reacting a compound of the formula

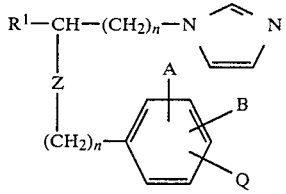

with an isothiocyanate optionally in the presence of a base wherein $R^1$, A, B, m and n are as defined above and $Q^1$ is $NH_2$ or $NHR^4$ to form a compound of formula (I) wherein Q is $NR^4C(S)NR^5$ wherein $R^4$ and $R^5$ are as defined above; or (h) reacting a compound of the formula

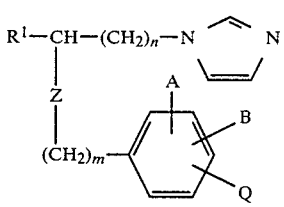

with an isocyanate optionally in the presence of a base wherein $R^1$, A, B, m and n are as defined above and $Q^1$ is $NH_2$ or $NHR^4$ to form a compound of formula (I) wherein Q is $NR^4C(O)NR^5$ wherein $R^4$ and $R^5$ are as defined above; or (i) reacting a compound of the formula

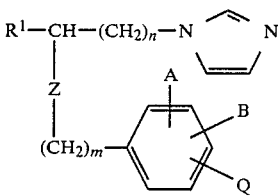

with $R^5C(O)G$ wherein $R^5$ is as defined above and G is a leaving group, $R^1$, A, B, m, n and Z are as defined above and Q is $NH_2$ to form a compound of formula (I) wherein Q is $NR^4C(O)R^5$; or (j) hydrolyzing a compound of the formula

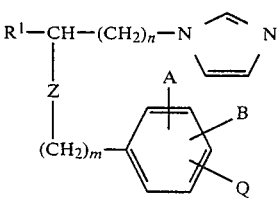

wherein $R^1$, Z, m and n are as defined above and A or B and/or C is $NR^4C(X)YR^5$ wherein X and Y are oxygen or sulfur or Y is a bond and $R^4$ and $R^5$ are as defined above to form a compound of formula (I) wherein Q is $NH_2$ or $NHR^4$; or (k) reducing a compound of the formula

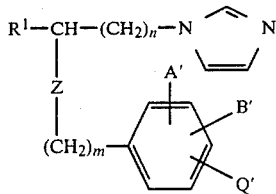

(I)

wherein $R^1$, Z, m and n are as defined above and A' or B' and/or Q' is nitro to form a compound of formula (I) wherein Q is $NH_2$ or $NHR^1$; and (1) converting the free base of formula (I) to an acid addition salt; or (m) converting the acid addition salt to the free base of formula (I); or (n) converting an acid addition salt of formula (I) to another acid addition salt of formula (I).

The following specific examples are illustrative of the present invention and should not be considered as limitative thereof in any manner.

PREPARATION 1

This preparation illustrates the process in Reaction Sequence A.

A. 3-Phenylpropionaldehyde (26.8 g) is added under nitrogen to the ylide prepared from trimethylsulfoxonium iodide (48.4 g) and sodium hydride (55% dispersion in oil; 9.6 g) in dry dimethylsulfoxide (200 ml), according to the procedure in J. Am. Chem. Soc., 84, 867 (1962) and ibid., 87, 1353 (1965). After one hour, the solution was poured into 1 liter of water and the product extracted with ether (3×300 ml.). The extract was washed with water (2×150 ml.) dried ($MgSO_4$) and evaporated to give an oil 1,2-epoxy-4-phenylbutane, used directly in the next step.

The oil from above in 50 ml. of dimethylformamide was treated with imidazole (70 g) and the mixture stirred at 40 C overnight. The resulting solution was poured into a mixture of 700 ml. water and 200 ml. hexane, stirred until crystallization was complete and the product was filtered off as buff granules (28.2 g). Rcrystallization from ethyl acetate gave 1-(2-hydroxy-4-phenylbutyl)imidazole as colorless crystals, m.p. 106°–107° C.

B. Imidazole (40.8 g) in 100 ml of dimethyformamide at room temperature was treated with sodium hydride (4.8 g of 50% dispersion in mineral oil). Once a solution was obtained, 1,2-epoxyoctane (40 g) was added dropwise at room temperature and the resulting mixture placed in an oil bath and warmed to 70° for 6 hours with stirring. The resulting cooled solution was then added to 600 ml of water and extracted with ether (4×400 ml). The combined extracts were washed twice with concentrated aqueous potassium hydroxide, dried ($MgSO_4$) and concentrated. The resulting ethereal solution was stored at 0° and the resulting precipitate filtered to give 45.93 g of 1-(2-hydroxyoctyl)imidazole, m.p. 44°–45.5° C.

Similarly, proceeding as above, substituting the appropriate aldehyde for 3-phenylpropionaldehyde or the appropriate epoxide for 1,2-epoxyoctane, there may be prepared for example, the following compounds of formula (IIa):

1-[2-hydroxy-4-(4-chlorophenyl)butyl]imidazole hydrochloride salt, m.p. 144°–146.5° C.;

1-[2-hydroxy-4-(2,4-dichlorophenyl)butyl]imidazole, m.p. 133°–135° C.;
1-[2-hydroxy-4-(4-tert-butylphenyl)butyl]imidazole;
1-[2-hydroxy-4-(4-fluorophenyl)butyl]imidazole;
1-[2-hydroxy-4-(4-bromophenyl)butyl]imidazole;
1-[2-hydroxy-4-(4-trifluoromethylphenyl)butyl]imidazole;
1-[2-hydroxy-5-(4-chlorophenyl)pentyl]imidazole;
1-[2-hydroxy-4-(2,4-dimethylphenyl)butyl]imidazole;
1-(2-hydroxy-n-butyl)imidazole;
1-(2-hydroxy-n-hexyl)imidazole;
1-(2-hydroxy-n-octyl)imidazole hydrochloride · salt, m.p. 90.5°–93° C.;
1-(2-hydroxy-n-decyl)imidazole;
1-(2-hydroxy-n-tetradecyl)imidazole;
1-(2-hydroxy-2-cyclohexylethyl)imidazole;
1-(2-hydroxy-4-cyclohexylbutyl)imidazole;
1-(2-hydroxy-2-methylcyclohexyl)imidazole;
1-[2-hydroxy-2-(4-methylcyclohexyl)ethyl]imidazole;
1-[2-hydroxy-2-(4-t-butylcyclohexyl)ethyl]imidazole;
1-(2-hydroxyethyl)imidazole;
1-(2-hydroxy-3-methyl-n-butyl)imidazole;
1-(2-hydroxy-4-cyclopentyl-n-butyl)imidazole;
1-[2-hydroxy-4-(4-methylthiophenyl)-n-butyl]imidazole;
1-[2-hydroxy-4-(4-cyanophenyl)-n-butyl]imidazole;
1-[2-hydroxy-4-(4-methoxyphenyl)-n-butyl]imiadazole, m.p. 103°–105° C.;
1-[2-hydroxy-4-(1-naphthyl)-n-butyl]imidazole;
1-[2-hydroxy-4-(2-naphthyl)-n-butyl]imidazole; and
1-[2-hydroxy-4-(4-methylphenyl)-n-butyl]imidazole, m.p. 121.5°–124° C.

PREPARATION 2

This preparation illustrates the process in Reaction Sequence B.

Bromomethyl-t-butyl ketone (17.9 g) (ref. J. Amer. Chem. Soc , 70, 2886 (1948)) was added to a solution of imidazole (34.1 g) in 34 ml of dimethylformamide. After stirring for 1 hour, 600 ml of water was added and the aqueous mixture extracted several times with ethyl acetate. The combined extracts were dried over sodium sulfate, concentrated, and the resulting oil chromatographed on silica gel, eluting with 5% methanol in methylene chloride, to give 3,3-dimethylbutan-2-on-1-yl imidazole.

The ketone prepared as above (21.68 g) in 200 ml of ethanol was cooled to 0° C. and treated with excess sodium tetrahydroborate and stirred for 6 hours. The resulting solution was treated gradually with 40 ml of concentrated hydrochloric acid and the solvent evaporated. The resulting aqueous mixture was treated cautiously with sodium hydroxide (20 g) in 100 ml of water and the resulting mixture extracted with methylene chloride. The extracts were dried over sodium sulphate and evaporated to dryness. Recystallization of the residue from ethyl acetate gave 17.8 g of 1-(3,3-dimethyl-2-hydroxy-n-butyl)imidazole, m.p. 239°–241° C.

PREPARATION 3

This preparation illustrates the process of Reaction Sequence C.

A. A solution of 4-methoxybenzylmagnesium chloride was prepared from 97.2 g of magnesium turnings and 4-methoxybenzyl chloride (32.78 g) in 440 ml ether according to the procedure described in J. Amer. Chem. Soc., 76, 1886 (1954), except that no iodine was used to initiate the reaction. The above solution was decanted under nitrogen into a pressure-equilibrated addition funnel above a flask containing epichlorohydrin (30.5 g) in ether (150 ml), the excess magnesium being washed with ether to ensure complete transfer of the Grignard reagent. The solution of 4-methoxybenzylmagnesium chloride was then added dropwise with stirring under gentle reflux to the epichlorohydrin over about 40 minutes, and stirring and reflux maintained for a further hour. The mixture was allowed to stand overnight. A saturated solution of ammonium chloride was added with stirring until no solid remains, whereupon the ether layer was separated and the aqueous phase re-extracted with ether. The combined extracts were washed with water, dried over MgSO$_4$, evaporated and the residue distilled in vacuo collecting the fraction of bp 140°–141° C. (0.3 mm Hg) to give 27.5 g of 1-chloro-4-(4-methoxyphenyl)-2-butanol as a colorless oil.

B. A solution of sodium, imidazole was prepared by the portionwise addition of sodium hydride (6.77 g of 50% dispersion in mineral oil) to imidazole (10.8 g) in dry dimethylformamide (80 ml) The resulting mixture was treated dropwise with stirring at 50° C. with 1-chloro-4-(4-methoxyphenyl)-2-butanol (27.5 g) and the mixture was stirred overnight at 50° C. and for six hours at 90° C. The mixture was diluted with water (with stirring) to about 250 ml, hexane (50 ml) added whereupon the product started to precipitate. After the addition of water until no further turbidity results, the product was filtered off, washed well with cold water and hexane and dried in air. Recrystallization from ethyl acetate/hexane gave 1-[2-hydroxy-4-(4-methoxyphenyl)-n-butyl]imidazole (21.2 g) as snow-white granules, mp 103°–105° C.

Similarly, procceding as above, substituting the appropriate chlorohydrin for 1-chloro-4-(4-methoxyphenyl)-2-butanol, there are prepared, for example, the following compounds:
1-[2-hydroxy-4-(4-chlorophenyl)-n-butyl]imidazole;
1-[2-hydroxy-4-(4-fluorophenyl)-n-butyl]imidazole;
1-[2-hydroxy-4-(4-methylphenyl)-n-butyl]imidazole;
1-[2-hydroxy-4-(4-t-butylphenyl)-n-butyl]imidazole;
1-[2-hydroxy-4-(2,4-dichlorophenyl)-n-butyl]imidazole; and
1-[2-hydroxy-4-(4-trifluoromethylphenyl)-n-butyl]imidazole.

PREPARATION 4

This preparation illustrates the process of Reaction Sequence D.

A. A solution of allyl magnesium bromide (from 14.6 g of magnesium and 24.2 g (0.2 M) of allyl bromide) in 100 ml ether was added dropwise with stirring to 29.9 g of 5-chloro-2-chloromethylthiophene in 100 ml ether over half an hour and the resulting mixture heated under reflux overnight. The mixture was then poured into 300 ml ice cold dilute sulfuric acid, the ether layer separated and the aqueous phase extracted with 200 ml of ether. The combined ethereal solutions were washed with aqueous potassium carbonate, dried over MgSO$_4$ and evaporated to give crude 4-(5-chlorothien-2-yl)-1-butene as a yellow oil (34 g). B. The crude olefin of step A. in 100 ml dimethyl sulfoxide containing 7.2 g water was cooled to approximately 0° C. and treated with 71.2 g of solid N-bromo-succinimide in small portions over half an hour with efficient stirring. The resulting mixture was stirred overnight at room temperature, poured into 650 ml of water and extracted with ether (600 ml). The combined ethereal extracts were washed, dried over MgSO$_4$ and evaporated to give 38 g of a dark amber oil containing 1-bromo-4-(5-chlorothien-2-yl)-2-butanol and 2-bromo-4-(5-chlorothien-2-yl)-1-butanol.

C. Without purification the product mixture of step B. in 20 ml dimethylformamide was added dropwise to a solution of sodium imidazole (from 3.16 g of 50% dispersion of sodium hydride in mineral oil and 4.8 g of imidazole) in 20 ml dimethylformamide with stirring at room temperature. The mixture was stirred overnight at 80° C., poured into one liter of water and the mixture extracted with ether. After washing and drying over MgSO$_4$, the ether was removed and the residue chromatographed on silica gel eluting with 30% acetone in dichloromethane, followed by acetone to give the pure product. Recrystallization from toluene/hexane afforded 1-[4-(5-chlorothien-2-yl)-2-hydroxy-n-butyl]imidazole,. mp 82°–84.5° C.

In a similar manner are prepared the following:
1-[2-hydroxy-4-(thien-2-yl)-n-butyl]imidazole;
1-[2-hydroxy-4-(thien-3-yl)-n-butyl]imidazole;
1-[2-hydroxy-4-(5-methylthien-2-yl)-n-butyl]imidazole;
1-[2-hydroxy-4-(5-methylfuran-2-yl)-n-butyl]imidazole;
1-[2-hydroxy-4-(furan-2-yl)-n-butyl]imidazole;
1-[2-hydroxy-4-(pyridin-4-yl)butyl]imidazole;
1-[2-hydroxy-2-(pyridin-4-yl)ethyl]imidazole; and
1-[2-hydroxy-2-(pyridin-2-yl)ethyl]imidazole.

PREPARATION 5

This preparation illustrates the process in Reaction Sequence E.

A. 7.0 G of 2,4-dichlorophenyl vinyl ketone (prepared by Jones oxidation of 2,4-dichlorophenyl vinyl carbinol using the general method described in J. Chem. Soc. (C), (1966), 1972) in 350 ml. of anhydrous ether was treated with 3.5 g of imidazole, the solution stirred overnight and then washed with water (3×30 ml.). The solution was dried (MgSO$_4$) and evaporated to give 2,4-dichloro-β-(imidazol-1-yl)propiophenone as an amber gum (8.65 g). The hydrochloride salt may be precipitated from ether and recrystallized from methanol/acetone as colorless rods, m.p. 105.5°–110° C.

B. 13.1 G of 2,4-dichlorobenzoylethyl trimethylammonium iodide (prepared by Mannich reaction of 2,4-dichloroacetophenone with paraformaldehyde and dimethylamine hydrochloride, followed by quaternization with methyl iodide in ether) and 12 g of imidazole in dimethylformamide (50 ml.) was stirred overnight at room temperature and poured into 500 ml. of water. The product was extracted with ether (3×300 ml.), the extracts washed with water (3×75 ml.) and dried. Addition of ethereal hydrogen chloride precipitated the hydrochloride of 2,4-dichloro-β-(imidazol-1-yl)-propiophenone, which was recrystallized from methanol/acetone, m.p. 105°–109° C.

C. The ketone prepared in part A or part B above may be reduced to the corresponding alcohol, 1-[3-hydroxy-3(2,4-dichlorophenyl)propyl]imidazole, m.p. 112°–114.5° C. following the procedure described in Preparation 2.

D. Similarly proceeding as above, substituting the appropriate vinyl ketone or Mannich quaternary salt for those indicated in Part A or B, there may be prepared for example, the following compounds of formula (IIb):
1-[3-hydroxy-4-(4-methoxyphenyl)butyl]imidazole;
1-(3-hydroxyheptyl)imidazole;
1-(3-hydroxyoctyl)imidazole; and
1-(3-hydroxybutyl)imidazole.

PREPARATION 6

This preparation illustrates the process of Reaction Sequence F. A. β-Chloropropiophenone (16.8 g) and imidazole (35 g) in dimethylformamide (25 ml.) were stirred at 0° C. for three hours and poured into 700 ml. water. The product was filtered off as buff flakes (15.9 g) and recrystallized from cyclohexane as colorless flakes of β-(imidazol-1-yl)propiophenone, m.p. 96°–99.5° C.

The above material (5.60 g) in 70 ml. of methanol was treated at 0° C. with excess sodium borohydride. When the reaction was complete, the solvent was evaporated, 100 ml. of water was added and the product (4.90 g) was filtered off. Recrystallization from ethyl acetate gave 1-(3-hydroxy-3-phenylpropyl)imidazole as colorless rods, m.p. 106.5°–108° C.

B. To a 0° C. slurry of 8.24 g of imidazole in 15 ml. dry dimethylformamide was added 5.79 g of p-t-butyl-gamma-chlorobutyrophenone and the mixture was stirred overnight at room temperature, then for one day at 60° C. The above solution was poured into 400 ml. of water and extracted three times with ethyl acetate. The combined extracts were washed with water, dried over magnesium sulfate and the solvent evaporated to afford 5.25 g of 1-[4-(4-t-butylphenyl)butan-4-onyl]imidazole as a golden oil.

To a 0° C. solution of 5.0 g of the above ketone in 150 ml. of anhydrous methanol was added excess sodium borohydride and the mixture stirred for one hour. After removal of the solvent, a small quantity of water was added and the mixture was extracted with ethyl acetate. The combined extracts were dried over magnesium sulfate and evaporated to afford 1-[4-hydroxy-4-(4-t-butylphenyl)butyl]imidazole, which was converted to the oxalate salt and recrystallized from ethyl acetate/ethanol, m.p. 205°–207° C.(foaming).

Similarly, proceeding as above, substituiting the appropriate haloketone for those indicated in part A or B, there may be prepared, for example, the first four compounds of formula (IIb) listed in Preparation 3, as well as the following compounds of formula (II):

1-[4-hydroxy-4-(2,4-dichlorophenyl)butyl]imidazole;
1-[4-hydroxy-5-(4-chlorophenyl)pentyl]imidazole;
1-[4-hydroxy-5-(4-methoxyphenyl)pentyl]imidazole;
1-(4-hydroxypentyl)imidazole;
1-(4-hydroxyoctyl)imidazole; and
1-(4-hydroxynonyl)imidazole.

PREPARATION 7

A mixture of 1-[4-(4-chlorophenyl)-2-hydroxy-n-butyl]imidazole (20 g) in dry pyridine (100 ml) was cooled in an ice bath and treated dropwise with stirring with 7.0 ml of methanesulfonyl chloride. The mixture was allowed to come to room temperature overnight and diluted to 500 ml by the addition of ethyl acetate, with stirring. The resulting solid was then filtered off, washed with acetone and dried in air to give 1-[4-(4-chlorophenyl)-2-(methanesulfonyloxy)-n-butyl-]imidazole hydrochloride as a white solid (27.4 g).

Similarly, proceeding as above substituting the appropriate compound of formula (II) for 1-[4-(4-chlorophenyl)-2-hydroxy-n-butyl]imidazole hydrochloride, the salts of the following compounds are prepared:
1-[2-(2,4-dichlorophenyl)-2-(methanesulfonyloxyethyl]-imidazole;
1-[4-(2,4-dichlorophenyl)-2-(methanesulfonyloxy)-n-butyl]imidazole;
1-[4-(4-methylphenyl)-2-(methanesulfonyloxy)-n-butyl]imidazole;
1-[4-(4-fluorophenyl)-2-(methanesulfonyloxy)-n-butyl]imidazole;
1-[4-phenyl-2-(methanesulfonyloxy)-n-butyl]imidazole;
1-[4-(1-naphthyl)-2-(methanesulfonyloxy)-n-butyl]imidazole;
1-[4-(2-naphthyl)-2-(methanesulfonyloxy)-n-butyl]imidazole;
1-[4-thien-2-yl-2-(methanesulfonyloxy)-n-butyl]imidazole;
1-[4-(5-chlorothien-2-yl)-2-(methanesulfonyloxy)-n-butyl]imidazole;
1-[4-(5-methylthien-2-yl)-2-(methanesulfonyloxy)-n-butyl]imidazole;
1-[4-furan-2-yl-2-(methanesulfonyloxy)-n-butyl]imidazole;
1-[4-(5-methylfuran-2-yl)-2-(methanesulfonyloxy)-n-butyl]imidazole;
1-[4-pyridin-4-yl-2-(methanesulfonyloxy)-n-butyl]imidazole;
1-[4-cyclopentyl-2-(methanesulfonyloxy)-n-butyl]imidazole;
1-[4-(4-methylthiophenyl)-2-(methanesulfonyloxy)-n-butyl]imidazole;
1-[4-(4-cyanophenyl)-2-(methanesulfonyloxy)-n-butyl]imidazole;
1-[4-(4-trifluoromethylphenyl)-2-(methanesulfonyloxy)-n-butyl]imidazole;
1-[4-(4-t-butylphenyl)-2-(methanesulfonyloxy)-n-butyl]imidazole;
1-[4-(4-bromophenyl)-2-(methanesulfonyloxy)-n-butyl]imidazole;
1-[4-(2,4-dimethylphenyl)-2-(methanesulfonyloxy)-n-butyl]imidazole;
1-[4-thien-3-yl-2-(methanesulfonyloxy)-n-butyl]imidazole;
1-(2-methanesulfonyloxy-n-butyl)imidazole;
1-(2-methanesulfonyloxy-n-hexyl)imidazole;
1-(2-methanesulfonyloxy-n-octyl)imidazole;
1-(2-methanesulfonyloxy-n-decyl)imidazole;
1-(2-methanesulfonyloxy-n-tetradecyl)imidazole;
1-(2-methanesulfonyloxy-3-methyl-n-butyl)imidazole;
1-[5-(4-chlorophenyl)-3-methanesulfonyloxy-n-pentyl]imidazole;
1-[6-(4-chlorophenyl)-4-methanesulfonyloxy-n-hexyl]imidazole;
1-(2-cyclohexyl-2-methanesulfonyloxyethyl)imidazole;
1-(4-cyclohexyl-2-methanesulfonyloxy-n-butyl)imidazole;
1-[4-(2-methylcyclohexyl)-2-(methanesulfonyloxy)-n-butyl]imidazole;
1-[4-(4-methylcyclohexyl)-2-(methanesulfonyloxy)-n-butyl]imidazole;
1-[4-(4-t-butylcyclohexyl)-2-(methanesulfonyloxy)-n-butyl]imidazole;
1-[3-(4-chlorophenyl)-2-(methanesulfonyloxy)-n-propyl]imidazole;
1-[5-(4-chlorophenyl)-2-(methanesulfonyloxy)-n-pentyl]imidazole;
1-[3-(pyridin-4-yl)-2-(methanesulfonyloxy)-n-propyl]imidazole;
1-[3-(2,4-dichlorophenyl)-3-(methanesulfonyloxy)-n-propyl]imidazole;
1-[4-(2,4-dichlorophenyl)-4-(methanesulfonyloxy)-n-butyl]imidazole;
1-[4-(4-chlorophenyl)-3-(methanesulfonyloxy)-n-butyl]imidazole;

1-[5-(4-chlorophenyl)-4-(methanesulfonyloxy)-n-pentyl]imidazole;
1-[4-(4-methoxyphenyl)-3-(methanesulfonyloxy)-n-butyl]imidazole;
1-[5-(4-methoxyphenyl)-4-(methanesulfonyloxy)-n-pentyl]imidazole;
1-[2-(1-naphthyl)-2-(methanesulfonyloxy)ethyl]imidazole;
1-[3-(1-naphthyl)-3-(methanesulfonyloxy)-n-propyl]imidazole; and
1-[3-(2-naphthyl)-3-(methanesulfonyloxy)-n-propyl]imidazole.

EXAMPLE 1

A. To a solution of diethyl azodicarboxylate (2.68 g) in dry tetrahydrofuran was added 1-[4-(4-chlorophenyl)-2-hydroxy-n-butyl]imidazole (3.28 g) and 4-acetylaminophenol (3.02 g). The mixture was cooled in an ice bath and treated with stirring over five minutes with triphenylphosphine (3.84 g) in 10 ml tetrahydrofuran. The mixture was stirred overnight at room temperature and the solvent evaporated. The residue was chromatographed on silica gel eluting initially with methylene chloride, followed by wet ethyl acetate (2.2% water) to give the pure product as a gum.

This gum was dissolved in ethyl acetate and treated with ethereal hydrogen chloride until precipitation was complete. The precipitated gum was allowed to settle and the ethyl acetate decanted off. The residue was crystallized by the addition of acetone, and was then collected and recrystallized from methanol/acetone and the product dried in vacuo to give 2.18 g of 1-[4-(4-chlorophenyl)-2-(4-acetylaminophenoxy)-n-butyl]imidazole hydrochloride, m.p. 172°–175° C.

B. Similarly, proceeding as above substituting the appropriate phenol for 4-acetylaminophenol the following compounds are prepared:

1-[4-(4-chlorophenyl)-2-(4-formylaminophenoxy)-n-butyl]imidazole;
1-[4-(4-chlorophenyl)-2-(2-acetylaminophenoxy)-n-butyl]imidazole hydrochloride salt, m.p. 151°–152° C.;
1-[4-(4-chlorophenyl)-2-(3-acetylaminophenoxy)-n-butyl]imidazole oxalate salt, m.p. 163°–167° C.;
1-[4-(4-chlorophenyl)-2-(4-propanoylaminophenoxy)-n-butyl]imidazole;
1-[4-(4-chlorophenyl)-2-(4-propylcarbonylaminophenoxy)-n-butyl]imidazole;
1-[4-(4-chlorophenyl)-2-(4-i-propylcarbonylaminophenoxy)-n-butyl]imidazole;
1-[4-(4-chlorophenyl)-2-(4-n-butanoylaminophenoxy)-n-butyl]imidazole;
1-[4-(4-chlorophenyl)-2-(4-n-hexanoylaminophenoxy)-n-butyl]imidazole;
1-[4-(4-chlorophenyl)-2-(4-cyclohexylacetylaminophenoxy)-n-butyl]imidazole;
1-[4-(4-chlorophenyl)-2-(4-cyclohexanoylaminophenoxy)-n-butyl]imidazole;
1-[4-(4-chlorophenyl)-2-(4-benzoylaminophenoxy)-n-butyl]imidazole;
1-[4-(4-chlorophenyl)-2-(4-(4-chlorobenzoylamino)phenoxy)-n-butyl]imidazole;
1-[4-(4-chlorophenyl)-2-(4-(2-methoxybenzoylamino)phenoxy)-n-butyl]imidazole;
1-[4-(4-chlorophenyl)-2-(4-(4-t-butylbenzoylamino)phenoxy)-n-butyl]imidazole;
1-[4-(4-chlorophenyl)-2-(4-phenylacetylaminophenoxy)-n-butyl]imidazole;
1-[4-(4-chlorophenyl)-2-(4-(2-chlorophenylacetylamino)phenoxy)-n-butyl]imidazole;
1-[4-(4-chlorophenyl)-2-(4-(N,N-dimethylamino)phenoxy)-n-butyl]imidazole oxalate salt, m.p. 155°–157° C.;
1-[4-(4-chlorophenyl)-2-(4-(N,N-diethylamino)-phenoxy)-n-butyl]imidazole;
1-[4-(4-chlorophenyl)-2-(3-(N,N-dimethylamino)phenoxy)-n-butyl]imidazole;
1-[4-(4-chlorophenyl)-2-(2-(N,N-dimethylamino)phenoxy)-n-butyl]imidazole;
1-[4-(4-chlorophenyl)-2-(3-(N,N-diethylamino)phenoxy)-n-butyl]imidazole;
1-[4-(4-chlorophenyl)-2-(4-(N,N-dibutylamino)phenoxy)-n-butyl]imidazole;
1-[4-(4-chlorophenyl)-2-(4-(N-butyl-N-methylamino)phenoxy)-n-butyl]imidazole;
1-[4-(4-chlorophenyl)-2-(4-(N-hexyl-N-methylamino)phenoxy)-n-butyl]imidazole;
1-[4-(4-chlorophenyl)-2-(4-(N-cyclohexylmethyl-N-methylamino)phenoxy)-n-butyl]imidazole;
1-[4-(4-chlorophenyl)-2-(4-(N-benzyl-N-methylamino)phenoxy)-n-butyl]imidazole;
1-[4-(4-chlorophenyl)-2-(3-(acetyl-N-methylamino)phenoxy)-n-butyl]imidazole;
1-[4-(4-chlorophenyl)-2-(4-(acetyl-N-methylamino)phenoxy)-n-butyl]imidazole hydrochloride salt, m.p. 229°–231° C.;
1-[4-(4-chlorophenyl)-2-(4-(formyl-N-methylamino)phenoxy)-n-butyl]imidazole;
1-[4-(4-chlorophenyl)-2-(4-(acetyl-N-butylamino)phenoxy)-n-butyl]imidazole;
1-[4-(4-chlorophenyl)-2-(4-(formyl-N-butylamino)phenoxy)-n-butyl]imidazole;
1-[4-(4-chlorophenyl)-2-(4-(n-hexanoyl-N-methylamino)phenoxy)-n-butyl]imidazole;
1-[4-(4-chlorophenyl)-2-(4-benzoyl-N-methylaminophenoxy)-n-butyl]imidazole;
1-[4-(4-chlorophenyl)-2-(4-(2-methoxyphenylcarbonylamino)phenoxy)-n-butyl]imidazole;
1-[4-(4-chlorophenyl)-2-(4-phenylacetyl-N-methylaminophenoxy)-n-butyl]imidazole;
1-[4-(4-chlorophenyl)-2-(4-thioformylaminophenoxy)-n-butyl]imidazole;
1-[4-(4-chlorophenyl)-2-(4-methyl(thiocarbonyl)aminophenoxy)-n-butyl]imidazole hydrogen chloride salt;
UV (MeOH) 220, 293 nm ($\epsilon$ 25,100, 10700).
ir (KBr) 1630, 1240, 1020 cm$^{-1}$.
nmr 2.61 s(CSCH$_3$), 6.90 d, 7.83 d (aromatic). 7.65, 7.89, 9.25 (imidazole ring).
Mass spec m/e 399(m+), 384, 341, 233.
1-[4-(4-chlorophenyl)-2-(4-(n-propyl(thiocarbonyl))amino)phenoxy)-n-butyl]imidazole;
1-[4-(4-chlorophenyl)-2-(4-(n-hexyl(thiocarbonyl))amino)phenoxy)-n-butyl]imidazole;
1-[4-(4-chlorophenyl)-2-(4-methyl(thiocarbonyl)-N-methylaminophenoxy)-n-butyl]imidazole;
1-[4-(4-chlorophenyl)-2-(4-methoxycarbonylaminophenoxy)-n-butyl]imidazole;
1-[4-(4-chlorophenyl)-2-(4-methoxycarbonyl-N-methylaminophenoxy)-n-butyl]imidazole;
1-[4-(4-chlorophenyl)-2-(4-ethoxycarbonylaminophenoxy)-n-butyl]imidazole;
1-[4-(4-chlorophenyl)-2-(4-n-hexyloxycarbonylaminophenoxy)-n-butyl]imidazole;
1-[4-(4-chlorophenyl)-2-(4-phenoxycarbonylaminophenoxy)-n-butyl]imidazole;

1-[4-(4-chlorophenyl)-2-(4-phenylacetylaminophenoxy)-n-butyl]imidazole;
1-[4-(4-chlorophenyl)-2-(4-methylthio(thiocarbonyl)aminophenoxy)-n-butyl]imidazole;
1-[4-(4-chlorophenyl)-2-(4-(methylthio)carbonyl-N-methylaminophenoxy)-n-butyl]imidazole;
1-[4-(4-chlorophenyl)-2-(4-aminocarbonylaminophenoxy)-n-butyl]imidazole;
1-[4-(4-chlorophenyl)-2-(4-(N-methylaminocarbonylamino)phenoxy)-n-butyl]imidazole;
1-[4-(4-chlorophenyl)-2-(4-(N-ethylaminocarbonylamino)phenoxy)-n-butyl]imidazole;
1-[4-(4-chlorophenyl)-2-(4-(N-butylaminocarbonylamino)phenoxy)-n-butyl]imidazole;
1-[4-(4-chlorophenyl)-2-(4-(N-hexylaminocarbonylamino)phenoxy)-n-butyl]imidazole;
1-[4-(4-chlorophenyl)-2-(4-(N-phenylaminocarbonylamino)phenoxy)-n-butyl]imidazole;
1-[4-(4-chlorophenyl)-2-(4-(N,N-dimethylaminocarbonylamino)phenoxy)-n-butyl]imidazole;
1-[4-(4-chlorophenyl)-2-(4-(N,N-dimethylaminocarbonyl-N-methylamino)phenoxy)-n-butyl]imidazole;
1-[4-(4-chlorophenyl)-2-(4-aminocarbonyl-N-butylaminophenoxy)-n-butyl]imidazole;
1-[4-(4-chlorophenyl)-2-(4-aminothiocarbonylaminophenoxy)-n-butyl]imidazole;
1-[4-(4-chlorophenyl)-2-(4-(N-methylaminothiocarbonylamino)phenoxy)-n-butyl]imidazole;
1-[4-(4-chlorophenyl)-2-(4-(N-methylaminothiocarbonylamino)phenoxy)-n-butyl]imidazole;
1-[4-(4-chlorophenyl)-2-(4-(N-n-hexylaminothiocarbonylamino)phenoxy)-n-butyl]imidazole;
1-[4-(4-chlorophenyl)-2-(4-(N-phenylaminothiocarbonylamino)phenoxy)-n-butyl]imidazole;
1-[4-(4-chlorophenyl)-2-(4-(pyrrolidin-1-yl)phenoxy)-n-butyl]imidazole oxalate salt, 125°–127° C.;
1-[4-(4-chlorophenyl)-2-(4-(piperidin-1-yl)phenoxy)-n-butyl]imidazole di(hydrogen chloride) salt;
UV (MeOH) 203, 221, 248 nm ($\epsilon$ 25800, 24000, 6410).
ir (KBr) 1500, 1240 cm$^{-1}$.
nmr (d$_6$DMSO) 2.76(broad ArCH$_2$), 4.64 m (CH$_2$N) 4.91 m (CHO), 7.05 d (phenoxy), 7.99 d (N-phenyl), 7.59, 7.79, 9.29 (imidazole ring.
1-[4-(4-chlorophenyl)-2-(4-(morpholin-1-yl)phenoxy)-n-butyl]imidazole;
1-[4-(4-chlorophenyl)-2-(4-(thiamorpholin-1-yl)phenoxy)-n-butyl]imidazole;
1-[4-(4-chlorophenyl)-2-(4-acetylamino-2,5-dimethylphenoxy)-n-butyl]imidazole;
1-[4-(4-chlorophenyl)-2-(2-methyl-4-acetylaminophenoxy)-n-butyl]imidazole;
1-[4-(4-chlorophenyl)-2-(3-methyl-4-acetylaminophenoxy)-n-butyl]imidazole hydrogen bromide salt, m.p. 152°–160° C. (dec);
1-[4-(4-chlorophenyl)-2-(3-methoxy-4-acetylaminophenoxy)-n-butyl]imidazole;
1-[4-(4-chlorophenyl)-2-(2,6-dichloro-4-acetylaminophenoxy)-n-butyl]imidazole, m.p. 175°–178° C.;
1-[4-(4-chlorophenyl)-2-(2,5-dichloro-4-acetylaminophenoxy)-n-butyl]imidazole;
1-[4-(4-chlorophenyl)-2-(3-chloro-4-acetylaminophenoxy)-n-butyl]imidazole;
1-[4-(4-chlorophenyl)-2-(4-acetylamino-3-nitrophenoxy)-n-butyl]imidazole hydrochloride salt;
UV (MeOH) 221, 224 nm (24700, 24500).
ir (KBr) 1670, 1495, 1250, 1085, 1010, 820 cm$^{-1}$.
nmr (d$_6$DMSO) 2.07(NAc), 4.62 m(CH$_2$N), 4.89(broad CHO) 7.65, 7.82, 9.27 (imidazole ring).
1-[4-(4-chlorophenyl)-2-(2,5-dimethyl-4-acetylaminophenoxy)-n-butyl]imidazole, hydrochloride salt, m.p. 198°–201° C.;
1-[4-(4-chlorophenyl)-2-(3-amino-4-acetylaminophenoxy)-n-butyl]imidazole, di(hydrochloride) salt;
UV (MeOH) 213, 294 nm ($\epsilon$ 39900, 3830).
ir (KBr) 1650, 1500, 1240, 1090, 1020 cm$^{-1}$.
nmr (d$_6$DMSO) 2.11(NAc), 4.62 m(CH$_2$N), 4.73(broad CHO) 7.66, 7.83, 9.32 (imidazole ring).
1-[4-(4-chlorophenyl)-2-[4-piperazin-1-yl)phenoxy]-n-butyl]imidazole;
1-[4-(4-chlorophenyl)-2-[4-(4-methylpiperazin-1-yl)phenoxy]-n-butyl]imidazole;
1-[4-(4-chlorophenyl)-2-[4-(4-ethylpiperazin-1-yl)phenoxy]-n-butyl]imidazole;.
1-[4-(4-chlorophenyl)-2-[4-(4-n-butylpiperazin-1-yl)phenoxy]-n-butyl]imidazole;
1-[4-(4-chlorophenyl)-2-[4-(4-n-butylpiperazin-1-yl)phenoxy]-n-butyl]imidazole;
1-[4-(4-chlorophenyl)-2-[4-(4-phenylpiperazin-1-yl)phenoxy]-n-butyl]imidazole;
1-[4-(4-chlorophenyl)-2-[4-(4-(4-methoxyphenyl)piperazin-1-yl)phenoxy]-n-butyl]imidazole;
1-[4-(4-chlorophenyl)-2-[4-(4-(2,4-dimethylphenyl)piperazin-1-yl)phenoxy]-n-butyl]imidazole;
1-[4-(4-chlorophenyl)-2-[4-(4-(2-chlorophenyl)piperazin-1-yl)phenoxy]-n-butyl]imidazole;
1-[4-(4-chlorophenyl)-2-[4-(4-(4-nitrophenyl)piperazin-1-yl)phenoxy]-n-butyl]imidazole;
1-[4-(4-chlorophenyl)-2-[4-(4-(4-aminophenyl)piperazin-1-yl)phenoxy]-n-butyl]imidazole;
1-[4-(4-chlorophenyl)-2-[4-(4-(4-N-methylaminophenyl)piperazin-1-yl)phenoxy]-n-butyl]imidazole;
1-[4-(4-chlorophenyl)-2-[4-(4-(4-N,N-dimethylaminophenyl)piperazin-1-yl)phenoxy]-n-butyl]imidazole;
1-[4-(4-chlorophenyl)-2-[4-(4-(4-acetylaminophenyl)piperazin-1-yl)phenoxy]-n-butyl]imidazole;
1-[4-(4-chlorophenyl)-2-[4-(4-(4-acetyl-N-methylaminophenyl)piperazin-1-yl)phenoxy]-n-butyl]imidazole;
1-[4-(4-chlorophenyl)-2-[4-(4-benzylpiperazin-1-yl)phenoxy]-n-butyl]imidazole;
1-[4-(4-chlorophenyl)-2-[4-(4-(2,4-dichlorobenzyl)piperazin-1-yl)phenoxy]-n-butyl]imidazole;
1-[4-(4-chlorophenyl)-2-[4-(4-(4-t-butylbenzyl)piperazin-1-yl)phenoxy]-n-butyl]imidazole;
1-[4-(4-chlorophenyl)-2-[4-(4-(4-methylbenzyl)piperazin-1-yl)phenoxy]-n-butyl]imidazole;
1-[4-(4-chlorophenyl)-2-[4-(4-formylpiperazin-1-yl)phenoxy]-n-butyl]imidazole;
1-[4-(4-chlorophenyl)-2-[4-(4-acetylpiperazin-1-yl)phenoxy]-n-butyl]imidazole di(hydrochloride) salt;
UV (MeOH) 247, 277, 298 nm ($\epsilon$ 11500, 1140, 1280).
ir (KBr) 1650, 1260, 850 cm$^{-1}$.
nmr (d$_6$DMSO) 2.09 s(NAc), 9.30 s(imidazole 2 H), 3.44 (broad), 3.98 (broad)piperazine.
1-[4-(4-chlorophenyl)-2-[4-(4-propanoylpiperazin-1-yl)phenoxy]-n-butyl]imidazole;
1-[4-(4-chlorophenyl)-2-[4-(4-hexanoylpiperazin-1-yl)phenoxy]-n-butyl]imidazole;
1-[4-(4-chlorophenyl)-2-[4-(4-benzoylpiperazin-1-yl)phenoxy]-n-butyl]imidazole;
1-[4-(4-chlorophenyl)-2-[4-(4-(4-methoxybenzoyl)piperazin-1-yl)phenoxy]-n-butyl]imidazole;
1-[4-(4-chlorophenyl)-2-[4-(4-(4-methylbenzoyl)piperazin-1-yl)phenoxy]-n-butyl]imidazole;
1-[4-(4-chlorophenyl)-2-[4-(4-(2,4-dichlorobenzoyl)piperazin-1-yl)phenoxy]-n-butyl]imidazole;

1-[4-(4-chlorophenyl)-2-[4-(4-methyl(thiocarbonyl)piperazin-1-yl)phenoxy]-n-butyl]imidazole;

1-[4-(4-chlorophenyl)-2-[4-(4-methylthio(thiocarbonyl)piperazin-1-yl)phenoxy]-n-butyl]imidazole;

1-[4-(4-chlorophenyl)-2-[4-(4-methoxycarbonylpiperazin-1-yl)phenoxy]-n-butyl]imidazole;

1-[4-(4-chlorophenyl)-2-[4-(4-aminocarbonylpiperazin-1-yl)phenoxy]-n-butyl]imidazole;

1-[4-(4-chlorophenyl)-2-[4-(4-aminothiocarbonylpiperazin-1-yl)phenoxy]-n-butyl]imidazole;

1-[4-(4-chlorophenyl)-2-[4-(4-(N-methylamino)carbonylpiperazin-1-yl)phenoxy]-n-butyl]imidazole;

1-[4-(4-chlorophenyl)-2-[4-(4-(N,N-dimethylamino)thiocarbonylpiperazin-1-yl)phenoxy]-n-butyl]imidazole;

1-[4-(4-chlorophenyl)-2-[4-(4-(N-phenylaminocarbonylpiperazin-1-yl)phenoxy]-n-butyl]imidazole;

1-[4-(4-chlorophenyl)-2-[4-(imidazol-1-yl)phenoxy]-n-butyl]imidazole bis(hydrogen disulfate) salt;
UV (MeOH) 220, 242 nm ($\epsilon$ 21310, 13300).
ir (KBr) 1565, 1260, 1060, 850 cm$^{-1}$.
nmr (d$_6$DMSO) 4.60(broad CH$_2$N), 4.97 (broad CHO), 7.87, 8.14, 9.20, 9.34 (imidazole ring).

1-[4-(4-chlorophenyl)-2-[4-(2-methylimidazol-1-yl)phenoxy]-n-butyl]imidazole di(hydrochloride)salt;
nmr (d$_6$DMSO) 2.56 s(CH$_3$), 4.8 m(CH$_2$N and CHO).
mass spec m/e 406(mt), 233, 173, 125.

1-[4-(4-chlorophenyl)-2-[4-(2-ethylimidazol-1-yl)phenoxy]-n-butyl]imidazole di(hydrochloride)salt;
nmr (d$_6$DMSO) 1.22 t(CH$_3$), 1.85 q(CH$_2$CH$_3$), 4.8 m(CH$_2$N and CHO).
mass spec m/e 420(m+), 187, 125.

1-[4-(4-chlorophenyl)-2-[4-(1,2,4-triazol-1-yl)phenoxy]-n-butyl]imidazole oxalate salt, m.p. 80°–84° C.;

1-[4-(4-chlorophenyl)-2-[4-(1,2,4-triazol-4-yl)phenoxy]-n-butyl]imidazole oxalte salt, m.p. 119°–123° C.;

1-[4-(4-chlorophenyl)-2-[4-(pyrazol-1-yl)phenoxy]-n-butyl]imidazole oxalate salt, m.p. 104°–107° C.;

1-[4-(4-chlorophenyl)-2-[4-(1,2,3-triazol-1-yl)phenoxy]-n-butyl]imidazole;

1-[4-(4-chlorophenyl)-2-[4-(1,2,3-triazol-2-yl)phenoxy]-n-butyl]imidazole;

1-[4-(4-chlorophenyl)-2-[4-(2-aminoimidazol-1-yl)phenoxy]-n-butyl]imidazole;

1-[4-(4-chlorophenyl)-2-[4-(2-acetylaminoimidazol-1-yl)phenoxy]-n-butyl]imidazole;

1-[4-(4-chlorophenyl)-2-[4-(2-methylpiperidin-1-yl)phenoxy]-n-butyl]imidazole;

1-[4-(4-chlorophenyl)-2-[4-(2-phenylpyrazin-1-yl)phenoxy]-n-butyl]imidazole;

1-[4-(4-chlorophenyl)-2-[4-(2-oxopyrimidin-1-yl)phenoxy]-n-butyl]imidazole;

1-[4-(4-chlorophenyl)-2-[4-(2-thiono-1,4,5,6-tetrahydropyrimidin-1-yl)phenoxy]-n-butyl]imidazole;

1-[4-(4-chlorophenyl)-2-[4-(6-oxopyridazin-1-yl)phenoxy]-n-butyl]imidazole;

1-[4-(4-chlorophenyl)-2-[4-(6-hydroxypiperazin-1-yl)phenoxy]-n-butyl]imidazole;

1-[4-(4-chlorophenyl)-2-[4-(2-thiono-1,3-oxazin-3-yl)phenoxy]-n-butyl]imidazole;

1-[4-(4-chlorophenyl)-2-[4-(2-iminohexahydro-1,3-oxazin-3-yl)phenoxy]-n-butyl]imidazole;

1-[4-(4-chlorophenyl)-2-[4-(2-acetyliminopyridinyl)phenoxy]-n-butyl]imidazole;

1-[4-(4-chlorophenyl)-2-[4-(3-n-propylaminopyrazol-1-yl)phenoxy]-n-butyl]imidazole;

1-[4-(4-chlorophenyl)-2-[4-(2-i-propylpyrrol-1-yl)phenoxy]-n-butyl]imidazole;

1-[4-(4-chlorophenyl)-2-[4-(2-(4-chlorophenyl)imidazolin-1-yl)phenoxy]-n-butyl]imidazole;

1-[4-(4-chlorophenyl)-2-[4-(2-oxo-1,3-oxazol-3-yl)phenoxy]-n-butyl]imidazole;

1-[4-(4-chlorophenyl)-2-[4-(2-ethylthio-1,3-oxazolin-3-yl)phenoxy]-n-butyl]imidazole;

1-[4-(4-chlorophenyl)-2-[4-(2-imino-1,3-thiazolin-3-yl)phenoxy]-n-butyl]imidazole; and 1-[4-(4-chlorophenyl)-2-[4-(2-oxo-1,3-thiazolidin-3-yl)phenoxy]-n-butyl]imidazole.

C. Similarly, proceeding as above substituting 1-[2-(2,4-dichlorophenyl)-2-hydroxyethyl]imidazole for 1-[4-(4-chlorophenyl)-2-hydroxy-n-butyl]imidazole and substituting the appropriate phenol for 4-acetylaminophenol the following compounds are prepared:

1-[2-(2,4-dichlorophenyl)-2-(3-acetylaminophenoxy)ethyl]imidazole;

1-[2-(2,4-dichlorophenyl)-2-(4-acetylaminophenoxy)ethyl]imidazole hydrochloride salt, m.p. 108°–112° C.;

1-[2-(2,4-dichlorophenyl)-2-(4-propanoylaminophenoxy)ethyl]imidazole;

1-[2-(2,4-dichlorophenyl)-2-(4-butanoylaminophenoxy)ethyl]imidazole;

1-[2-(2,4-dichlorophenyl)-2-(4-(N,N-dimethylamino)phenoxy)ethyl]imidazole;

1-[2-(2,4-dichlorophenyl)-2-(4-(N,N-diethylamino)phenoxy)ethyl]imidazole;

1-[2-(2,4-dichlorophenyl)-2-(2-N,N-dimethylamino)phenoxy)ethyl]imidazole;

1-[2-(2,4-dichlorophenyl)-2-(3-(N,N-dimethylamino)phenoxy)ethyl]imidazole;

1-[2-(2,4-dichlorophenyl)-2-(4-(N-butyl-N-methylamino)phenoxy)ethyl]imidazole;

1-[2-(2,4-dichlorophenyl)-2-(3-acetyl-N-methylaminophenoxy)ethyl]imidazole;

1-[2-(2,4-dichlorophenyl)-2-(4-acetyl-N-methylaminophenoxy)ethyl]imidazole;

1-[2-(2,4-dichlorophenyl)-2-(4-(formyl-N-methylamino)phenoxy)ethyl]imidazole;

1-[2-(2,4-dichlorophenyl)-2-(4-(n-hexanoyl-N-methylamino)phenoxy)ethyl]imidazole;

1-[2-(2,4-dichlorophenyl)-2-(4-(pyrrolidin-1-yl)phenoxy)ethyl]imidazole;

1-[2-(2,4-dichlorophenyl)-2-(4-(piperidin-1-yl)phenoxy)ethyl]imidazole;

1-[2-(2,4-dichlorophenyl)-2-(4-(morpholin-1-yl)phenoxy)ethyl]imidazole;

1-[2-(2,4-dichlorophenyl)-2-(4-(thiamorpholin-1-yl)phenoxy)ethyl]imidazole;

1-[2-(2,4-dichlorophenyl)-2-(3-chloro-4-acetylaminophenoxy)ethyl]imidazole;

1-[2-(2,4-dichlorophenyl)-2-(3-methoxy-4-acetylaminophenoxy)ethyl]imidazole;

1-[2-(2,4-dichlorophenyl)-2-(3-amino-4-acetylaminophenoxy)ethyl]imidazole;

1-[2-(2,4-dichlorophenyl)-2-(3,4-di(acetylamino)phenoxy)ethyl]imidazole;

1-[2-(2,4-dichlorophenyl)-2-[4-(4-methylpiperazin-1yl)phenoxy]ethyl]imidazole;

1-[2-(2,4-dichlorophenyl)-2-[4-(4-phenylpiperazin-1-yl)phenoxy]ethyl]imidazole;

1-[2-(2,4-dichlorophenyl)-2-[4-(4-(4-aminophenyl)piperazin-1-yl)phenoxy]ethyl]imidazole;

1-[2-(2,4-dichlorophenyl)-2-[4-(4-(4-acetylaminophenyl)piperazin-1-yl)phenoxy]ethyl]imidazole;

1-[2-(2,4-dichlorophenyl)-2-[4-(4-formylpiperazin-1-yl)phenoxy]ethyl]imidazole;

1-[2-(2,4-dichlorophenyl)-2-[4-(4-acetylpiperazin-1-yl)phenoxy]ethyl]imidazole;
1-[2-(2,4-dichlorophenyl)-2-[4-(4-propanoylpiperazin-1-yl)phenoxy]ethyl]imidazole;
1-[2-(2,4-dichlorophenyl)-2-[4-(4-benzoylpiperazin-1-yl)phenoxy]ethyl]imidazole;
1-[2-(2,4-dichlorophenyl)-2-[4-(4-methyl(thiocarbonyl)-piperazin-1-yl)phenoxy]ethyl]imidazole;
1-[2-(2,4-dichlorophenyl)-2-[4-(4-methoxycarbonylpiperazin-1-yl)phenoxy]ethyl]imidazole;
1-[2-(2,4-dichlorophenyl)-2-[4-(4-aminocarbonylpiperazin-1-yl)phenoxy]ethyl]imidazole;
1-[2-(2,4-dichlorophenyl)-2-[4-(4-aminothionocarbonylpiperazin-1-yl)phenoxy]ethyl]imidazole;
1-[2-(2,4-dichlorophenyl)-2-[4-(4-(N,N-dimethylaminothiocarbonyl)piperazin-1-yl)phenoxy]ethyl]imidazole;
1-[2-(2,4-dichlorophenyl)-2-[4-(imidazol-1-yl)phenoxy]ethyl]imidazole;
1-[2-(2,4-dichlorophenyl)-2-[4-(2-methylimidazol1-yl)phenoxy]ethyl]imidazole;
1-[2-(2,4-dichlorophenyl)-2-[4-(2-ethylimidazol-1-yl)phenoxy]ethyl]imidazole;
1-[2-(2,4-dichlorophenyl)-2-[4-(1,2,4-triazol-1-yl)phenoxy]ethyl]imidazole;
1-[2-(2,4-dichlorophenyl)-2-[4-(1,2,4-triazol-4-yl)phenoxy]ethyl]imidazole;
1-[2-(2,4-dichlorophenyl)-2-[4-(pyrazol-1-yl)phenoxy]ethyl]imidazole;
1-[2-(2,4-dichlorophenyl)-2-[4-(1,2,3-triazol-1-yl)phenoxy]ethyl]imidazole;
1-[2-(2,4-dichlorophenyl)-2-[4-(1,2,3-triazol-2-yl)phenoxy]ethyl]imidazole;

D. Similarly, proceeding as above substituting the appropriate compound of formula (II) for 1-[4-(4-chlorophenyl)-2-hydroxy-n-butyl]imidazole and the appropriate phenol for 4-acetylaminophenol the following compounds are prepared:

1-[4-(4-methoxyphenyl)-2-(4-acetylaminophenoxy)-n-butyl]imidazole hydrochloride salt, m.p. 190°–193° C.;
1-[4-(4-methoxyphenyl)-2-(4-formylaminophenoxy)-n-butyl]imidazole;
1-[4-(4-methoxyphenyl)-2-(4-(imidazol-1-yl)phenoxy)-n-butyl]imidazole;
1-[4-(4-methoxyphenyl)-2-(4-(4-formylpiperazin-1-yl)phenoxy)-n-butyl]imidazole;
1-[4-(4-methoxyphenyl)-2-(4-(4-acetylpiperazin-1-yl)phenoxy)-n-butyl]imidazole;
1-[4-(4-methoxyphenyl)-2-(4-(pyrrolidin-1-yl)phenoxy)-n-butyl]imidazole;
1-[4-(2,4-dichlorophenyl)-2-(4-acetylaminophenoxy)-n-butyl]imidazole;
1-[4-(2,4-dichlorophenyl)-2-(4-formylaminophenoxy)-n-butyl]imidazole;
1-[4-(2,4-dichlorophenyl)-2-(4-(imidazol-1-yl)phenoxy)-n-butyl]imidazole;
1-[4-(2,4-dichlorophenyl)-2-(4-(4-formylpiperazin-1-yl)phenoxy)-n-butyl]imidazole;
1-[4-(2,4-dichlorophenyl)-2-(4-(4-acetylpiperazin-1-yl)phenoxy)-n-butyl]imidazole;
1-[4-(2,4-dichlorophenyl)-2-(4-(pyrrolidin-1-yl)phenoxy)-n-butyl]imidazole;
1-[4-(4-methylphenyl)-2-(4-acetylaminophenoxy)-n-butyl]imidazole;
1-[4-(4-methylphenyl)-2-(4-formylaminophenoxy)-n-butyl]imidazole;
1-[4-(4-methylphenyl)-2-(4-(imidazol-1-yl)phenoxy)-n-butyl]imidazole;
1-[4-(4-methylphenyl)-2-(4-(4-formylpiperazin-1-yl)phenoxy)-n-butyl]imidazole;
1-[4-(4-methylphenyl)-2-(4-(4-acetylpiperazin-1-yl)phenoxy)-n-butyl]imidazole;
1-[4-(4-methylphenyl)-2-(4-(pyrrolidin-1-yl)phenoxy)-n-butyl]imidazole;
1-[4-phenyl-2-(4-acetylaminophenoxy)-n-butyl]imidazole;
1-[4-phenyl-2-(4-formylaminophenoxy)-n-butyl]imidazole;
1-[4-phenyl-2-(4-(imidazol-1-yl)phenoxy)-n-butyl]imidazole;
1-[4-phenyl-2-(4-(4-formylpiperazin-1-yl)phenoxy)-n-butyl]imidazole;
1-[4-phenyl-2-(4-(4-acetylpiperazin-1-yl)phenoxy)-n-butyl]imidazole;
1-[4-phenyl-2-(4-(pyrrolidin-1-yl)phenoxy)-n-butyl]imidazole;
1-[4-(4-fluorophenyl)-2-(4-acetylaminophenoxy)-n-butyl]imidazole;
1-[4-(4-fluorophenyl)-2-(4-formylaminophenoxy)-n-butyl]imidazole;
1-[4-(4-fluorophenyl)-2-(4-(imidazol-1-yl)phenoxy)-n-butyl]imidazole;
1-[4-(4-fluorophenyl)-2-(4-(4-formylpiperazin-1-yl)phenoxy)-n-butyl]imidazole;
1-[4-(4-fluorophenyl)-2-(4-(4-acetylpiperazin-1-yl)phenoxy)-n-butyl]imidazole;
1-[4-(4-fluorophenyl)-2-(4-(pyrrolidin-1-yl)phenoxy)-n-butyl]imidazole;
1-[4-(1-naphthyl)-2-(4-acetylaminophenoxy)-n-butyl]imidazole;
1-[4-(1-naphthyl)-2-(4-formylaminophenoxy)-n-butyl]imidazole;
1-[4-(1-naphthyl)-2-(4-(imidazol-1-yl)phenoxy)-n-butyl]imidazole;
1-[4-(1-naphthyl)-2-(4-(4-formylpiperazin-1-yl)phenoxy)-n-butyl]imidazole;
1-[4-(1-naphthyl)-2-(4-(4-acetyl-piperazin-1-yl)phenoxy)-n-butyl]imidazole;
1-[4-(1-naphthyl)-2-(4-(pyrrolidin-1-yl)phenoxy)-n-butyl]imidazole;
1-[4-(2-naphthyl)-2-(4acetylaminophenoxy)-n-butyl]imidazole;
1-[4-(2-naphthyl)-2-(4-formylaminophenoxy)-n-butyl]imidazole;
1-[4-(2-naphthyl)-2-(4-(imidazol-1-yl)phenoxy)-n-butyl]imidazole;
1-[4-(2-naphthyl)-2-(4-(4-formylpiperazin-1-yl)phenoxy)-n-butyl]imidazole;
1-[4-(2-naphthyl)-2-(4-(4-acetylpiperazin-1-yl)phenoxy)-n-butyl]imidazole;
1-[4-(2-naphthyl)-2-(4-(pyrrolidin-1-yl)phenoxy)-n-butyl]imidazole;
1-[4-(thien-2-yl)-2-(4-acetylaminophenoxy)-n-butyl]imidazole;
1-[4-(thien-2-yl)-2-(4-formylaminophenoxy)-n-butyl]imidazole;
1-[4-(thien-2-yl)-2-(4-(imidazol-1-yl)phenoxy)-n-butyl]imidazole;
1-[4-(thien-2-yl)-2-(4-(4-formylpiperazin-1-yl)phenoxy)-n-butyl]imidazole;
1-[4-(thien-2-yl)-2-(4-(4-acetylpiperazin-1-yl)phenoxy)-n-butyl]imidazole;
1-[4-(thien-2-yl)-2-(4-(pyrrolidin-1-yl)phenoxy)-n-butyl]imidazole;

1-[4-(5-chlorothien-2-yl)-2-(4-acetylaminophenoxy)-n-butyl]imidazole;
1-[4-(5-chlorothien-2-yl)-2-(4-formylaminophenoxy)-n-butyl]imidazole;
1-[4-(5-chlorothien-2-yl)-2-(4-(imidazol-1-yl)phenoxy)-n-butyl]imidazole;
1-[4-(5-chlorothien-2-yl)-2-(4-(4-formylpiperazin-1-yl)phenoxy)-n-butyl]imidazole;
1-[4-(5-chlorothien-2-yl)-2-(4-(4-acetylpiperazin-1-yl)phenoxy)-n-butyl]imidazole;
1-[4-(5-chlorothien-2-yl)-2-(4-(pyrrolidin-1-yl)phenoxy)-n-butyl]imidazole;
1-[4-(5-methylthien-2-yl)-2-(4-acetylaminophenoxy)-n-butyl]imidazole;
1-[4-(5-methylthien-2-yl)-2-(4-formylaminophenoxy)-n-butyl]imidazole;
1-[4-(5-methylthien-2-yl)-2-(4-(imidazol-1-yl)phenoxy)-n-butyl]imidazole;
1-[4-(5-methylthien-2-yl)-2-(4-(4-formylpiperazin-1-yl)phenoxy)-n-butyl]imidazole;
1-[4-(5-methylthien-2-yl)-2-(4-(4-acetylpiperazin-1-yl)phenoxy)-n-butyl]imidazole;
1-[4-(5-methylthien-2-yl)-2-(4-(pyrrolidin-1-yl)phenoxy)-n-butyl]imidazole;
1-[4-(furan-2-yl)-2-(4-acetylaminophenoxy)-n-butyl]imidazole;
1-[4-(furan-2-yl)-2-(4-formylaminophenoxy)-n-butyl]imidazole;
1-[4-(furan-2-yl)-2-(4-(imidazol-1-yl)phenoxy)-n-butyl]imidazole;
1-[4-(furan-2-yl)-2-(4-(4-formylpiperazin-1-yl)phenoxy)-n-butyl]imidazole;
1-[4-(furan-2-yl)-2-(4-(4-acetylpiperazin-1-yl)phenoxy)-n-butyl]imidazole;
1-[4-(furan-2-yl)-2-(4-(pyrrolidin-1-yl)phenoxy)-n-butyl]imidazole;
1-[4-(5-methylfuran-2-yl)-2-(4-acetylaminophenoxy)-n-butyl]imidazole;
1-[4-(5-methylfuran-2-yl)-2-(4-formylaminophenoxy)-n-butyl]imidazole; 1-[4-(5-methylfuran-2-yl)-2-(4-(imidazol-1-yl)phenoxy)-n-butyl]imidazole;
1-[4-(5-methylfuran-2-yl)-2-(4-(4-formylpiperazin-1-yl)phenoxy)-n-butyl]imidazole;
1-[4-(5-methylfuran-2-yl)-2-(4-(4-acetylpiperazin-1-yl)phenoxy)-n-butyl]imidazole;
1-[4-(5-methylfuran-2-yl)-2-(4-(pyrrolidin-1-yl)phenoxy)-n-butyl]imidazole;
1-[4-(pyridin-4-yl)-2-(4-acetylaminophenoxy)-n-butyl]imidazole;
1-[4-(pyridin-4-yl-)2-(4-formylaminophenoxy)-n-butyl]imidazole;
1-[4-(pyridin-4-yl)-2-(4-imidazol-1-yl)phenoxy)-n-butyl]imidazole;
1-[4-(pyridin-4-yl)-2-(4-(4-formylpiperazin-1-yl)phenoxy)-n-butyl]imidazole;
1-[4-(pyridin-4-yl)-2-(4-(4-acetylpiperazin-1-yl)phenoxy)-n-butyl]imidazole;
1-[4-(pyridin-4-yl)-2-(4-(pyrrolidin-1-yl)phenoxy)-n-butyl]imidazole;
1-[2-(4-acetylaminophenoxy)-n-butyl]imidazole;
1-[2-(4-acetylaminophenoxy)-n-hexyl]imidazole;
1-[2-(4-acetylaminophenoxy)-n-octyl]imidazole oxalate salt, m.p. 94°–97.5° C.;
1-[2-(4-acetylaminophenoxy)-n-decyl]imidazole;
1-[2-(4-acetylaminophenoxy)-n-tetradecyl]imidazole;
1-[2-cyclohexyl-2-(4-acetylaminophenoxy)ethyl]imidazole;
1-[4-cyclohexyl-2-(4-acetylaminophenoxy)-n-butyl]imidazole;
1-[2-(4-methylcyclohexyl)-2-(4-acetylaminophenoxy)ethyl]imidazole;
1-[2-(2-methylcyclohexyl)-2-(4-acetylaminophenoxy)ethyl]imidazole;
1-[2-(4-t-butylcyclohexyl)-2-(4-acetylaminophenoxy)ethyl]imidazole;
1-[3-(4-chlorophenyl)-2-(4-acetylaminophenoxy)-n-propyl]imidazole;
1-[2-(2,4-dichlorophenyl)-2-(4-(imidazol-1-yl)phenoxy)ethyl]imidazole, di(hydrochloride) salt, m.p. 145°–146° C. (dec);
1-[5-(4-chlorophenyl)-2-(4-acetylaminophenoxy)-n-pentyl]imidazole;
1-[2-(4-pyridinyl)-2-(4-acetylaminophenoxy)ethyl]imidazole;
1-[2-(2-pyridinyl)-2-(4-acetylaminophenoxy)ethyl]imidazole;
1-[3-(2,4-dichlorophenyl)-3-(4-acetylaminophenoxy)n-propyl]imidazole;
1-[4-(4-chlorophenyl)-3-(4-acetylaminophenoxy)-n-butyl]imidazole;
1-[4-(4-methoxyphenyl)-3-(4-acetylaminophenoxy)n-butyl]imidazole;
1-[3-(4-acetylaminophenoxy)-n-butyl]imidazole;
1-[3-(4-acetylaminophenoxy)-n-heptyl]-imidazole;
1-[3-(4-acetylaminophenoxy)-n-octyl]imidazole;
1-[4-(2,4-dichlorophenyl)-4-(4-acetylaminophenoxy)-n-butyl]imidazole;
1-[5-(4-chlorophenyl)-4-(4-acetylaminophenoxy)-n-pentyl]imidazole;
1-[4-(4-acetylaminophenoxy)-n-pentyl]imidazole;
1-[4-(4-acetylaminophenoxy)-n-octyl]imidazole;
1-[4-(4-acetylaminophenoxy)-n-nonyl]imidazole;
1-[2-(4-acetylaminophenoxy)ethyl]imidazole;
1-[2-(4-acetylaminophenoxy)-3-methyl-n-butyl]imidazole;
1-[4-cyclopentyl-2-(4-acetylaminophenoxy)-n-butyl]imidazole;
1-[4-(4-methylthiophenyl)-2-(4-acetylaminophenoxy)-n-butyl]imidazole;
1-[4-(4-cyanophenyl)-2-(4-acetylaminophenoxy)-n-butyl]imidazole;
1-[4-(4-trifluoromethylphenyl)-2-(4-acetylaminophenoxy)-n-butyl]imidazole;
1-[4-(4-t-butylphenyl)-2-(4-acetylaminophenoxy)-n-butyl]imidazole;
1-[4-(4-bromophenyl)-2-(4-acetylaminophenoxy)-n-butyl]imidazole;
1-[4-(2,4-dimethylphenyl)-2-(4-acetylaminophenoxy)-n-butyl]imidazole;
1-[5-(4-chlorophenyl)-3-(4-acetylaminophenoxy)-n-pentyl]imidazole;
1-[6-(4-chlorophenyl)-4-(4-acetylaminophenoxy)-n-hexyl]imidazole;
1-[4-thien-3-yl)-2-(4-acetylaminophenoxy)-n-butyl]imidazole;
1-[2-(1-naphthyl)-2-(4-acetylaminophenoxy)ethyl]imidazole;
1-[3-(1-naphthyl)-3-(4-acetylaminophenoxy)-n-propyl]imidazole; and
1-[3-(2-naphthyl)-3-(4-acetylaminophenoxy)-n-propyl]imidazole.

EXAMPLE 2

A. A mixture of 1-[4-(4-chlorophenyl)-2-methanesulfonyloxy-n-butyl]imidazole hydrochloride (2.0 g), 4- acetylaminothiophenol (1.2 g) and anhydrous potassium carbonate (2.0 g) in 30 ml of acetone and 10 ml of methanol was stirred and refluxed overnight under nitrogen. The solvent was evaporated and the residue treated with water (50 ml) and ether (20 ml) and the mixture stirred until crystallization was complete. Filtration of the product and recrystallization from ethyl acetate gave 1.84 g of 1-[4-(4-chlorophenyl)-2-(4-acetylaminophenylthio)-n-butyl]imidazole as a pale cream solid, m.p. 165.5°–166.5° C. B. Similarly, proceeding as above substituting the appropriate thiophenol for 4-acetylaminothiophenol the following compounds are prepared:

1-[4-(4-chlorophenyl)-2-(2-aminophenylthio)-n-butyl]imidazole di(hydrochloride)salt;
UV(MeOH) 209, 277, 306 nm($\epsilon$34000, 1190, 3220).
ir(KBr) 1090, 1015, 760 cm$^{-1}$.
nmr 3.81(broad CHS), 4.53 m(CH$_2$N), 7.64s, 7.90s, 9.40s(imidazole).

1-[4-(4-chlorophenyl)-2-(3-aminophenylthio)-n-butyl]imidazole, m.p. 89°–91° C.;

1-[4-(4-chlorophenyl)-2-(4-aminophenylthio)-n-butyl]imidazole, m.p. 104.4°–105.5° C.;

1-[4-(4-chlorophenyl)-2-(4-formylaminophenylthio)-n-butyl]imidazole;

1-[4-(4-chlorophenyl)-2-(2-acetylaminophenylthio)-n-butyl]imidazole, m.p. 91°–94° C.;

1-[4-(4-chlorophenyl)-2-(3-acetylaminophenylthio)-n-butyl]imidazole hydrochloride salt;
UV(MeOH) 220, 244, ($\epsilon$26900, 18600).
ir(KBr) 1585, 1535, 1090, 1015 cm$^{-1}$.
nmr(d$_6$DMSO)2.10(NAc), 3.64(broad CHS), 4.46dq(CH$_2$N), 7.61s, 7.81s, 9.30s .

b 1-[4-(4-chlorophenyl)-2-(4-butanoylaminophenylthio)-n-butyl]imidazole;

1-[4-(4-chlorophenyl)-2-(4-hexanoylaminophenylthio)-n-butyl]imidazole;

1-[4-(4-chlorophenyl)-2-(4-(4-methoxyphenylacetylamino)phenylthio)-n-butyl]imidazole;

1-[4-(4-chlorophenyl)-2-(4-(4-trifluoromethylbenzoylamino)phenylthio)-n-butyl]imidazole;

1-[4-(4-chlorophenyl)-2-(4-(2,4-dichlorobenzoylamino)phenylthio)-n-butyl]imidazole;

1-[4-(4-chlorophenyl)-2-(4-(N-methylamino)phenylthio)-n-butyl]imidazole;

1-[4-(4-chlorophenyl)-2-(4-(N-i-propylamino)phenylthio)-n-butyl]imidazole;

1-[4-(4-chlorophenyl)-2-(4-(N-phenylamino)phenylthio)-n-butyl]imidazole;

1-[4-(4-chlorophenyl)-2-(4-(N,N-dimethylamino)phenylthio)-n-butyl]imidazole;

1-[4-(4-chlorophenyl)-2-(4-(N,N-diethylamino)phenylthio)-n-butyl]imidazole;

1-[4-(4-chlorophenyl)-2-(4-(N-n-hexyl-N-methylamino)phenylthio)-n-butyl]imidazole;

1-[4-(4-chlorophenyl)-2-(4-(acetyl-N-methylamino)phenylthio)-n-butyl]imidazole;

1-[4-(4-chlorophenyl)-2-(4-acetyl-N-butylamino)phenylthio)-n-butyl]imidazole;

1-[4-(4-chlorophenyl)-2-(4-thioformylaminophenylthio)-n-butyl]imidazole;

1-[4-(4-chlorophenyl)-2-(4-methyl(thiocarbonyl)aminophenylthio)-n-butyl]imidazole;

1-[4-(4-chlorophenyl)-2-(4-methoxycarbonylaminophenylthio)-n-butyl]imidazole;

1-[4-(4-chlorophenyl)-2-(4-aminocarbonylaminophenylthio)-n-butyl]imidazole;

1-[4-(4-chlorophenyl)-2-(4-(N-ethylaminocarbonylamino)phenylthio)-n-butyl]imidazole;

1-[4-(4-chlorophenyl)-2-(4-aminothiocarbonylaminophenylthio)-n-butyl]imidazole;

1-[4-(4-chlorophenyl)-2-(4-(N-methylaminothiocarbonylamino)phenylthio)-n-butyl]imidazole;

1-[4-(4-chlorophenyl)-2-(4-(N-phenylaminothiocarbonylamino)phenylthio)-n-butyl]imidazole;

1-[4-(4-chlorophenyl)-2-(4-(pyrrolidin-1-yl)phenylthio)-n-butyl]imidazole;

1-[4-(4-chlorophenyl)-2-(4-(piperidin-1-yl)phenylthio)-n-butyl]imidazole;

1-[4-(4-chlorophenyl)-2-(4-(morpholin-1-yl)phenylthio)-n-butyl]imidazole;

1-[4-(4-chlorophenyl)-2-(4-amino-3-methylphenylthio)-n-butyl]imidazole;

1-[4-(4-chlorophenyl)-2-(3-methyl-4-acetylaminophenylthio)-n-butyl]imidazole;

1-[4-(4-chlorophenyl)-2-(4-amino-3-chlorophenylthio)-n-butyl]imidazole;

1-[4-(4-chlorophenyl)-2-(3-chloro-4-acetylaminophenylthio)-n-butyl]imidazole;

1-[4-(4-chlorophenyl)-2-(4-amino-3-methoxyphenylthio)-n-butyl]imidazole;

1-[4-(4-chlorophenyl)-2-(3-methoxy-4-acetylaminophenylthio)-n-butyl]imidazole;

1-[4-(4-chlorophenyl)-2-(3-amino-4-acetylaminophenylthio)-n-butyl]imidazole;

1-[4-(4-chlorophenyl)-2-(4-acetylamino-3-nitrophenylthio)-n-butyl]imidazole;

1-[4-(4-chlorophenyl)-2-(4-amino-3-nitrophenylthio)-n-butyl]imidazole;

1-[4-(4-chlorophenyl)-2-(3,4-di(acetylamino)phenylthio)-n-butyl]imidazole;

1-[4-(4-chlorophenyl)-2-(4-(piperazin-1-yl)phenylthio)-n-butyl]imidazole;

1-[4-(4-chlorophenyl)-2-[4-(4-methylpiperazin-1-yl)phenylthio]-n-butyl]imidazole;

1-[4-(4-chlorophenyl)-2-[4-(4-phenylpiperazin-1-yl)phenylthio]-n-butyl]imidazole;

1-[4-(4-chlorophenyl)-2-[4-(4-(4-aminophenyl)piperazin-1-yl)phenylthio]-n-butyl]imidazole;

1-[4-(4-chlorophenyl)-2-[4-(4-(N-methylaminophenyl)piperazin-1-yl)phenylthio]-n-butyl]imidazole;

1-[4-(4-chlorophenyl)-2-[4-(4-(N,N-dimethylaminophenyl)piperazin-1-yl)phenylthio]-n-butyl]imidazole;

1-[4-(4-chlorophenyl)-2-[4-(4-(acetylamino-phenyl)piperazin-1-yl)phenylthio]-n-butyl]imidazole;

1-[4-(4-chlorophenyl)-2-[4-(4-benzylpiperazin-1-yl)phenylthio]-n-butyl]imidazole;

1-[4-(4-chlorophenyl)-2-[4-(4-(4-fluorobenzyl)piperazin-1-yl)phenylthio]-n-butyl]imidazole;

1-[4-(4-chlorophenyl)-2-[4-(4-formylpiperazin-1-yl)phenylthio]-n-butyl]imidazole;

1-[4-(4-chlorophenyl)-2-[4-(4-acetylpiperazin-1-yl)phenylthio]-n-butyl]imidazole;

1-[4-(4-chlorophenyl)-2-[4-(4-methoxycarbonylpiperazin-1-yl)phenylthio]-n-butyl]imidazole;

1-[4-(4-chlorophenyl)-2-[4-(4-aminocarbonylpiperazin-1-yl)phenylthio]-n-butyl]imidazole;

1-[4-(4-chlorophenyl)-2-[4-(4-aminothiocarbonylpiperazin-1-yl)phenylthio]-n-butyl]imidazole;

1-[4-(4-chlorophenyl)-2-[4-(imidazol-1-yl)phenylthio]-n-butyl]imidazole, m.p. 130°–133° C.;

1-[4-(4-chlorophenyl)-2-[4-(2-methylimidazol-1-yl)phenylthio]-n-butyl]imidazole;

1-[4-(4-chlorophenyl)-2-[4-(2-ethylimidazol-1-yl)phenylthio]-n-butyl]imidazole;

1-[4-(4-chlorophenyl)-2-[4-(1,2,4-triazol-1-yl)phenylthio]-n-butyl]imidazole;

1-[4-(4-chlorophenyl)-2-[4-(1,2,4-traizol-4-yl)phenylthio]-n-butyl]imidazole; 1-[4-(4-chlorophenyl)-2-[4-(pyrazol-1-yl)phenylthio-n-butyl]imidazole, m.p. 120°–121° C.;

1-[4-(4-chlorophenyl)-2-[4-(1,2,3-triazol-1-yl)phenylthio]-n-butyl]imidazole;

1-[4-(4-chlorophenyl)-2-[4-(1,2,3-triazol-2-yl)phenylthio]-n-butyl]imidazole;

1-[4-(4-chlorophenyl)-2-[4-(2-aminoimidazol-1-yl)phenylthio]-n-butyl]imidazole;

1-[4-(4-chlorophenyl)-2-[4-(2-acetylaminoimidazol-1-yl)phenylthio]-n-butyl]imidazole;

1-[4-(4-chlorophenyl)-2-(4-(piperidin-1-yl)phenylthio)-n-butyl]imidazole;

1-[4-(4-chlorophenyl)-2-(4-(pyridin-1-yl)phenylthio)-n-butyl]imidazole;

1-[4-(4-chlorophenyl)-2-(4-(piperazin-1-yl)phenylthio]-n-butyl]imidazole;

C. Similarly, proceeding as above substituting 1-[2-(2,4-dichlorophenyl)-2-methanesulfonyloxyethyl]imidazole for 1-[4-(4-chlorophenyl)-2-methanesulfonyloxy-n-butyl]imidazole and the appropriate thiophenol for 4-acetylaminothiophenol the following compounds are prepared:

1-[2-(2,4-dichlorophenyl)-2-(4-n-propylcarbonylaminophenylthio)ethyl]imidazole;

1-[2-(2,4-dichlorophenyl)-2-(4-n-hexanoylaminophenylthio)ethyl]imidazole;

1-[2-(2,4-dichlorophenyl)-2-(4-(N-methylamino)phenylthio)ethyl]imidazole;

1-[2-(2,4-dichlorophenyl)-2-(4-(N-i-propylamino)phenylthio)ethyl]imidazole;

1-[2-(2,4-dichlorophenyl)-2-(4-(N,N-dimethylamino)phenylthio)ethyl]imidazole;

1-[2-(2,4-dichlorophenyl)-2-(4-(N,N-diethylamino)phenylthio)ethyl]imidazole;

1-[2-(2,4-dichlorophenyl)-2-(4-acetyl-N-butylaminophenylthio)ethyl]imidazole;

1-[2-(2,4-dichlorophenyl)-2-(4-(pyrrolidin-1-yl)phenylthio)ethyl]imidazole;

1-[2-(2,4-dichlorophenyl)-2-(4-(piperidin-1-yl)phenylthio)ethyl]imidazole;

1-[2-(2,4-dichlorophenyl)-2-(4-(morpholin-1-yl)phenylthio)ethyl]imidazole;

1-[2-(2,4-dichlorophenyl)-2-(3-amino-4-acetylaminophenylthio)ethyl]imidazole;

1-[2-(2,4-dichlorophenyl)-2-(3,4-di(acetylamino)phenylthio)ethyl]imidazole;

1-[2-(2,4-dichlorophenyl)-2-[4-(4-methylpiperazin-1-yl)phenylthio]ethyl]imidazole;

1-[2-(2,4-dichlorophenyl)-2-[4-(4-phenylpiperazin-1-yl)phenylthio]ethyl]imidazole;

1-[2-(2,4-dichlorophenyl)-2-[4-(4-aminopiperazin-1-yl)phenylthio]ethyl]imidazole;

1-[2-(2,4-dichlorophenyl)-2-[4-(4-formylpiperazin-1-yl)phenylthio]ethyl]imidazole;

1-[2-(2,4-dichlorophenyl)-2-[4-(4-methoxycarbonylpiperazin-1-yl)phenylthio]ethyl]imidazole;

1-[2-(2,4-dichlorophenyl)-2-[4-(4-aminocarbonylpiperazin-1-yl)phenylthio]ethyl]imidazole;

1-[2-(2,4-dichlorophenyl)-2-[4-(4-aminothiocarbonylpiperazin-1-yl)phenylthio]ethyl]imidazole;

1-[2-(2,4-dichlorophenyl)-2-(4-(imidazol-1-yl)phenylthio)ethyl]imidazole;

1-[2-(2,4-dichlorophenyl)-2-[4-(2-methylimidazol-1-yl)phenylthio]ethyl]imidazole;

1-[2-(2,4-dichlorophenyl)-2-[4-(2-ethylimidazol-1-yl)phenylthio]ethyl]imidazole;

1-[2-(2,4-dichlorophenyl)-2-[4-(1,2,4-triazol-1-yl)phenylthio]ethyl]imidazole;

1-[2-(2,4-dichlorophenyl)-2-[4-(1,2,4-triazol-4-yl)phenylthio]ethyl]imidazole;

1-[2-(2,4-dichlorophenyl)-2-[4-(pyrazol-1-yl)phenylthio]ethyl]imidazole;

1-[2-(2,4-dichlorophenyl)-2-[4-(1,2,3-triazol-1-yl)phenylthio]ethyl]imidazole; and 1-[2-(2,4-dichlorophenyl)-2-[4-(1,2,3-triazol-2-yl)phenylthio]ethyl]imidazole.

D. Similarly, proceeding as above substituting the appropriate methanesulfonyloxy derivatives of compound of formula (II) for 1-[4-(4-chlorophenyl)-2-methane-sulfonyloxy-n-butyl[imidazole and the appropriate thiophenol for 4-acetylaminothiophenol the following compounds are prepared:

1-[4-(4-methoxyphenyl)-2-(4-aminophenylthio)-n-butyl]-imidazole di(hydrochloride)salt, m.p. 148.5°–156° C.;

1-[4-(4-methoxyphenyl)-2-(4-acetylaminophenylthio)-n-butyl]imidazole, m.p. 165°–169° C.;

1-[4-(4-methoxyphenyl)-2-(4-formylaminophenylthio)-n-butyl]imidazole;

1-[4-(4-methoxyphenyl)-2-(4-(imidazol-1-yl)-phenylthio)-n-butyl]imidazole;

1-[4-(4-methoxyphenyl)-2-(4-(4-formylpiperazin-1-yl)phenylthio)-n-butyl]imidazole;

1-[4-(4-methoxyphenyl)-2-(4-(4-acetylpiperazin-1-yl)phenylthio)-n-butyl]imidazole;

1-[4-(4-methoxyphenyl)-2-(4-(pyrrolidin-1-yl)phenylthio)-n-butyl]imidazole;

1-[3-(4-chlorophenyl)-2-(4-aminophenylthio)-n-propyl]imidazole, di(hydrochloride)salt, m.p. 248° C.;

1-[5-(4-chlorophenyl)-2-(4-aminophenylthio)-n-pentyl]imidazole, di(hydrochloride)salt, m.p. 170°–175° C. (foams);

1-[4-(2,4-dichlorophenyl)-2-(4-aminophenylthio)-n-butyl]-imidazole di(hydrochloride)salt m.p. 132°–135° C. (foams);

1-[4-(2,4-dichlorophenyl)-2-(4-acetylaminophenylthio)-n-butyl]imidazole, m.p. 136°–138° C.;

1-[4-(2,4-dichlorophenyl)-2-(4-formylaminophenylthio)-n-butyl]imidazole;

1-[4-(2,4-dichlorophenyl)-2-(4-(imidazol-1-yl)phenylthio)-n-butyl]imidazole;

1-[4-(2,4-dichlorophenyl)-2-(4-(4-formylpiperazin-1-yl)phenylthio)-n-butyl]imidazole;

1-[4-(2,4-dichlorophenyl)-2-(4-(4-acetylpiperazin-1-yl)phenylthio)-n-butyl]imidazole;

1-[4-(2,4-dichlorophenyl)-2-(4-(pyrrolidin-1-yl)phenylthio)-n-butyl]imidazole;

1-[4-(4-methylphenyl)-2-(4-aminophenylthio)-n-butyl]imidazole;

1-[4-(4-methylphenyl)-2-(4-acetylaminophenylthio)-n-butyl]imidazole;

1-[4-(4-methylphenyl)-2-(4-formylaminophenylthio)-n-butyl]imidazole;

1-[4-(4-methylphenyl)-2-(4-(imidazol-1-yl)phenylthio)-n-butyl]imidazole;

1-[4-(4-methylphenyl)-2-(4-(4-formylpiperazin-1-yl)phenylthio)-n-butyl]imidazole;

1-[4-(4-methylphenyl)-2-(4-(4-acetylpiperazin-1-yl)phenylthio)-n-butyl]imidazole;

1-[4-(4-methylphenyl)-2-(4-(pyrrolidin-1-yl)phenylthio)-n-butyl]imidazole;

1-[4-phenyl-2-(4-aminophenylthio)-n-butyl]imidazole;

1-[4-phenyl-2-(4-acetylaminophenylthio)-n-butyl]imidazole;
1-[4-phenyl-2-(4-formylaminophenylthio)-n-butyl]imidazole;
1-[4-phenyl-2-(4-(imidazol-1-yl)phenylthio)-n-butyl]imidazole;
1-[4-phenyl-2-(4-(4-formylpiperazin1-yl)phenylthio)-n-butyl]imidazole;
1-[4-phenyl-2-(4-(4-acetylpiperazin-1-yl)phenylthio)-n-butyl]imidazole;
1-[4-phenyl-2-(4-(pyrrolidin-1-yl)phenylthio)-n-butyl]imidazole;
1-[4-(4-fluorophenyl)-2-(4-aminophenylthio)-n-butyl]imidazole;
1-[4-(4-fluorophenyl)-2-(4-acetylaminophenylthio)-n-butyl]imidazole;
1-[4-(4-fluorophenyl)-2-(4-formylaminophenylthio)-n-butyl]imidazole;
1-[4-(4-fluorophenyl)-2-(4-(imidazol-1-yl)phenylthio)-n-butyl]imidazole;
1-[4-(4-fluorophenyl)-2-(4-(4-formylpiperazin-1-yl)phenylthio)-n-butyl]imidazole;
1-[4-(4-fluorophenyl)-2-(4-(4-acetylpiperazin-1-yl)phenylthio)-n-butyl]imidazole;
1-[4-(4-fluorophenyl)-2-(4-(pyrrolidin-1-yl)phenylthio)-n-butyl]imidazole;
1-[4-(1-naphthyl)-2-(4-aminophenylthio)-n-butyl]imidazole;
1-[4-(1-naphthyl)-2-(4-acetylaminophenylthio)-n-butyl]imidazole;
1-[4-(1-naphthyl)-2-(4-formylaminophenylthio)-n-butyl]imidazole;
1-[4-(1-naphthyl)-2-(4-(imidazol-1-yl)phenylthio)-n-butyl]imidazole;
1-[4-(1-naphthyl)-2-(4-(4-formylpiperazin-1-yl)phenylthio)-n-butyl]imidazole;
1-[4-(1-naphthyl)-2-(4-(4-acetylpiperazin-1-yl)phenylthio)-n-butyl]imidazole;
1-[4-(1-naphthyl)-2-(4-(pyrrolidin-1-yl)phenylthio)-n-butyl]imidazole;
1-[4-(2-naphthyl)-2-(4-aminophenylthio)-n-butyl]imidazole;
1-[4-(2-naphthyl)-2-(4-acetylaminophenylthio)-n-butyl]imidazole;
1-[4-(2-naphthyl)-2-(4-formylaminophenylthio)-n-butyl]imidazole;
1-[4-(2-naphthyl)-2-(4-(imidazol-1-yl)phenylthio)-n-butyl]imidazole;
1-[4-(2-naphthyl)-2-(4-(4-formylpiperazin-1-yl)phenylthio)-n-butyl]imidazole;
1-[4-(2-naphthyl)-2-(4-(4-acetylpiperazin-1-yl)phenylthio)-n-butyl]imidazole;
1-[4-(2-naphthyl)-2-(4-(pyrrolidin-1-yl)phenylthio)-n-butyl]imidazole;
1-[4-(thien-2-yl)-2-(4-aminophenylthio)-n-butyl]imidazole;
1-[4-(thien-2-yl)-2-(4-acetylaminophenylthio)-n-butyl]imidazole;
1-[4-(thien-2-yl)-2-(4-formylaminophenylthio)-n-butyl]imidazole;
1-[4-(thien-2-yl)-2-(4-(imidazol-1-yl)phenylthio)-n-butyl]imidazole;
1-[4-(thien-2-yl)-2-(4-(4-formylpiperazin-1-yl)phenylthio)-n-butyl]imidazole;
1-[4-(thien-2-yl)-2-(4-(4-acetylpiperazin-1-yl)phenylthio)-n-butyl]imidazole;
1-[4-(thien-2-yl)-2-(4-(pyrrolidin-1-yl)phenylthio)-n-butyl]imidazole;
1-[4-(5-chlorothien-2-yl)-2-(4-aminophenylthio)-n-butyl]-imidazole;
1-[4-(5-chlorothien-2-yl)-2-(4-acetylaminophenylthio)-n-butyl]imidazole;
1-[4-(5-chlorothien-2-yl)-2-(4-formylaminophenylthio)-n-butyl]imidazole;
1-[4-(5-chlorothien-2-yl)-2-(4-(imidazol-1-yl)phenylthio)-n-butyl]imidazole;
1-[4-(5-chlorothien-2-yl)-2-(4-(4-formylpiperazin-1-yl)phenylthio)-n-butyl]imidazole;
1-[4-(5-chlorothien-2-yl)-2-(4-(4-acetylpiperazin-1-yl)phenylthio)-n-butyl]imidazole;
1-[4-(5-methylthien-2-yl)-2-(4-aminophenylthio)-n-butyl]-imidazole;
1-[4-(5-chlorothien-2-yl)-2-(4-(pyrrolidin-1-yl)phenylthio)-n-butyl]imidazole;
1-[4-(5-methylthien-2-yl)-2-(4-acetylaminophenylthio)-n-butyl]imidazole;
1-[4-(5-methylthien-2-yl)-2-(4-formylaminophenylthio)-n-butyl]imidazole;
1-[4-(5-methylthien-2-yl)-2-(4-(imidazol-1-yl)phenylthio)-n-butyl]imidazole;
1-[4-(5-methylthien-2-yl)-2-(4-(4-formylpiperazin-1-yl)phenylthio)-n-butyl]imidazole;
1-[4-(5-methylthien-2-yl)-2-(4-(4-acetylpiperazin-1-yl)phenylthio)-n-butyl]imidazole;
1-[4-(5-methylthien-2-yl)-2-(4-(pyrrolidin-1-yl)phenylthio)-n-butyl]imidazole;
1-[4-(5-methylfuran-2-yl)-2-(4-aminophenylthio)-n-butyl]imidazole;
1-[4-(5-methylfuran-2-yl)-2-(4-acetylaminophenylthio)-n-butyl]imidazole;
1-[4-(5-methylfuran-2-yl)-2-(4-formylaminophenylthio)-n-butyl]imidazole;
1-[4-(5-methylfuran-2-yl)-2-(4-(imidazol-1-yl)phenylthio)-n-butyl]imidazole;
1-[4-(5-methylfuran-2-yl)-2-(4-(4-formylpiperazin-1-yl)phenylthio)-n-butyl]imidazole;
1-[4-(5-methylfuran-2-yl)-2-(4-(4-acetylpiperazin-1-yl)phenylthio)-n-butyl]imidazole;
1-[4-(5-methylfuran-2-yl)-2-(4-(pyrrolidin-1-yl)phenylthio)-n-butyl]imidazole;
1-[4-(pyridin-4-yl)-2-(4-aminophenylthio)-n-butyl]imidazole;
1-[4-(pyridin-4-yl)-2-(4-acetylaminophenylthio)-n-butyl]imidazole;
1-[4-(pyridin-4-yl)-2-(4-formylaminophenylthio)-n-butyl]imidazole;
1-[4-(pyridin-4-yl)-2-(4-(imidazol-1-yl)phenylthio)-n-butyl]imidazole;
1-[4-(pyridin-4-yl)-2-(4-(4-formylpiperazin-1-yl)phenylthio)-n-butyl]imidazole;
1-[4-(pyridin-4-yl)-2-(4-(4-acetylpiperazin-1-yl)phenylthio)-n-butyl]imidazole;
1-[4-(pyridin-4-yl)-2-(4-(pyrrolidin-1-yl)phenylthio)-n-butyl]imidazole;
1-[2-(4-aminophenylthio)-3,3-dimethylbutyl]imidazole, m.p. 148°–149° C.; and
1-[2-(4-acetylaminophenylthio)-3,3-dimethylbutyl]imidazole, hydrochloride salt m.p. 125°–145° C.

EXAMPLE 3

1-[4-(4-Chlorophenyl)-2-methanesulfonyloxy-n-butyl]imidazole hydrochloride (3.65 g) (prepared in Preparation 10) in methylene chloride (50 ml) was shaken with excess 10% aqueous potassium carbonate solution until no solid remained. The organic layer was separated, dried (MgSO₄) and evaporated to give 1-[4-

(4-chlorophenyl)-2-methanesulfonyloxy-n-butyl-]imidazole as a solid.

The above solid was mixed with 3-aminothiophenol (1.6 g) and anhydrous potassium carbonate (1.55 g) in acetone (60 ml) and heated under reflux with stirring overnight. The solvent was then evaporated, water (50 ml) added, and the residue extracted with ether (2×50 ml). The extracts were washed, dried (MgSO$_4$) and divided into two equal parts (see also Example 4). One of these was evaporated, and the residue chromatographed on silica gel eluting with 2.2% water in ethyl acetate. The pure product crystallized spontaneously and was recrystallized from ethyl acetate/ether to give 1-[4-(4-chlorophenyl)-2-(3-aminophenylthio)-n-butyl-]imidazole as a pale straw colored solid (1.17 g), m.p. 89°–91° C.

EXAMPLE 4

The resulting ethereal solution from Example 4 containing 1-[4-(4-chlorophenyl)-2-(3-aminophenylthio)-n-butyl]imidazole was treated at room temperature with stirring with acetic anhydride (1.5 m.). After stirring overnight, the mixture was evaporated to dryness in vacuo and the residue chromatographed on silica gel eluting with methylene chloride followed by 2.2% water in ethyl acetate. The resulting pure product, 1-[4-(4-chlorophenyl)-2-(3-acetylaminophenylthio)-n-butyl-]imidazole, obtained as a gum, was dissolved in a small volume of methanol and treated with excess ethereal hydrogen chloride. The solution was filtered, evaporated almost to dryness and evacuated in a warm water bath to give 1-[4-(4-chlorophenyl)-2-(3-acetylaminophenylthio)-n-butyl]imidazole hydrochloride 1.79 g as a brittle foam, dec 87°–92° C.

EXAMPLE 5

A mixture of 1-[4-(4-chlorophenyl)-2-methanesulfonyloxy-n-butyl]imidazole hydrochloride (3.65 g) and 2-acetamidophenyl (1.51 g) in 40 ml of dry dimethylsulfoxide under nitrogen was treated with stirring with sodium hydride (960 mg of 50% dispersion). The resulting mixture was stirred at ambient temperature until all the sodium hydride was dissolved, and then warmed overnight at 80° C. The solution was then poured into water and extracted with ethyl acetate (3×50 ml) and the combined extracts dried over magnesium sulfate and chromatographed on silica gel, eluting with wet ethyl acetate (2.2% water) to give pure 1-[4-(4-chlorophenyl)-2-(2-acetylaminophenoxy)-n-butyl]imidazole. This product was converted to the hydrochloride salt by dissolving in ethyl acetate, diluting with ether until the solution was slightly turbid, and treating with ethereal hydrogen chloride until precipitation was complete. The precipitate was collected and recrystallized from methanol/acetone to give the hydrochloride, m.p. 151°–152°.

EXAMPLE 6

A. A solution of 1-[4-(4-chlorophenyl)-2-(4-acetylamino-2,6-dichlorophenoxy)-n-butyl]imidazole (1.58 g) (prepared as in Example 1) in 15 ml of concentrated hydrochloric acid was heated at 90° C. for 1 day. The resulting solution was poured into 200 ml of aqueous potassium carbonate solution, extracted with ethyl acetate (3×75 ml) and the combined extracts dried (MgSO$_4$) and evaporated. The resulting oil (1.3 g) was dissolved in ether and treated with ethereal hydrogen chloride until precipitation was complete. The product was filtered off and dried immediately in vacuo to give 1.4 g of 1-[4-(4-chlorophenyl)-2-(4-amino-2,6-dichlorophenoxy)-n-butyl]imidazole bis(hydrochloride), m.p. 119°–123° C.

B. Similarly, proceeding as in Part A substituting the apropriate compound for 1-[4-(4-chlorophenyl)-2-(4-acetylamino-2,6-dichlorophenoxy)-n-butyl]imidazole the following compounds are prepared.

1-[4-(4-chlorophenyl)-2-(2-aminophenoxy)-n-butyl-]imidazole;

1-[4-(4-chlorophenyl)-2-(3-aminophenoxy)-n-butyl-]imidazole;

1-[4-(4-chlorophenyl)-2-(4-aminophenoxy)-n-butyl-]imidazole di(hydrochloride)salt;
UV(MeOH) 220, 268, 276, 299 nm (ε18800, 1190, 1200, 1120).
ir(KBr) 1620, 1610, 1505, 1245, 830 cm$^{-1}$.
nmr(d$_6$DMSO)4.62 m(CH$_2$N), 4.84(CHO), 7.02 and 7.36(N-phenoxy), 7.67, 7.83, 9.32 (imidazole ring).

1-[4-(4-chlorophenyl)-2-(2-(N-methylamino)phenoxy)-n-butyl]imidazole;

1-[4-(4-chlorophenyl)-2-(3-(N-methylamino)phenoxy)-n-butyl]imidazole;

1-[4-(4-chlorophenyl)-2-(4-(N-methylamino)phenoxy)-n-butyl]imidazole di(hydrochloride)salt;
UV(MeOH) 220, 246, 310 nm (ε18500, 7580, 1140)
ir(KBr) 1500, 1245 cm$^{-1}$.
nmr (d$_6$DMSO)2.86m(NMe), 4.61(CH$_2$N), 4.87 (CHO), 7.07d and 7.52d(N-phenoxy), 7.67, 7.82, 9.28 (imidazole).

1-[4-(4-chlorophenyl)-2-(4-(N-ethylamino)phenoxy)-n-butyl]imidazole;

1-[4-(4-chlorophenyl)-2-(4-(N-butylamino)phenoxy)-n-butyl]imidazole;

1-[4-(4-chlorophenyl)-2-(4-(N-hexylamino)phenoxy)-n-butyl]imidazole;

1-[4-(4-chlorophenyl)-2-(4-(N-cyclohexylamino)phenoxy)-n-butyl]imidazole;

1-[4-(4-chlorophenyl)-2-(4-(N-(4-methoxyphenyl)amino)phenoxy)-n-butyl]imidazole;

1-[4-(4-chlorophenyl)-2-(4-(N-benzylaminophenoxy)-n-butyl]imidazole;

1-[4-(4-chlorophenyl)-2-(4-(N-methylamino)phenoxy)-n-butyl]imidazole;

1-[4-(4-chlorophenyl)-2-(4-amino-2,5-dimethylphenoxy)-n-butyl]imidazole;

1-[4-(4-chlorophenyl)-2-(4-amino-2-methylphenoxy)-n-butyl]imidazole;

1-[4-(4-chlorophenyl)-2-(4-amino-3-methylphenoxy)-n-butyl]imidazole di(hydrochloride)salt, m.p. 135°–142° C. (dec.);

1-[4-(4-chlorophenyl)-2-(4-amino-3-methoxyphenoxy)-n-butyl]imidazole;

1-[4-(4-chlorophenyl)-2-(4-amino-2,6-dichlorophenoxy)-n-butyl]imidazole di(hydrochloride)salt, m.p. 119°–123° C.;

1-[4-(4-chlorophenyl)-2-(4-amino-2,5-dichlorophenoxy)-n-butyl]imidazole di(hydrochloride)salt, m.p. 115°–124° C. (dec.);

1-[4-(4-chlorophenyl)-2-(4-amino-3-chlorophenoxy)-n-butyl]imidazole;

1-[4-(4-chlorophenyl)-2-(4-amino-3-nitrophenoxy)-n-butyl]imidazole di(hydrochloride)salt;
UV(MeOH) 225nm(ε26200).
ir(KBr) 1510, 1260, 1210, 1090, 1020, 820 cm$^{-1}$.
nmr (d$_6$DMSO) 4.58m(CH$_2$N), 4.68(OCH), 7.67, 7.82, 9.27 (imidazole).

1-[2-(2,4-dichlorophenyl)-2-(4-(N-methylamino)phenoxy)ethyl]imidazole;
1-[2-(2,4-dichlorophenyl)-2-(4-(N-ethylamino)phenoxy)ethyl]imidazole;
1-[2-(2,4-dichlorophenyl)-2-(4-(N-butylamino)phenoxy)ethyl]imidazole;
1-[4-(4-methoxyphenyl)-2-(4-aminophenoxy)-n-butyl]imidazole;
1-[4-(2,4-dichlorophenyl)-2-(4-aminophenoxy)-n-butyl]imidazole;
1-[4-(4-methylphenyl)-2-(4-aminophenoxy)-n-butyl]imidazole;
1-[4-phenyl-2-(4-aminophenoxy)-n-butyl]imidazole;
1-[4-(4-fluorophenyl)-2-(4-aminophenoxy)-n-butyl]imidazole;
1-[4-(1-naphthyl)-2-(4-aminophenoxy)-n-butyl]imidazole;
1-[4-(thien-2-yl)-2-(4-aminophenoxy)-n-butyl]imidazole;
1-[4-(5-chlorothien-2-yl)-2-(4-aminophenoxy)-n-butyl]imidazole;
1-[4-(5-methylthien-2-yl)-2-(4-aminophenoxy)-n-butyl]imidazole;
1-[4-(furan-2-yl)-2-(4-aminophenoxy)-n-butyl]imidazole;
1-[4-(5-methylfuran-2-yl)-2-(4-aminophenoxy)-n-butyl]imidazole;
1-[4-(pyridin-4-yl)-2-(4-aminophenoxy)-n-butyl]imidazole;
1-[2-(4-aminophenoxy)-n-butyl]imidazole;
1-[2-(4-aminophenoxy)-n-hexyl]imidazole;
1-[2-(4-aminophenoxy)-3,3-dimethylbutyl]imidazole, di(hydrochloride)salt, m.p. 265°–270° C. (dec);
1-[2-(4-aminophenoxy)-n-octyl]imidazole;
1-[2-(4-aminophenoxy)-n-decyl]imidazole;
1-[2-(4-aminophenoxy)-n-tetradecyl]imidazole;
1-[2-cyclohexyl-2-(4-aminophenoxy)ethyl]imidazole;
1-[4-cyclohexyl-2-(4-aminophenoxy)-n-butyl]imidazole;
1-[2-(4-methylcyclohexyl)-2-(4-aminophenoxy)ethyl]imidazole;
1-[2-(2-methylcyclohexyl)-2-(4-aminophenoxy)ethyl]imidazole;
1-[2-(4-t-butylcyclohexyl)-2-(4-aminophenoxy)ethyl]imidazole;
1-[3-(4-chlorophenyl)-2-(4-aminophenoxy)-n-propyl]imidazole;
1-[5-(4-chlorophenyl)-2-(4-aminophenoxy)-n-pentyl]imidazole;
1-[2-(pyridin-4-yl)-2-(4-aminophenoxy)ethyl]imidazole;
1-[2-(pyridin-2-yl)-2-(4-aminophenoxy)ethyl]imidazole;
1-[3-(2,4-dichlorophenyl)-3-(4-aminophenoxy)-n-propyl]imidazole;
1-[4-(4-chlorophenyl)-3-(4-aminophenoxy)-n-butyl]imidazole;
1-[4-(4-methoxyphenyl)-3-(4-aminophenoxy)-n-butyl]imidazole;
1-[3-(4-aminophenoxy)-n-butyl]imidazole;
1-[3-(4-aminophenoxy)-n-heptyl]imidazole;
1-[3-(4-aminophenoxy)-n-octyl]imidazole;
1-[4-(2,4-dichlorophenyl)-4-(4-aminophenoxy)-n-butyl]imidazole;
1-[5-(4-chlorophenyl)-4-(4-aminophenoxy)-n-pentyl]imidazole;
1-[4-(4-aminophenoxy)-n-pentyl]imidazole;
1-[4-(4-aminophenoxy)-n-octyl]imidazole;
1-[4-(4-aminophenoxy)-n-nonyl]imidazole;
1-[2-(4-aminophenoxy)ethyl]imidazole;
1-[2-(4-aminophenoxy)-3-methyl-n-butyl]imidazole;
1-[4-cyclopentyl-2-(4-aminophenoxy)-n-butyl]imidazole;
1-[4-(4-methylthiophenyl)-2-(4-aminophenoxy)-n-butyl]imidazole;
1-[4-(4-cyanophenyl)-2-(4-aminophenoxy)-n-butyl]imidazole;
1-[4-(4-trifluoromethylphenyl)-2-(4-aminophenoxy)-n-butyl]imidazole;
1-[4-(4-t-butylphenyl)-2-(4-aminophenoxy)-n-butyl]imidazole;
1-[4-(4-bromophenyl)-2-(4-aminophenoxy)-n-butyl]imidazole;
1-[4-(2,4-dimethylphenyl)-2-(4-aminophenoxy)-n-butyl]imidazole;
1-[5-(4-chlorophenyl)-3-(4-aminophenoxy)-n-pentyl]imidazole;
1-[6-(4-chlorophenyl)-4-(4-aminophenoxy)-n-hexyl]imidazole;
1-[4-(thien-3-yl)-2-(4-aminophenoxy)-n-butyl]imidazole;
1-[2-(1-naphthyl)-2-(4-aminophenoxy)ethyl]imidazole;
1-[3-(1-naphthyl)-3-(4-aminophenoxy)-n-propyl]imidazole;
1-[3-(2-naphthyl)-3-(4-aminophenoxy)-n-propyl]imidazole; and
1-[4-(2-naphthyl)-2-(4-aminophenoxy)-n-butyl]imidazole.

EXAMPLE 7

A. A solution of 1.35 g of 1-[2-chloro-4-(4-chlorophenyl)butyl]imidazole and 1.60 g of 4-nitrobenzyl mercaptan in 40 ml tetrahydrofuran was treated with 380 mg of 50% sodium hydride dispersion in mineral oil. After stirring at room temperature for 1 hour and under reflux for 12 hours the solvent was evaporated under vacuum and 50 ml of ether added. The resulting mixture was washed twice with water and the ethereal solution dried (MgSO$_4$) and evaporated. The residue was chromatographed on silica gel eluting with 5% methanol in methylene chloride to give 1-[4-(4-chlorophenyl)-2-(4-nitrobenzylthio)-n-butyl]imidazole.

This is reduced by the precedure described below in Example 15 to provide 1-[4-(4-chlorophenyl)-2-(4-aminobenzylthio)-n-butyl]imidazole.

B. Similarly, proceeding as above substituting the appropriate intermediate for 4-nitrobenzyl mercaptan the following compounds are prepared:
1-[4-(4-chlorophenyl)-2-(3-aminobenzylthio)-n-butyl]imidazole;
1-[4-(4-chlorophenyl)-2-[2-(4-aminophenyl)ethylthio]-n-butyl]imidazole;
1-[4-(4-chlorophenyl)-2-(3-(4-aminophenyl)propylthio)-n-butyl]imidazole;
1-[4-(4-methoxyphenyl)-2-(4-aminobenzylthio)-n-butyl]imidazole;
1-(4-methoxyphenyl)-2-[2-(4-aminophenyl)ethylthio]-n-butyl]imidazole;
1-[4-(4-methoxyphenyl)-2-(3-(4-aminophenyl)propylthio)-n-butyl]imidazole;
1-[4-(2,4-dichlorophenyl)-2-(4-aminobenzylthio)-n-butyl]imidazole;
1-[4-(2,4-dichlorophenyl)-2-[2-(4-aminophenyl)ethylthio]-n-butyl]imidazole;
1-[4-(2,4-dichlorophenyl)-2-(3-(4-aminophenyl)propylthio)-n-butyl]imidazole;
1-[4-(4-methylphenyl)-2-(4-aminobenzylthio)-n-butyl]imidazole;
1-[4-(4-methylphenyl)-2-[2-(4-aminophenyl)ethylthio]-n-butyl]imidazole;

1-[4-(4-methylphenyl)-2-(3-(4-aminophenyl)propylthio)-n-butyl]imidazole;
1-[4-phenyl-2-(4-aminobenzylthio)-n-butyl]imidazole;
1-[4-phenyl-2-[2-(4-aminophenyl)ethylthio-n-butyl]imidazole;
1-[4-phenyl-2-(3-(4-aminophenyl)propylthio)-n-butyl]imidazole;
1-[4-(4-fluorophenyl)-2-(4-aminobenzylthio)-n-butyl]imidazole;
1-[4-(4-fluorophenyl)-2-[2-(4-aminophenyl)ethylthio]-n-butyl]imadazole;
1-[4-(4-fluorophenyl)-2-(3-(4-aminophenyl)propylthio)-n-butyl]imidazole;
1-[4-(1-naphthyl)-2-(4-aminobenzylthio)-n-butyl]imidazole;
1-[4-(1-naphthyl)-2-[2-(4-aminophenyl)ethylthio]-n-butyl]imidazole;
1-[4-(1-naphthyl)-2-(3-(4-aminophenyl)propylthio)-n-butyl]imidazole;
1-[4-(2-naphthyl)-2-(4-aminobenzylthio)-n-butyl]imidazole;
1-[4-(2-naphthyl)-2-[2-(4-aminophenyl)ethylthio]-n-butyl]imidazole;
1-[4-(2-naphthyl)-2-(3-(4-aminophenyl)propylthio)-n-butyl]imidazole;
1-[4-(thien-2-yl)-2-(4-aminobenzylthio)-n-butyl]imidazole;
1-[4-(thien-2-yl)-2-[2-(4-aminophenyl)ethylthio]-n-butyl]imidazole;
1-[4-(thien-2-yl)-2-(3-(4-aminophenyl)propylthio)-n-butyl]imidazole;
1-[4-(5-chlorothien-2-yl)-2-(4-aminobenzylthio)-n-butyl]imidazole;
1-[4-(5-chlorothien-2-yl)-2-[2-(4-aminophenyl)ethylthio]-n-butyl]imidazole;
1-[4-(5-chlorothien-2-yl)-2-(3-(4-aminophenyl)propylthio)-n-butyl]imidazole;
1-[4-(5-methylthien-2-yl)-2-(4-aminobenzylthio)-n-butyl]imidazole;
1-[4-(5-methylthien-2-yl)-2-[2-(4-aminophenyl)-ethylthio]-n-butyl]imidazole;
1-[4-(5-methylthien-2-yl)-2-(3-(4-aminophenyl)propylthio)-n-butyl]imidazole;
1-[4-(pyridin-4-yl)-2-(4-aminobenzylthio)-n-butyl]imidazole;
1-[4-(pyridin-4-yl)-2-[2-(4-aminophenyl)ethylthio)-n-butyl]imidazole; and
1-[4-(pyridin-4-yl)-2-(3-(4-aminophenyl)propylthio)-n-butyl]imidazole.

C. Proceeding as in Example 4, using the appropriate acylating agent and the compounds in Part B above the following compounds are prepared:

1-[4-(4-chlorophenyl)-2-(4-formylaminobenzyl)-n-butyl]imidazole;
1-[4-(4-chlorophenyl)-2-(4-formylaminophenylethylthio)-n-butyl]imidazole;
1-[4-(4-chlorophenyl)-2-[2-(4-acetylaminophenyl)ethylthio]-n-butyl]imidazole;
1-[4-(4-chlorophenyl)-2-(3-(4-formylaminophenyl)propylthio)-n-butyl]imidazole; and
1-[4-(4-chlorophenyl)-2-(3-(4-acetylaminophenyl)propylthio)-n-butyl]imidazole.
1-[4-(4-methoxyphenyl)-2-(4-acetylaminobenzylthio)-n-butyl]imidazole;
1-[4-(4-methoxyphenyl)-2-[2-(4-acetylaminophenyl)ethylthio]-n-butyl]imidazole;
1-[4-(4-methoxyphenyl)-2-(3-(4-acetylaminophenyl)propylthio)-n-butyl]imidazole;
1-[4-(2,4-dichlorophenyl)-2-(4-acetylaminobenzylthio)-n-butyl]imidazole;
1-[4-(2,4-dichlorophenyl)-2-[2-(4-acetylaminophenyl)ethylthio]-n-butyl]imidazole;
1-[4-(2,4-dichlorophenyl)-2-(3-(4-acetylaminophenyl)propylthio)-n-butyl]imidazole;
1-[4-(4-methylphenyl)-2-(4-acetylaminobenzylthio)-n-butyl]imidazole;
1-[4-(4-methylphenyl)-2-[2-(4-acetylaminophenyl)ethylthio]-n-butyl]imidazole;
1-[4-(4-methylphenyl)-2-(3-(4-acetylaminophenyl)propylthio)-n-butyl]imidazole;
1-[4-phenyl-2-(4-acetylaminobenzylthio)-n-butyl]imidazole;
1-[4-phenyl-2-[2-(4-acetylaminophenyl)ethylthio]-n-butyl]imidazole;
1-[4-phenyl-2-(3-(4-acetylaminophenyl)propylthio) -n-butyl]imidazole;
1-[4-(4-fluorophenyl)-2-(4-acetylaminobenzylthio)-n-butyl]imidazole;
1-[4-(4-fluorophenyl)-2-[2-(4-acetylaminophenyl)ethylthio]-n-butyl]imidazole;
1-[4-(4-fluorophenyl)-2-(3-(4-acetylaminophenyl)propylthio)-n-butyl]imidazole;
1-[4-(1-naphthyl)-2-(4-acetylaminobenzylthio)-n-butyl]imidazole;
1-[4-(1-naphthyl)-2-[2-(4-acetylaminophenyl)ethylthio]-n-butyl]imidazole;
1-[4-(1-naphthyl)-2-(3-(4-acetylaminophenyl)propylthio)-n-butyl]imidazole;
1-[4-(2-naphthyl)-2-(4-acetylaminobenzylthio)-n-butyl]imidazole;
1-[4-(2-naphthyl)-2-[2-(4-acetylaminophenyl)ethylthio]-n-butyl]imidazole;
1-[4-(2-naphthyl)-2-(3-(4-acetylaminophenyl)propylthio)-n-butyl]imidazole;
1-[4-thien-2-yl-2-(4-acetylaminobenzylthio)-n-butyl]imidazole;
1-[4-thien-2-yl-2-[2-(4-acetylaminophenylethylthio]-n-butyl]imidazole;
1-[4-thien-2-yl-2-(3-(4-acetylaminophenyl)propylthio)-n-butyl]imidazole;
1-[4-(5-chlorothien-2-yl)-2-(4-acetylaminobenzylthio)-n-butyl]imidazole;
1-[4-(5-chlorothien-2-yl)-2-[2-(4-acetylaminophenyl)ethylthio]-n-butyl]imidazole;
1-[4-(5-chlorothien-2-yl)-2-(3-(4-acetylaminophenyl)propylthio)-n-butyl]imidazole;
1-[4-(5-methylthien-2-yl)-2-(4-acetylaminobenzylthio)-n-butyl]imidazole;
1-[4-(5-methylthien-2-yl)-2-[2-(4-acetylaminophenyl)ethylthio]-n-butyl]imidazole;
1-[4-(5-methylthien-2-yl)-2-(3-(4-acetylaminophenyl)propylthio)-n-butyl]imidazole;
1-[4-(pyridin-4-yl)-2-(4-acetylaminobenzylthio)-n-butyl]imidazole;
1-[4-(pyridin-4-yl)-2-[2-(4-acetylaminophenylethyl)thio]-n-butyl]imidazole; and
1-[4-(pyridin-4-yl)-2-(3-(4-acetylaminophenyl)propylthio)-n-butyl]imidazole.

EXAMPLE 8

A mixture of 1-[4-(4-chlorophenyl)-2-hydroxy-n-butyl]imidazole (500 mg) and 4-acetylaminobenzyl trichloroimidate (1.24 g) (prepared by the general method in Chem. Ber. 91, 1049 (1958)) in 10 ml of methylene chloride was treated with 0.3 ml of trifluoromethanesulfonic acid and stirred overnight under reflux under nitrogen. A further 650 mg of imidate was then added and heating continued for a further day. The cooled reaction mixture was then basified with aqueous potassium carbonate solution and extracted with methylene chloride. The extracts were dried (MgSO₄) and evaporated and the residue chromatographed on silica gel eluting with methylene chloride followed by 2.2% water in ethyl acetate to give 1-[4-(4-chlorophenyl)-2-(4-acetylaminobenzyloxy)-n-butyl]imidazole.

EXAMPLE 9

A. A mixture of 1.25 g of 1-[2-hydroxy-4-(4-chlorophenyl)-n-butyl]imidazole and 0.26 g of sodium hydride (50% dispersion in mineral oil) in 20 ml of tetrahydrofuran was stirred under nitrogen at room temperature for one hour, and at 60° C. for one hour. The mixture was then cooled to 0° C. and treated dropwise with stirring with 4-acetylaminobenzyl chloride in 10 ml tetrahydrofuran, keeping the temperature below 10° C. After stirring for one hour, the mixture was heated to 60° C. for 2 hours and poured into water. The product was extracted with ethyl acetate and the extracts dried (MgSO₄) and evaporated. The residue was chromatographed on silica gel eluting with 2% water in ethyl acetate to give 1-[4-(4-chlorophenyl)-2-(4-acetylaminobenzyloxy)-n-butyl]imidazole.

B. Similarly, proceeding as above substituting the appropriate intermediate for 4-acetylaminobenzyl chloride and the appropriate compound, if necessary, for 1-[2-hydroxy-4-(4-chlorophenyl)-n-butyl]imidazole the following compounds are prepared:

1-[4-(4-chlorophenyl)-2-(4-formylaminobenzyloxy)-n-butyl]imidazole;
1-[4-(4-chlorophenyl)-2-(4-acetylaminobenzyloxy)-n-butyl]imidazole;
1-[4-(4-chlorophenyl)-2-(2-(4-formylaminophenyl)ethoxy)-n-butyl]imidazole;
1-[4-(4-chlorophenyl)-2-(2-(4-acetylaminophenyl)ethoxy)-n-butyl]imidazole;
1-[4-(4-chlorophenyl)-2-(3-(4-formylaminophenyl)propoxy)-n-butyl]imidazole;
1-[4-(4-chlorophenyl)-2-(3-(4-acetylaminophenyl)propoxy)-n-butyl]imidazole.
1-[4-(4-methoxyphenyl)-2-(4-acetylaminobenzyloxy)-n-butyl]imidazole;
1-[4-(4-methoxyphenyl)-2-(2-(4-acetylaminophenyl)ethoxy)-n-butyl]imidazole;
1-[4-(4-methoxyphenyl)-2-(3-(4-acetylaminophenyl)propoxy)-n-butyl]imidazole;
1-[4-(2,4-dichlorophenyl)-2-(4-acetylaminobenzyloxy)-n-butyl]imidazole;
1-[4-(2,4-dichlorophenyl)-2-(2-(4-acetylaminophenyl)ethoxy)-n-butyl]imidazole;
1-[4-(2,4-dichlorophenyl)-2-(3-(4-acetylaminophenyl)propoxy)-n-butyl]imidazole;
1-[4-(4-methylphenyl)-2-(4-acetylaminobenzyloxy)-n-butyl]imidazole;
1-[4-(4-methylphenyl)-2-(2-(4-acetylaminophenyl)ethoxy)-n-butyl]imidazole;
1-[4-(4-methylphenyl)-2-(3-(4-acetylaminophenyl)propoxy)-n-butyl]imidazole;
1-[4-phenyl-2-(4-acetylaminobenzyloxy)-n-butyl]imidazole;
1-[4-phenyl-2-(2-(4-acetylaminophenyl)ethoxy)-n-butyl]imidazole;
1-[4-phenyl-2-(3-(4-acetylaminophenyl)propoxy)-n-butyl]imidazole;
1-[4-(4-fluorophenyl)-2-(4-acetylaminobenzyloxy)-n-butyl]imidazole;
1-[4-(4-fluorophenyl)-2-(2-(4-acetylaminophenyl)ethoxy)-n-butyl]imidazole;
1-[-4-(4-fluorophenyl)-2-(3-(4-acetylamino-3-fluorophenyl)propoxy)-n-butyl]imidazole;
1-[4-(1-naphthyl)-2-(4-acetylaminobenzyloxy)-n-butyl]imidazole;
1-[4-(1-naphthyl)-2-(2-(4-acetylaminophenyl)ethoxy)-n-butyl]imidazole;
1-[4-(1-naphthyl)-2-(3-(4-acetylaminophenyl)propoxy)-n-butyl]imidazole;
1-[4-(2-naphthyl)-2-(4-acetylaminobenzyloxy)-n-butyl]imidazole;
1-[4-(2-naphthyl)-2-(2-(4-acetylaminophenylethoxy)-n-butyl]imidazole;
1-[4-(2-naphthyl)-2-(3-(4-acetylaminophenyl)propoxy)-n-butyl]imidazole;
1-[4-(thien-2-yl)-2-(4-acetylaminobenzyloxy)-n-butyl]imidazole;
1-[4-(thien-2-yl)-2-(2-(4-acetylaminophenyl)ethoxy)-n-butyl]imidazole;
1-[4-(thien-2-yl)-2-(3-(4-acetylaminophenyl)propyloxy)-n-butyl]imidazole;
1-[4-(5-chlorothien-2-yl)-2-(4-acetylaminobenzyloxy)-n-butyl]imidazole;
1-[4-(5-chlorothien-2-yl)-2-(2-(4-acetylaminophenyl)ethoxy)-n-butyl]imidazole;
1-[4-(5-chlorothien-2-yl)-2-(3-(4-acetylaminophenyl)propyloxy)-n-butyl]imidazole;
1-[4-(5-methylthien-2-yl)-2-(4-acetylaminobenzyloxy)-n-butyl]imidazole;
1-[4-(5-methylthien-2-yl)-2-(2-(4-acetylaminophenyl)ethoxy)-n-butyl]imidazole;
1-[4-(5-methylthien-2-yl)-2-(3-(4-acetylaminophenyl)propoxy)-n-butyl]imidazole;
1-[4-(furan-2-yl)-2-(4-acetylaminobenzyloxy)-n-butyl]imidazole;
1-[4-(furan-2-yl)-2-(2-(4-acetylaminophenyl)ethoxy)-n-butyl]imidazole;
1-[4-(furan-2-yl)-2-(3-(4-acetylaminophenyl)propyloxy)-n-butyl]imidazole;
1-[4-(5-methylfuran-2-yl)-2-(4-acetylaminobenzyloxy)-n-butyl]imidazole;
1-[4-(5-methylfuran-2-yl)-2-(2-(4-acetylaminophenyl)ethoxy)-n-butyl]imidazole;
1-[4-(5-methylfuran-2-yl)-2-(3-(4-acetylaminophenyl)propyloxy)-n-butyl]imidazole;
1-[4-(pyridin-4-yl)-2-(4-acetylaminobenzyloxy)-n-butyl]imidazole;
1-[4-(pyridin-4-yl)-2-(2-(4-acetylaminophenyl)ethoxy)-n-butyl]imidazole; and
1-[4-(pyridin-4-yl)-2-(3-(4-acetylaminophenyl)propyloxy)-n-butyl]imidazole.

C. Similarly, proceeding as in Example 6 using the compounds in Part B above the following compounds are prepared:

1-[4-(4-chlorophenyl)-2-(4-aminobenzyloxy)-n-butyl[imidazole;
1-4-(4-chlorophenyl)-2-(2-(4-aminophenyl)ethoxy)-n-butyl]imidazole;
1-[4-(4-chlorophenyl)-2-(3-(4-aminophenyl)propoxy)-n-butyl]imidazole;
1-[4-(4-methoxyphenyl)-2-(4-aminobenzyloxy)-n-butyl]imidazole;
1-[4-(4-methoxyphenyl)-2-(2-(4-aminophenyl)ethoxy)-n-butyl]imidazole;

1-[4-(4-methoxyphenyl)-2-(3-(4-aminophenyl)propoxy)-n-butyl]imidazole;
1-[4-(2,4-dichlorophenyl)-2-(4-aminobenzyloxy)-n-butyl]imidazole;
1-[4-(2,4-dichlorophenyl)-2-(2-(4-aminophenyl)ethoxy)-n-butyl]imidazole;
1-[4-(2,4-dichlorophenyl)-2-(3-(4-aminophenyl)propoxy)-n-butyl]imidazole;
1-[4-(4-methylphenyl)-2-(4-aminobenzyloxy)-n-butyl]imidazole;
1-[4-(4-methylphenyl)-2-(2-(4-aminophenyl)ethoxy)-n-butyl]imidazole;
1-[4-(4-methylphenyl)-2-(3-(4-aminophenyl)propoxy)-n-butyl]imidazole;
1-[4-phenyl-2-(4-aminobenzyloxy)n-butyl]imidazole;
1-[4-phenyl-2-(2-(4-aminophenyl)ethoxy)n-butyl]imidazole;
1-[4-phenyl-2-(3-(4-aminophenyl)propoxy)-n-butyl]imidazole;
1-[4-(4-fluorophenyl)-2-(4-aminobenzyloxy)-n-butyl]imidazole;
1-[4-(4-fluorophenyl)-2-(2-(4-aminophenyl)ethoxy)-n-butyl]imidazole;
1-[4-(4-fluorophenyl)-2-(3-(4-amino-3-fluorophenyl)propoxy)-n-butyl]imidazole;
1-[4-(1-naphthyl)-2-(4-aminobenzyloxy)-n-butyl]imidazole;
1-[4-(1-naphthyl)-2-(2-(4-aminophenylethoxy)-n-butyl]imidazole;
1-[4-(1-naphthyl)-2-(3-(4-aminophenyl)-propoxy)-n-butyl]imidazole;
1-[4-(2-naphthyl)-2-(4-aminobenzyloxy)-n-butyl]imidazole;
1-[4-(2-naphthyl)-2-(2-(4-aminophenyl)ethoxy)-n-butyl]imidazole;
1-[4-(2-naphthyl)-2-(3-(4-aminophenyl)propoxy)-n-butyl]imidazole;
1-[4-(thien-2-yl)-2-(4-aminobenzyloxy)-n-butyl]imidazole;
1-[4-(thien-2-yl)-2-(2-(4-aminophenyl)ethoxy)-n-butyl]imidazole;
1-[4-(thien-2-yl)-2-(3-(4-aminophenyl)propyloxy)-n-butyl]imidazole;
1-[4-(5-chlorothien-2-yl)-2-(4-aminobenzyloxy)-n-butyl]imidazole;
1-[4-(5-chlorothien-2-yl)-2-(2-(4-aminophenyl)ethoxy)-n-butyl]imidazole;
1-[4-(5-chlorothien-2-yl)-2-(3-(4-aminophenyl)propyloxy)-n-butyl]imidazole;
1-[4-(5-methylthien-2-yl)-2-(4-aminobenzyloxy)-n-butyl]imidazole;
1-[4-(5-methylthien-2-yl)-2-(2-(4-aminophenyl)ethoxy)-n-butyl]imidazole;
1-[4-(5-methylthien-2-yl)-2-(3-(4-aminophenyl)propyloxy)-n-butyl]imidazole;
1-[4-(pyridin-4-yl)-2-(4-aminobenzyloxy)-n-butyl]imidazole;
1-[4-(pyridin-4-yl)-2-(2-(4-aminophenyl)ethoxy)-n-butyl]imidazole; and
1-[4-(pyridin-4-yl)-2-(3-(4-aminophenyl)propyloxy)-n-butyl]imidazole.

EXAMPLE 10

1-[4-(4-chlorophenyl)-2-4-acetylaminophenoxy)-n-butyl]imidazole, hydrochloride (1.5 g) in 40 ml of tetrahydrofuran was treated with an equal weight of phosporous pentasulfide and the mixture stirred at 60° C. overnight. Further phosphorous pentasulfide (2.0 g) was added and the mixture heated with stirring over the weekend. The cooled solution was then treated with 20 ml of 10% sodium hydroxide solution, stirred for 6 hours and the mixture extracted with ethyl acetate. The combined extracts were washed with water, dried (MgSO$_4$), evaporated and the residue chromatographed on silica gel eluting with ethyl acetate. The resulting 1-[4-(4-chlorophenyl)-2-(4-methyl(thiocarbonyl)aminophenoxy)-n-butyl]imidazole was dissolved in methanol and treated with excess ethereal hydrogen chloride. The solvent was removed and the residue evacuated to give the hydrochloride salt as a brittle foam, dec. 96°–100° C. (foaming).

EXAMPLE 11

A solution of 1-[4-(4-chlorophenyl)-2-aminophenylthio)-n-butyl]imidazole (680 mg) in 10 ml of dry pyridine was cooled to −40° C. and treated with stirring with 0.5 ml of methyl chloroformate. The mixture was allowed to warm up to room temperature slowly and stirred overnight. After evaporation of the pyridine in vacuo, 30 ml of water was added, and the product extracted with ethyl acetate. The combined extracts were washed, dried (MgSO$_4$), and evaporated to give 1-[4-(4-chlorophenyl)-2-(4-methoxycarbonylaminophenylthio)-n-butyl]imidazole. The hydrochloride salt was obtained by treating a solution of the free base in ethyl acetate with ethereal HCl until precipitation was complete, and collecting the precipitate.

EXAMPLE 12

A suspension of 1-[4-(4-chlorophenyl)-2-4-aminophenylthio)-n-butyl]imidazole (680 mg) in 20 ml of water was treated with 2 ml of 1N hydrochloric acid followed by potassium isocyanate (170 mg), and the mixture stirred overnight at room temperature. The reaction mixture was then treated with excess potassium carbonate solution and the product extracted with ethyl acetate. The combined extracts were washed with water, dried (MgSO$_4$) and evaporated. Chromatography on silica gel eluting with 2.2% water in ethyl acetate gave 1-[4-(4-chlorophenyl)-2-(4-aminocarbonylaminophenylthio)-n-butyl]imidazole.

EXAMPLE 13

A solution of 1-[4-(4-chlorophenyl)-2-(4-aminophenylthio)-n-butyl]imidazole (360 mg) in dry tetrahydrofuran (10 ml) was treated with 0.16 ml of methyl isocyanate. The solution was warmed at gentle reflux overnight and the solvent evaporated. The residue was chromatographed on silica gel eluting with 2.2% water in ethyl acetate to give 1-[4-(4-chlorophenyl)-2-(4-methylaminocarbonylaminophenylthio)-n-butyl]imidazole.

EXAMPLE 14

A solution of 1-[4-(4-chlorophenyl)-2-(4-aminophenylthio)-n-butyl]imidazole (680 mg) and 1 ml of ethyl)isothiocyanate in 20 ml of tetrahydrofuran was heated overnight under gentle reflux. The solvent was then evaporated and the residue chromatographed on silica gel eluting with 2.2% water in ethyl acetate to give 1-[4-(4-chlorophenyl)-2-(4-ethylaminothiocarbonylaminophenylthio)-n-butyl]imidazole.

EXAMPLE 15

To a solution of 1-[4-(4-chlorophenyl)-2-(2,5-dichloro-4-nitrophenoxy)-n-butyl]imidazole (5.0 g)

(prepared using 2,5-dichloro-4-nitrophenol as in Example 1) in 150 ml of methanol at 0° C under nitrogen was added nickel chloride hexahydrate (8.09 g). To this mixture was added sodium borohydride (2.99 g) in one portion, followed after stirring for 20 minutes by 10 ml of acetone. The solvent was then removed and the black residue stirred overnight with 250 ml of concentrated ammonium hydroxide, 150 ml of water and 250 ml dichloromethane. The organic layer was then separated, the aqueous layer extracted further with dichloromethane (3×100 ml) and the combined extracts were washed, dried (MgSO4) and evaporated. The resulting brown gum was chromatographed on silica gel eluting with 5% methanol in methylene chloride to give pure 1-[4-(4-chlorophenyl)-2-(4-amino-2,5-dichlorophenoxy)-n-butyl]imidazole. This was dissolved in ether and treated with ethereal hydrogen chloride until precipitation was complete. The resulting solid, 1-[4-(4-chlorophenyl)-2-(4-amino-2,5-dichlorophenoxy)-n-butyl]imidazole bis(hydrochloride) was filtered off and dried in vacuo (yield 1.8 g), m.p. 115°–124° C. (dec).

Further elution of the above silica gel column gave a second product, 1-[4-(4-chlorophenyl)-2-(4-amino-2-chlorophenoxy)-n-butyl]imidazole (0.6 g), converted as above to the dihydrochloride salt.

EXAMPLE 16

A solution of tert-butyl bromomethyl ketone (30 g) in 500 ml of absolute ethanol at 0° C. was treated with sodium tetrahydroborate (3.17 g) and stirred for 5 hours during which time the temperature was allowed to come to room temperature. The reaction was acidified to pH 1 with concentrated hydrochloric acid and the solvent evaporated. The residual aqueous phase was extracted with ether and the combined ethereal extracts dried over sodium sulfate and concentrated to obtain 1-bromo-3,3-dimethylbutan-2-ol (24.2 g) as an oil, used directly in the next step without further purification.

A mixture of the above bromohydrin (2.49 g), 4-acetylaminothiophenol (2.3 g) and anhydrous potassium carbonate (2.85 g) in 25 ml acetone was stirred and heated under reflux under nitrogen for 18 hours. The solvent was removed and the residue treated with water and extracted with ethyl acetate. The combined extracts were dried (Na2SO4) and the solvent removed to give 1-(4-acetylaminophenylthio)-3,3-dimethylbutan-2-ol (3.84 g) as an oil, which was used in the next step without further purification.

The above crude alcohol (3.80 g) in 30 ml of pyridine at 0° C. was treated with 1.17 ml of methanesulfonyl chloride. The mixture was stirred for 15 hours at room temperature, treated with saturated sodium carbonate solution and extracted with ethyl acetate. The combined extracts were dried (Na2SO4), the solvent evaporated, and the residue treated with toluene and evaporated to remove final traces of pyridine. The crude solid was recrystallized from ethyl acetate (charcoal) to give 2.4 g of 1-(4-acetylaminophenylthio)-2-methanesulfonyloxy-3,3-dimethyl butane, m.p. 123°–124° C.

The methanesulfonate ester from above (2.00 g) in 10 ml of dimethylformamide was treated with imidazole (1.97 g) and the mixture stirred at room temperature for 24 hours and at 80° C. for 8 hours. After the addition of 75 ml of water, the mixture was extracted with ethyl acetate and the combined extracts washed with water, dried (Na2SO4) and the solvent evaporated to give an oil (2.2 g). Chromatography on silica gel eluting with 2.2% water in ethyl acetate gave pure 1-[2-(4-acetylaminophenylthio)-3,3-dimethyl-n-butyl]imidazole (1.5 g) as an oil. Treatment of the free base in ethyl acetate with ethereal hydrogen chloride gave the hydroscopic hydrochloride salt, m.p. 125°–145° C.

EXAMPLE 17

A solution of 1-(3,3-dimethyl-2-hydroxy-n-butyl)imidazole (5.2 g) in a mixture of 50 ml of dimethylformamide and 25 ml of toluene was treated with sodium hydride (3.4 g of 50% dispersion in mineral oil) and stirred at room temperature. After the evolution of hydrogen ceases, manganese dioxide (3.0 g) was added and the mixture cooled in an ice bath. To this mixture was added p-fluoronitrobenzene (8.0 g) and the resulting mixture stirred at room temperature for 3 hours. The reaction mixture was then filtered through Celite washing the residue with toluene, and the filtrate washed several times with water. The toluene layer was separated and dried over sodium sulfate, and evaporated to give yellow crystals. After trituration with ether, the resulting solid was chromatographed on silica gel eluting with 5% methanol in methylene chloride. The resulting product was recrystallized from ethyl acetate to give 6.5 g of 1-[2-(4-nitrophenoxy)-3,3-dimethyl-n-butyl]imidazole.

The above nitro compound (2.00 g) was added to a stirred suspension of finely ground ferrous ammonium sulphate hexahydrate and the mixture heated to reflux. Concentrated ammonium hydroxide was added every two minutes in two ml aliquots until thin layer chromatography showed the reaction to be complete. Absolute ethanol (150 ml) was then added and the reaction mixture filtered through Celite. After evaporation of the solvent the residue was chromatographed on silica gel eluting with 5% methanol in methylene chloride to give 1-[2-(4-aminophenoxy)-3,3-dimethyl-n-butyl]imidazole (1.4 g) as an oil. This was converted to the bis hydrochloride salt as described in Example 16, the salt being recrystallized from ethyl acetate methanol with m.p. 265°–270° C. (dec.).

EXAMPLE 18

A solution of 1-[4-(4-chlorophenyl)-2-(4-N-methylacetylaminophenoxy)-n-butyl]imidazole (2.0 g) in ethyl acetate was treated dropwise with stirring and seeding with ethereal hydrogen chloride until precipitation was complete. The resulting solid was filtered off, washed with ethyl acetate and recrystallized from methanol/acetone to give the hydrochloride salt of 1-[4-(4-chlorophenyl)-2-(4-N-methylacetylaminophenoxy)-n-butyl]imidazole, m.p. 229°–231° C.

EXAMPLE 19

A suspension of 1-[4-(4-chlorophenyl)-2-(4-N-methylacetylaminophenoxy)-n-butyl]imidazole, hydrochloride salt (1.5 g) in dichloromethane (30 ml) was stirred with excess aqueous potassium carbonate until no solid remained. The organic phase was then separated, washed with water, dried (MgSO4) and evaporated to give the free base as a gum.

EXAMPLE 20

The following illustrates the preparation of representative pharmaceutical formulations utilizing an active compound of the instant invention.

| A. Topical Formulation | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q/s 100 |

All of the above ingredients, except water, are combined and heated at 60° C. with stirring. A sufficient quantity of water at 60° C. is then added with vigorous stirring to provide 100 g of the cream formulation which is then cooled to room temperature

| B. Parenteral Formulation | |
|---|---|
| Active compound | 0.5 g |
| Propylene glycol | 20 g |
| Polyethylene glycol 400 | 20 g |
| Tween 80 | 1 g |
| 0.9 Saline solution qs | 100 ml |

The active compound is dissolved in propylene glycol, polyethylene glycol 400 and and Tween 80. A sufficient quantity of 0.9% saline solution is then added with stirring to provide 100 ml of the I.V. solution which is filtered through a 0.2 micron membrane filter and packaged under sterile conditions.

| C. Oral Formulation | parts by weight |
|---|---|
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg of active compound) with an appropriate tabletting machine.

EXAMPLE 21

The following illustrates the preparation of a vaginal contraception composition utilizing an active compound of the present invention.

| | Percent by wt/vol. |
|---|---|
| Active Ingredient | 1 |
| EDTA | 0.5 |
| Poloxamer-407-(Pluronic F-127) (MW 11,500) | 18 |
| PEG 400 | 20 |
| Glycerin | 20 |
| Polysorbate 60 | 3 |
| BHA | .02 |
| Water, qs ad | 100 |

The composition is prepared by mixing all the ingredients with approximately 90% of the required water and allowing the polyoxyethylene-polyoxypropylene block copolymer to hydrate and completely dissolve with gentle stirring. When a clear gel is obtained, the remaining water is added to adjust the volume to 100 ml.

What is claimed is:

1. A compound of the formula

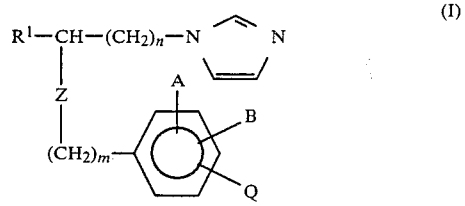

and the acid addition salts thereof wherein
Z is oxygen or sulfur;
m is 0, 1, 2 or 3;
n is 1, 2 or 3;
$R^1$ is
  (a) hydrogen;
  (b) alkyl;
  (c) cycloalkyl optionally substituted by one or more lower alkyl;
  (d) cycloalkyl-lower-alkyl;
  (e) phenyl;
  (f) phenyl-lower-alkyl;
  wherein the phenyl ring in (e) and (f) is optionally substituted by one or more halo, lower alkyl, lower alkoxy, lower alkylthio, cyano or trifluoromethyl;
  (g) naphthyl; or
  (h) naphthyl-lower-alkyl
A and B are independently hydrogen, halo, lower alkyl or lower alkoxy and either one of A or B may be nitro, amino or alkanoylamino;
Q is $NR^2R^3$ wherein
  $R^2$ is hydrogen; alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl or lower alkoxy;
  and $R^3$ is hydrogen or lower alkyl;
with the proviso that when $R^1$ is optionally substituted phenyl, Z is oxygen, n is 1 and m is 0, 1 or 2, Q is not amino unless A or B is alkanoylamino; and that when $R^1$ is optionally substituted phenyl, Z is sulfur, m is 0 and n is 1, Q is not amino.

2. A compound of claim 1 wherein $R^1$ is selected from the group consisting of hydrogen, alkyl, cycloalkyl optionally substituted by one or more lower alkyl and cycloalkyl-lower-alkyl.

3. A compound of claim 2 wherein Q is $NR^2R^3$ wherein $R^2$ and $R^3$ are as defined in claim 1.

4. A compound of claim 3 wherein $R^2$ is hydrogen; alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl or lower alkoxy; and $R^3$ is hydrogen or lower alkyl.

5. The compound of claim 4 which is 1-[2-(4-aminophenoxy)-3,3-dimethylbutyl]imidazole and the acid addition salts thereof.

6. A compound of claim 2 wherein C is $NR^4C(X)YR^5$ wherein $R^4$, $R^5$, X and Y are as defined in claim 1.

7. The compound of claim 6 which is 1-[2-(4-acetylaminophenoxy)-n-octyl]imidazole and the acid addition salts thereof.

8. A compound of claim 1 wherein $R^1$ is selected from the group consisting of monocyclic heteroaromatic ring and monocyclic heteroaromatic ring-lower-alkyl wherein the ring is attached through a carbon atom and is optionally substituted by one halo, hydroxy, nitro, lower alkyl, lower alkoxy or lower alkylthio.

9. A compound of claim 8 wherein C is $NR^2R^3$ wherein $R^2$ and $R^3$ are as defined in claim 1.

10. A compound of claim 9 wherein $R^2$ is hydrogen; alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl or lower alkoxy; and $R^3$ is hydrogen or lower alkyl.

11. A compound of claim 1 wherein $R^1$ is selected from the group consisting of phenyl, phenyl-lower-alkyl, naphthyl and naphthyl-lower-alkyl wherein the phenyl ring is optionally substituted by one or more halo, lower alkyl, lower alkoxy, lower alkylthio, cyano or trifluoromethyl.

12. A compound of claim 11 wherein Q is $NR^2R^3$ wherein $R^2$ and $R^3$ are as defined in claim 1.

13. A compound of claim 12 wherein $R^2$ is hydrogen; alkyl; cycloalkyl optionally substituted by one or more lower alkyl; cycloalkyl-lower-alkyl; phenyl or phenyl-lower-alkyl wherein the phenyl ring is optionally substituted by one or two halo, lower alkyl or lower alkoxy; and $R^3$ is hydrogen or lower alkyl.

14. The compound of claim 13 which is 1-[3-(4-chlorophenyl)-2-(4-aminophenylthio)-n-propyl]imidazole and the acid addition salts thereof.

15. The compound of claim 13 which is 1-[4-(4-chlorophenyl)-2-(2-aminophenylthio)-n-butyl]imidazole and the acid addition salts thereof.

16. The compound of claim 13 which is 1-[4-(4-chlorophenyl)-2-(3-aminophenylthio)-n-butyl]imidazole and the acid addition salts thereof.

17. The compound of claim 13 which is 1-[4-(4-chlorophenyl)-2-(4-aminophenylthio)-n-butyl]imidazole and the acid addition salts thereof.

18. The compound of claim 13 which is 1-[5-(4-chlorophenyl)-2-(4-aminophenylthio)-n-pentyl]imidazole and the acid addition salts thereof.

19. The compound of claim 13 which is 1-[4-(4-chlorophenyl)-2-(4-aminophenoxy)-n-butyl]imidazole and the acid addition salts thereof.

20. The compound of claim 13 which is 1-[4-(4-chlorophenyl)-2-(4-N-methylaminophenoxy)-n-butyl]imidazole and the acid addition salts thereof.

21. The compound of claim 13 which is 1-[4-(4-chlorophenyl)-2-(4-N,N-dimethylaminophenoxy)-n-butyl]imidazole and the acid addition salts thereof.

22. The compound of claim 13 which is 1-[4-(4-chlorophenyl)-2-(4-amino-2,5-dichlorophenoxy)-n-butyl]imidazole and the acid addition salts thereof.

23. The compound of claim 13 which is 1-[4-(4-chlorophenyl)-2-(4-amino-2,6-dichlorophenoxy)-n-butyl]imidazole and the acid addition salts thereof.

24. A male oral contraceptive composition which comprises an oral contraceptively effective amount of a compound of claim 1 and an acceptable carrier.

25. A method of male oral contraception which comprises orally administering an oral contraceptively effective amount of a compound of claim 1 to a male mammal.

* * * * *